(12) United States Patent
Georgakoudi et al.

(10) Patent No.: US 10,712,272 B2
(45) Date of Patent: Jul. 14, 2020

(54) SYSTEM AND METHOD FOR ASSESSING CELLULAR METABOLIC ACTIVITY

(71) Applicant: Trustees of Tufts College, Boston, MA (US)

(72) Inventors: Irene Georgakoudi, Winchester, MA (US); Dimitra Pouli, Medford, MA (US); Kyle P. Quinn, Fayetteville, AR (US); Zhiyi Liu, Medford, MA (US)

(73) Assignee: TRUSTEES OF TUFTS COLLEGE, Boston, MA (US)

( * ) Notice: Subject to any disclaimer, the term of this patent is extended or adjusted under 35 U.S.C. 154(b) by 284 days.

(21) Appl. No.: 15/717,783

(22) Filed: Sep. 27, 2017

(65) Prior Publication Data
US 2018/0088051 A1    Mar. 29, 2018

Related U.S. Application Data

(60) Provisional application No. 62/400,430, filed on Sep. 27, 2016.

(51) Int. Cl.
*G01N 21/64* (2006.01)
*C12Q 1/00* (2006.01)
(Continued)

(52) U.S. Cl.
CPC ......... *G01N 21/6486* (2013.01); *C12Q 1/008* (2013.01); *G01N 33/582* (2013.01);
(Continued)

(58) Field of Classification Search
CPC .. C12Q 1/008; G01N 21/6486; G01N 33/582; G01N 2800/7066;
(Continued)

(56) References Cited

U.S. PATENT DOCUMENTS

| 8,574,859 | B2* | 11/2013 | Lin | ...... | A61B 5/0059 |
| | | | | | 422/68.1 |
| 2014/0363840 | A1* | 12/2014 | Mycek | ...... | G01N 33/5005 |
| | | | | | 435/29 |
| 2015/0346100 | A1* | 12/2015 | Racowsky | ...... | G01N 21/6408 |
| | | | | | 435/34 |

OTHER PUBLICATIONS

Gehlsen et al. Graefes Arch. Clin. Exp. Ophthalmol, vol. 250, 2012, pp. 1293-1302.*
(Continued)

*Primary Examiner* — Maureen Wallenhorst
(74) *Attorney, Agent, or Firm* — Nelson Mullins Riley & Scarborough LLP

(57) ABSTRACT

Methods and corresponding apparatus and systems for assessing cellular metabolic activity are disclosed. In one aspect, a cell can be illuminated with optical radiation in order to cause multi-photon excitation of at least one endogenous metabolic cofactor in that cell and cause the excited metabolic cofactor to emit fluorescent radiation. A detector can be used to detect the fluorescent radiation emitted by the excited endogenous metabolic cofactor. A computer processor can analyze the fluorescent radiation to derive the following parameters: (1) using a computer processor to analyze the intensity of the fluorescent radiation, (2) a fluorescence lifetime of at least one of the excited metabolic cofactor, (3) a parameter indicative of mitochondrial clustering in the cell. These parameters can be used to assess at least one metabolic process of the cell.

60 Claims, 38 Drawing Sheets

(51) Int. Cl.
  *G01N 33/52* (2006.01)
  *G06T 7/00* (2017.01)
  *G06T 7/20* (2017.01)
  *G01N 33/58* (2006.01)

(52) U.S. Cl.
  CPC .............. *G06T 7/0016* (2013.01); *G06T 7/20* (2013.01); *G01N 2800/7066* (2013.01); *G06T 2207/10064* (2013.01); *G06T 2207/30024* (2013.01)

(58) Field of Classification Search
  CPC . G06T 2207/10064; G06T 2207/30024; G06T 7/0012; G06T 7/0016; G06T 7/20
  USPC ............ 436/63, 164, 172; 422/82.05, 82.08; 435/29, 325, 366, 372, 375
  See application file for complete search history.

(56) References Cited

OTHER PUBLICATIONS

Vergen et al. Microsc. Microanal., vol. 18(4), Aug. 2012, pp. 1-16.*
Liu et al. Science Advances, vol. 4, Mar. 7, 2018, pp. 1-14.*
Abbott et al., Ann Biomed Eng. Mar. 2016 ; 44(3): 725-732.
Alonzo et al., "Two-photon excited fluorescence of intrinsic fluorophores enables label-free assessment of adipose tissue function", Sci Rep. Aug. 5, 2016;6:31012.
Chang et al., "Non-invasive monitoring of cell metabolism and lipid production in 3D engineered human adipose tissues using label-free multiphoton microscopy", Biomaterials 34 (2013) 8607-8616.
Georgakoudi et al., "Optical Imaging Using Endogenous Contrast to Assess Metabolic State", Biomed Eng.2012.14:351-367.
Levitt et al., "Diagnostic cellular organization features extracted from autofluorescence images", Optic Letters Nov. 15, 2007; vol. 32, No. 22: 3305-3307.
Levitt et al., "Automated Biochemical, Morphological, and Organizational Assessment of Precancerous Changes from Endogenous Two-Photon Fluorescence Images", PLoS One. 2011;6(9):e24765: 1-11.
Mujat et al., "Endogenous optical biomarkers of normal and human papillomavirus immortalized epithelial cells", Int. J. Cancer: 122, 363-371 (2008).
Pouli et al., "Imaging mitochondrial dynamics in human skin reveals depth-dependent hypoxia and malignant potential for diagnosis", Sci. Transl. Med. 8, 367ra169 (2016): 1-11.
Quinn et al., "Characterization of metabolic changes associated with the functional development of 3D engineered tissues by non-invasive, dynamic measurement of individual cell redox ratios", Biomaterials 33 (2012) 5341-5348.
Quinn et al., "Quantitative metabolic imaging using endogenous fluorescence to detect stem cell differentiation",Sci Rep. Dec. 5, 2013;3:3432: 1-10.
Rice et al., "Quantitative biomarkers of stem cell differentiation based on intrinsic two-photon excited fluorescence", J Biomed Opt. Nov.-Dec. 2007;12(6):060504.
Rice et al., "Two-Photon Microscopy for Non-Invasive, Quantitative Monitoring of Stem Cell Differentiation", Plos One. Apr. 2010; vol. 5(4) e10075: 1-13.
Stuntz et al., "Endogenous Two-Photon Excited Fluorescence Imaging Characterizes Neuron and Astrocyte Metabolic Responses to Manganese Toxicity", Sci Rep. Apr. 21 2017;7(1):1041: 1-15.
Varone et el., "Endogenous Two-Photon Fluorescence Imaging Elucidates Metabolic Changes Related to Enhanced Glycolysis and Glutamine Consumption in Precancerous Epithelial Tissues", Cancer Res. Jun. 1, 2014; 74(11): 3067-3075.
Ward et al., "Noninvasive Metabolic Imaging of Engineered 3D Human Adipose Tissue in a Perfusion Bioreactor", Plos One Feb. 2013; vol. 8 (2):e55696: 1-8.
Xylas et al., "Intrinsic optical biomarkers associated with the invasive potential of tumor cells in engineered tissue models" Dec. 1, 2010 / vol. 1, No. 5 Biomadical Optics Express 1387-1400.
Xylas et al., "Noninvasive assessment of mitochondrial organization in three-dimensional tissues reveals changes associated with cancer development", Int J Cancer. Jan. 15, 2015; 136(2): 322-332.
Xylas et al., "Improved Fourier-based characterization of intracellular fractal features", Oct. 8, 2012 / vol. 20, No. 21 Optics Express 23442-23455.

* cited by examiner

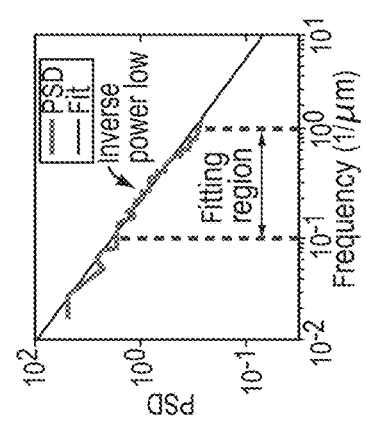
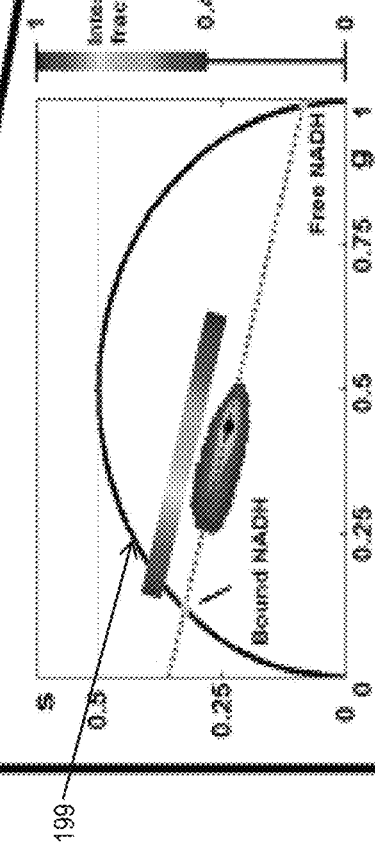
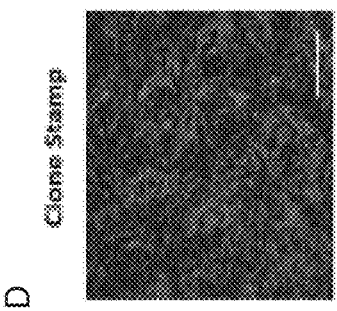
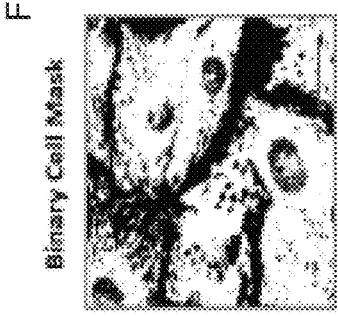
FIG. 2A  FIG. 2B  FIG. 2C  FIG. 2D  FIG. 2E  FIG. 2F  FIG. 2G  FIG. 2H

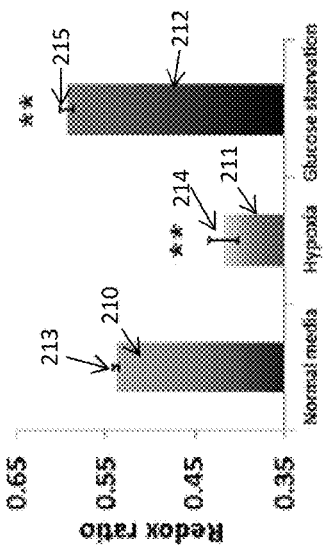
FIG. 4D-1　FIG. 4D-2　FIG. 4D-3
FIG. 4E
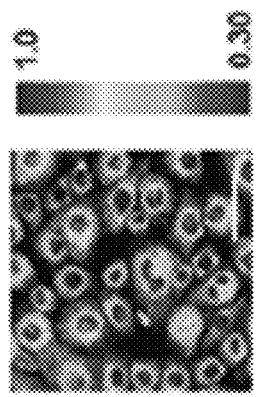
FIG. 4F-1　FIG. 4F-2　FIG. 4F-3
FIG. 4G
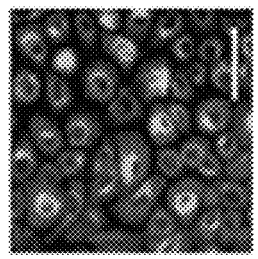
FIG. 4H-1　FIG. 4H-2　FIG. 4H-3
FIG. 4I

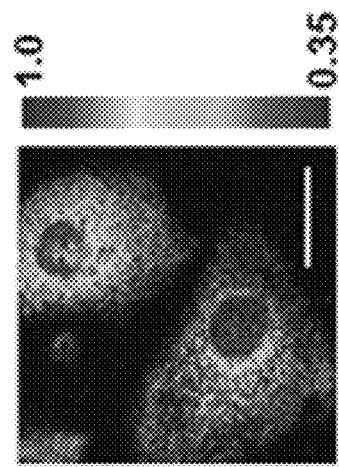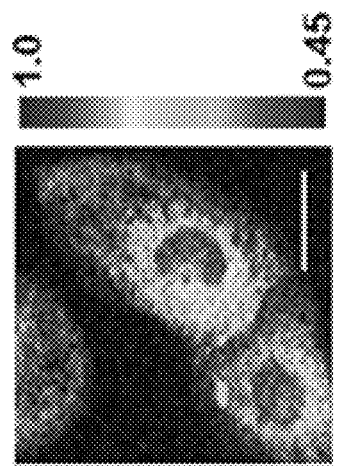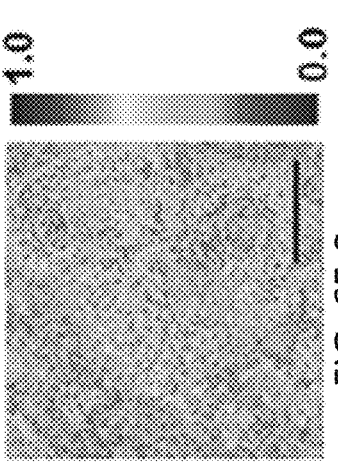
FIG. 6A-1  FIG. 6A-2  FIG. 6C-1  FIG. 6C-2  FIG. 6E-1  FIG. 6E-2

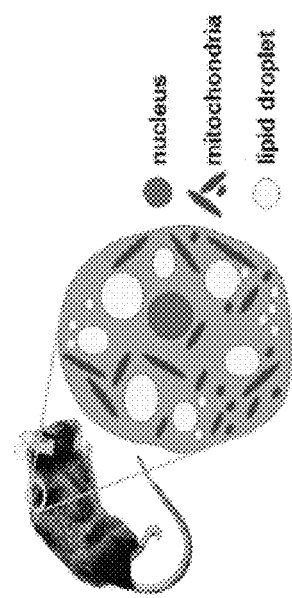
FIG. 9A
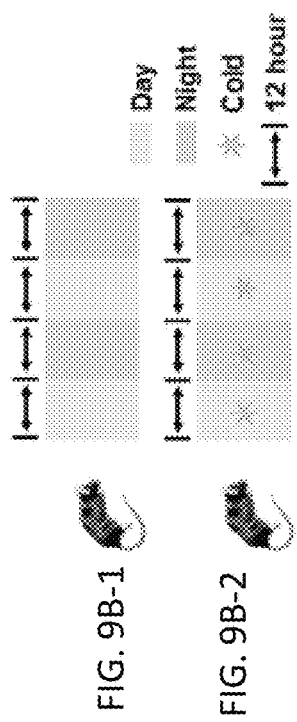
FIG. 9B-1
FIG. 9B-2
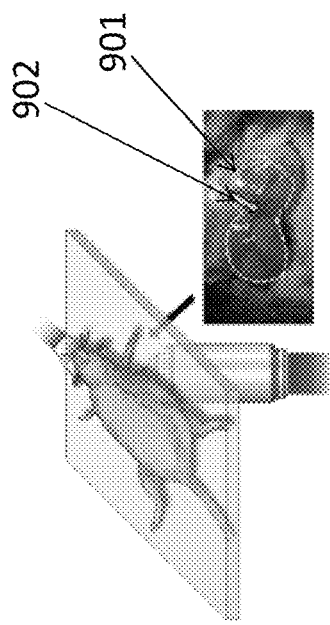
FIG. 9C

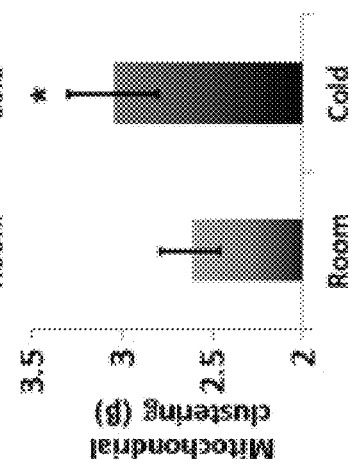
FIG. 9E
FIG. 9G
FIG. 9I
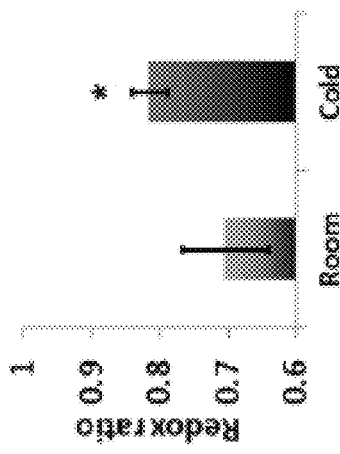
FIG. 9D-1  FIG. 9D-2
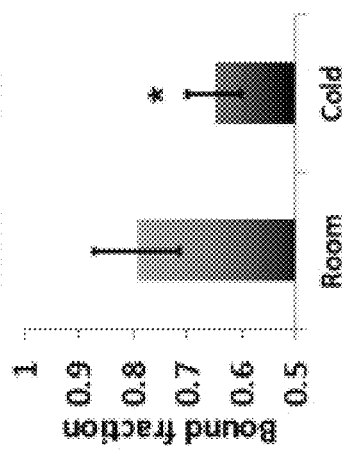
FIG. 9F-1  FIG. 9F-2
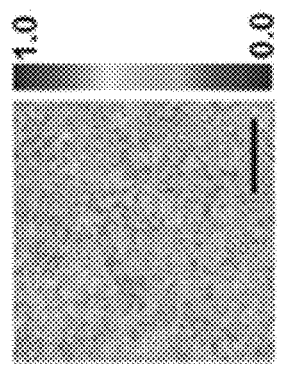
FIG. 9H-1  FIG. 9H-2

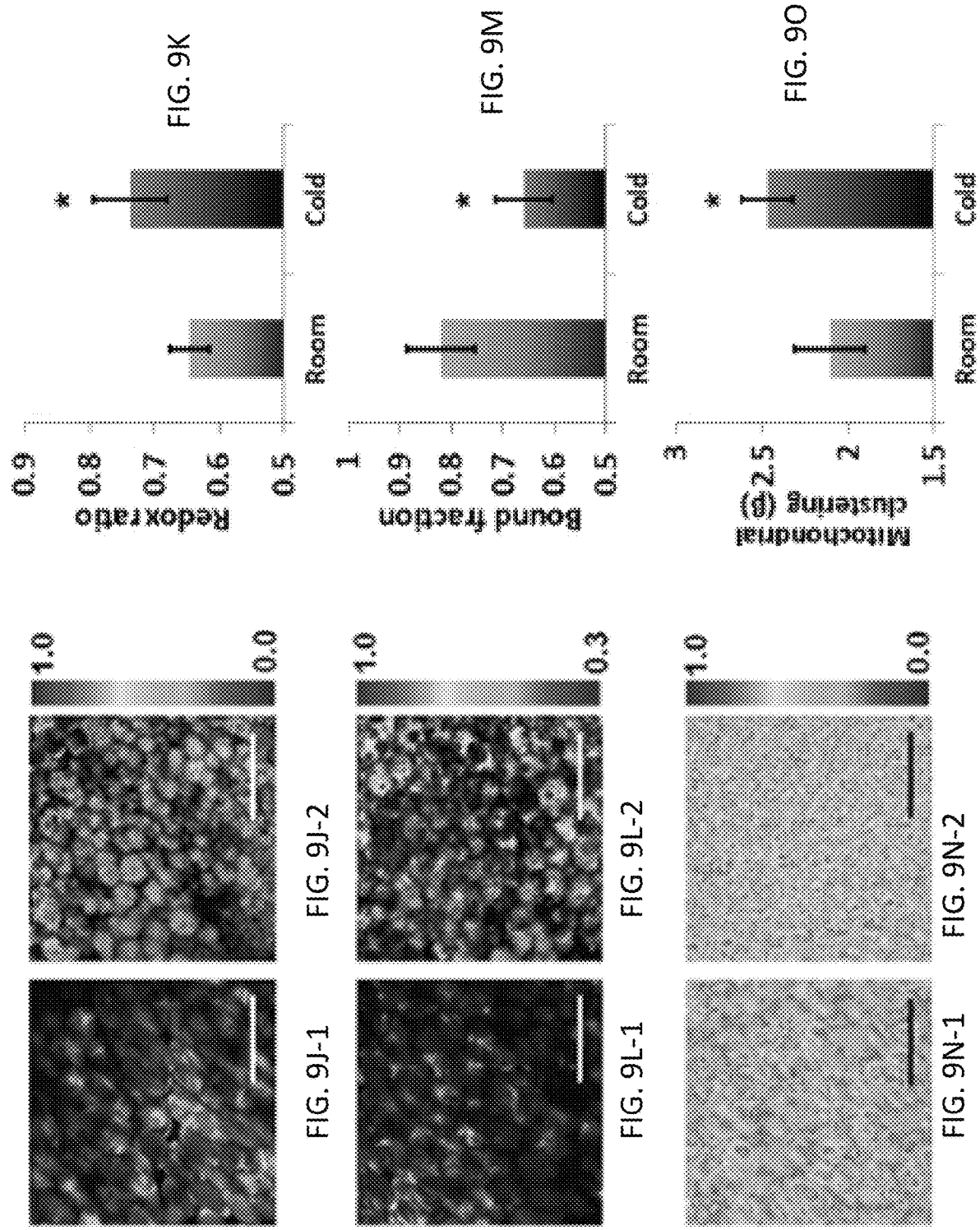

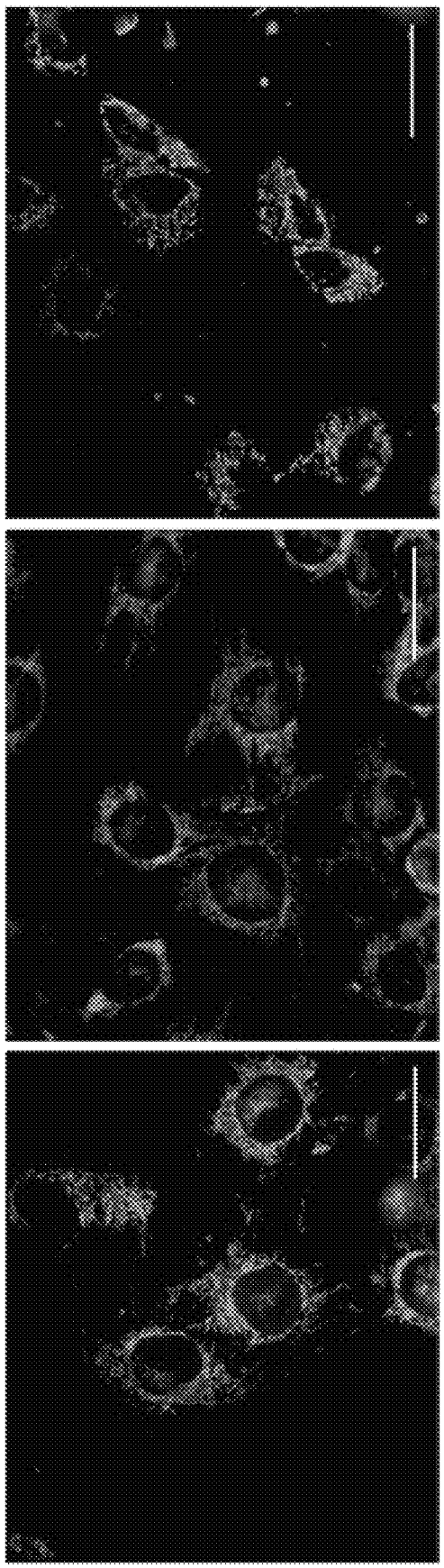

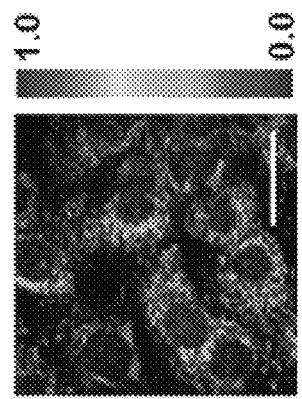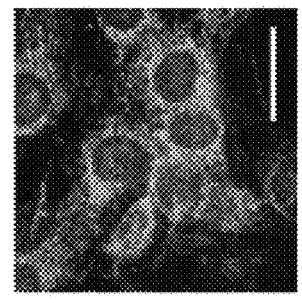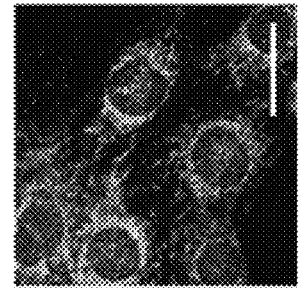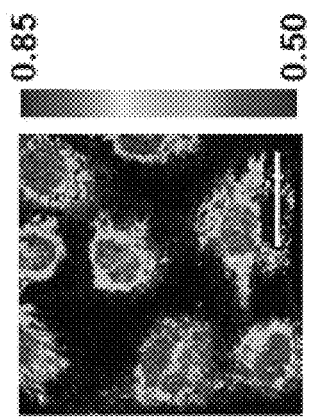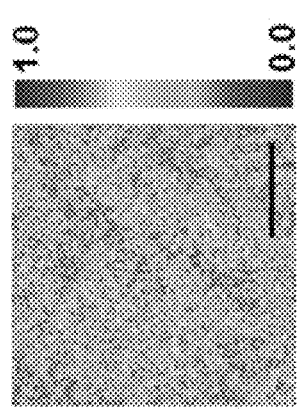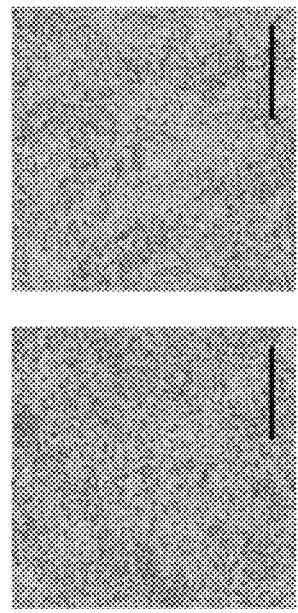

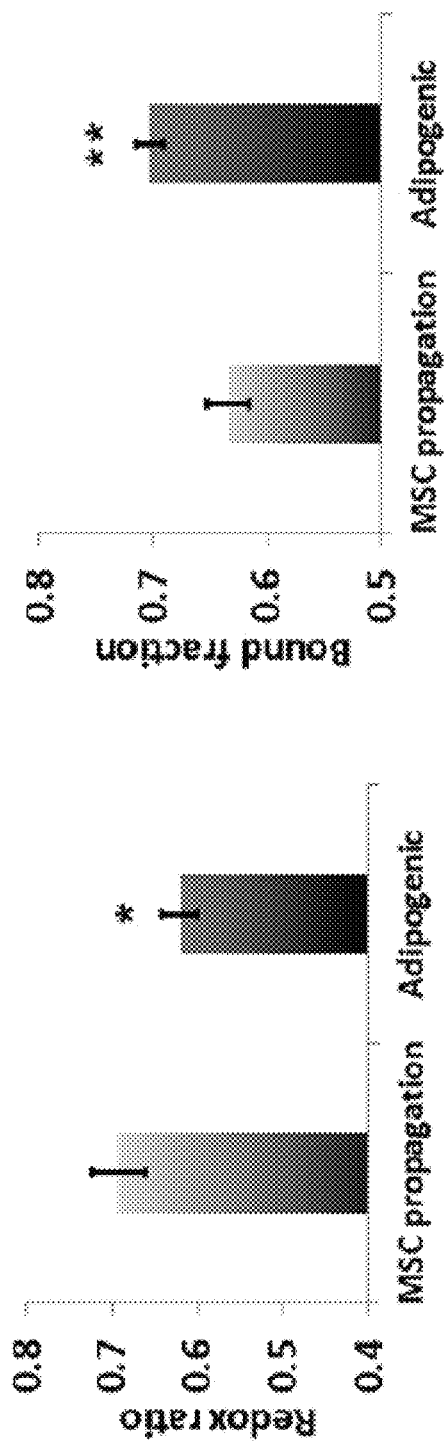
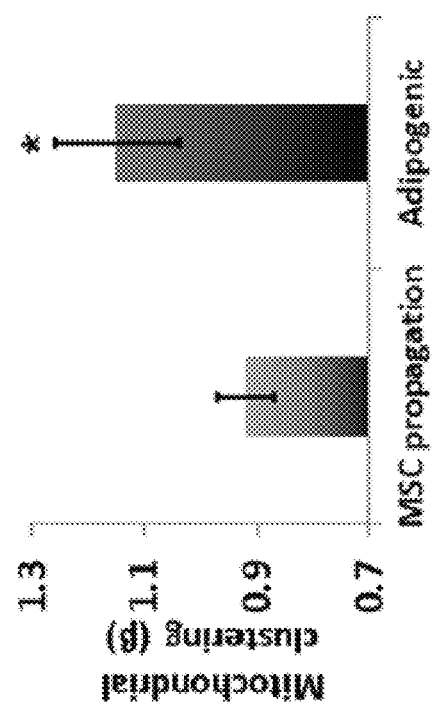
FIG. 14B
FIG. 14D
FIG. 14F

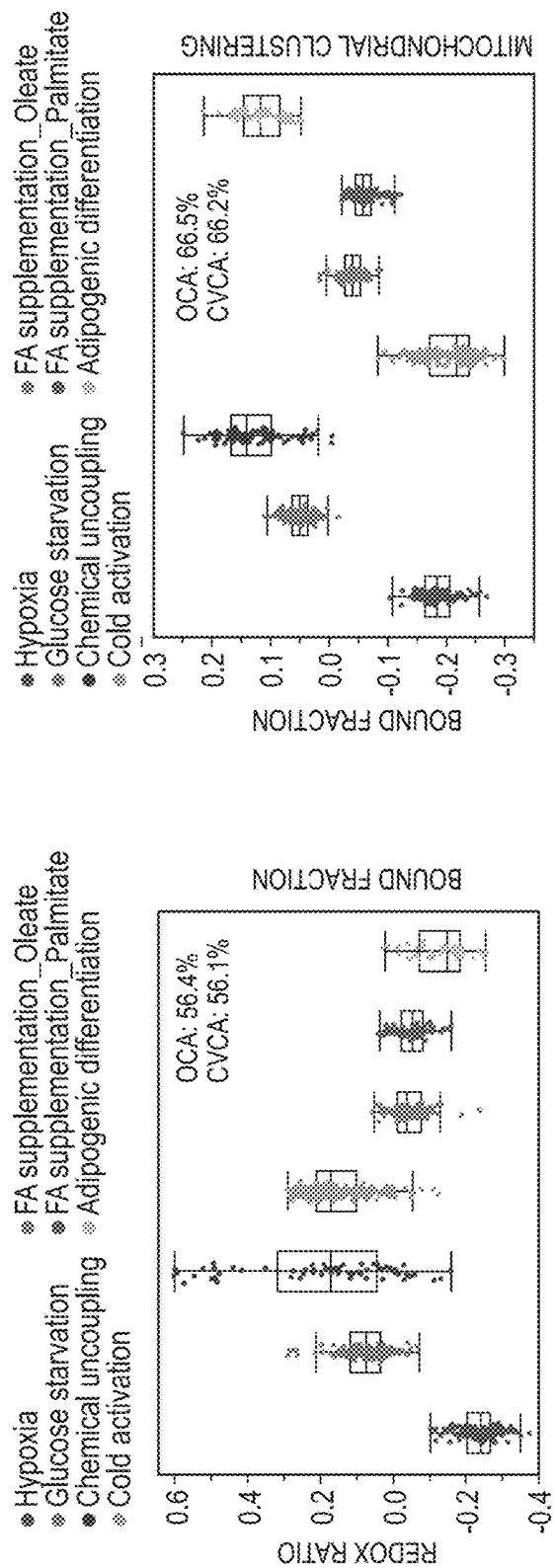
FIG. 15A
FIG. 15B
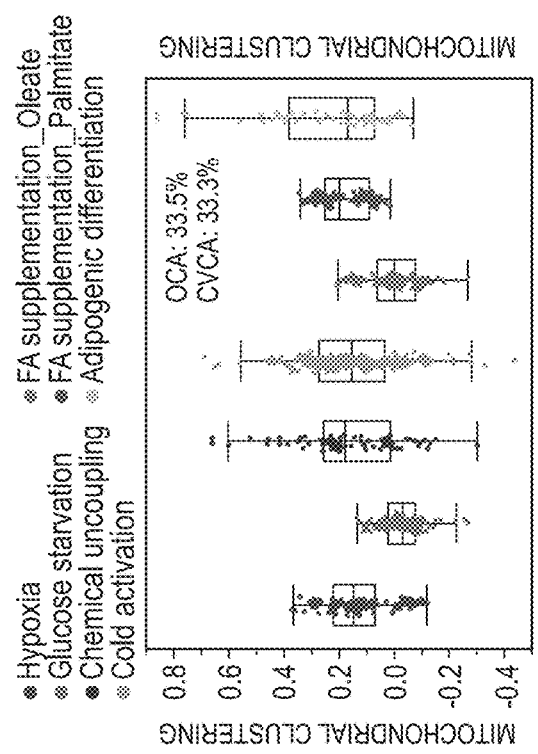
FIG. 15C

| Pathway | Treatment | Redox ratio | Bound fraction | Mitochondrial clustering |
|---|---|---|---|---|
| Glycolysis and glutaminolysis | Normal media | 0.015±0.002 | 0.008±0.001 | 0.081±0.004 |
|  | Hypoxia | 0.017±0.005 | 0.014±0.004* | 0.189±0.015* |
|  | Glucose starvation | 0.025±0.007 | 0.008±0.001 | 0.103±0.009 |
| Chemical uncoupling | Control | 0.045±0.002 | 0.008±0.004 | 0.071±0.020 |
|  | CCCP | 0.102±0.011* | 0.026±0.001* | 0.126±0.013* |
| Cold activation_ex vivo | Room | 0.033±0.002 | 0.029±0.005 | 0.064±0.025 |
|  | Cold | 0.030±0.003 | 0.022±0.005 | 0.077±0.018 |
| Cold activation_in vivo | Room | 0.033±0.003 | 0.010±0.007 | 0.220±0.010 |
|  | Cold | 0.035±0.003 | 0.017±0.013 | 0.244±0.027 |
| β-oxidation | Vehicle | 0.009±0.001 | 0.008±0.002 | 0.055±0.019 |
|  | Oleate | 0.018±0.002* | 0.010±0.002 | 0.140±0.022* |
|  | Palmitate | 0.012±0.001 | 0.011±0.002 | 0.138±0.010* |
| Lipid synthesis | MSC propagation | 0.015±0.004 | 0.015±0.003 | 0.070±0.006 |
|  | Adipogenic | 0.037±0.009* | 0.021±0.004 | 0.137±0.030* |

The significance symbol indicates significant difference compared with corresponding control in each experiment. Differences are evaluated using an ANOVA with post-hoc Tukey HSD test if there are multiple groups (glycolysis and glutaminolysis, and β-oxidation). Otherwise a two-tailed t-test is used. *, $p < 0.05$.

FIG. 16

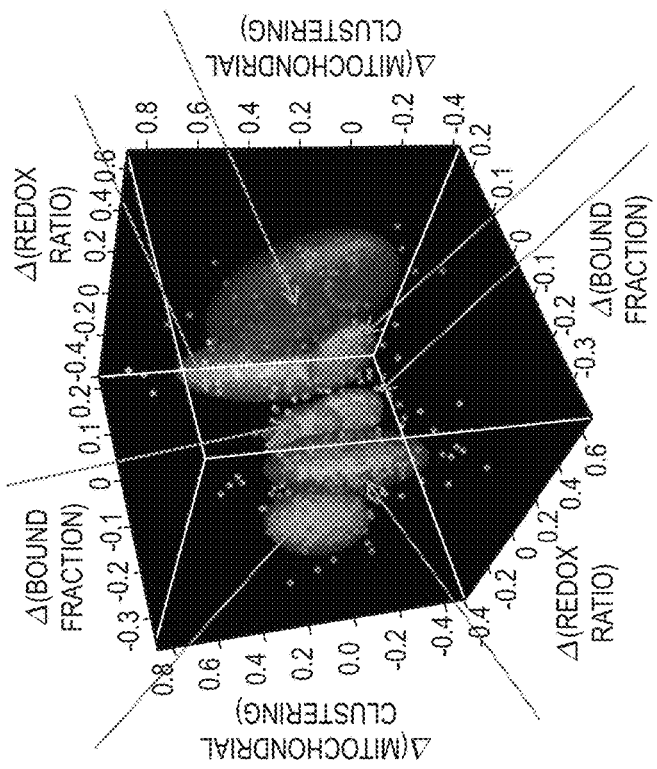
FIG. 17A
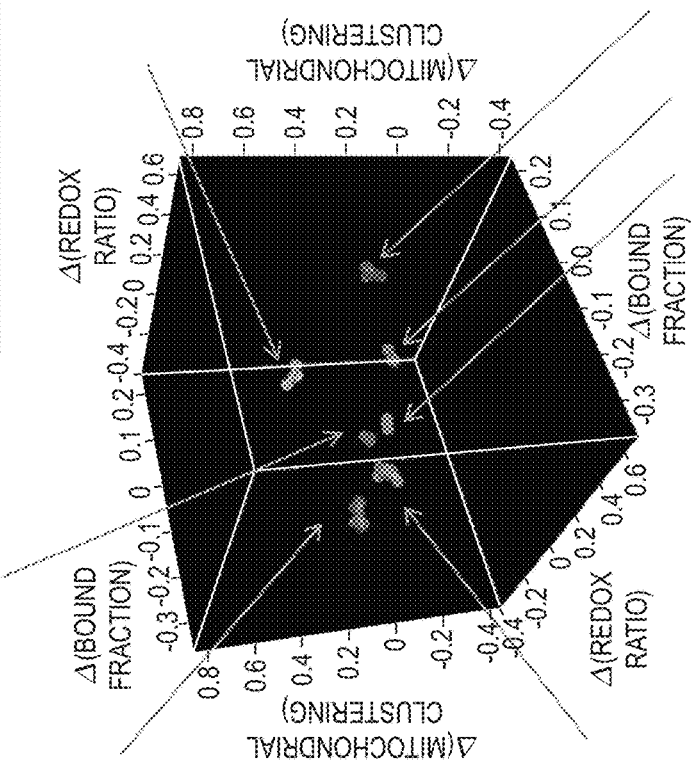
FIG. 17B
FIG. 17C

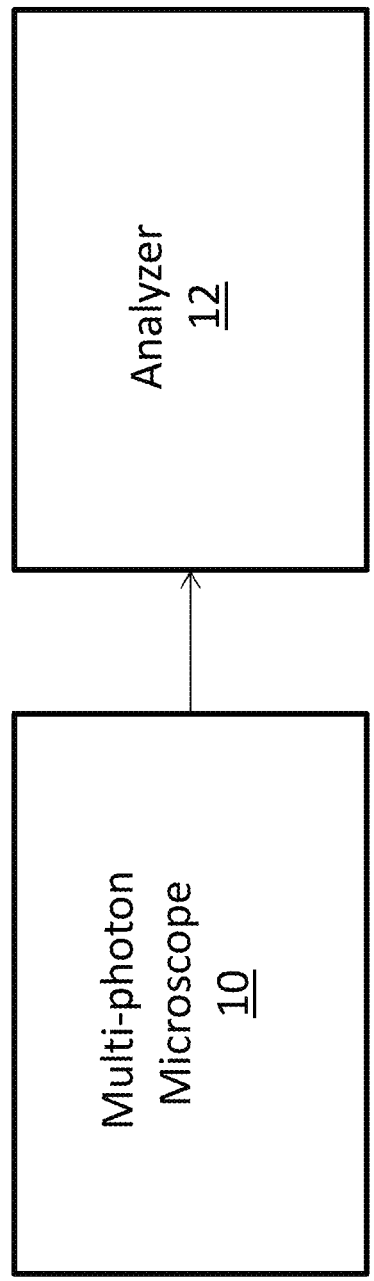

SYSTEM AND METHOD FOR ASSESSING CELLULAR METABOLIC ACTIVITY

CROSS-REFERENCE AND RELATED APPLICATIONS

This application claims benefit of U.S. Provisional Patent Application Ser. No. 62/400,430 filed Sep. 27, 2016, the teachings of which is incorporated herein by reference in its entirety.

TECHNICAL FIELD

The present invention relates generally to method and corresponding system and apparatus for assessing cellular metabolic activity, and more particularly, but not by way of limitation, to apparatus, system, and method for assessing cellular metabolic activity of a cell based on assessment of endogenous Nicotinamide Adenine Dinucleotide (Phosphate) (NAD(P)H) and Flavin Adenine Dinucleotide (FAD) in that cell.

BACKGROUND

Metabolism is responsible for many life sustaining chemical processes that support cellular function through molecular and energetic transformations. Numerous pathways have evolved to sustain cellular bioenergetics and their balance can be critical for normal development and aging. Conversely, metabolic perturbations or dysfunctions are often implicated in numerous diseases, including obesity, diabetes, cancer, cardiovascular and neurodegenerative disorders. Accordingly, the ability to monitor subcellular functional and structural changes associated with metabolism can be essential for understanding tissue development and disease progression. However, established techniques are often either destructive or require the use of exogenous agents.

Generally, metabolic responses can be highly dynamic and heterogeneous both temporally and spatially, and this inherent heterogeneity can impact disease development or response to treatment significantly. Traditional imaging tools for assessing metabolic activity in vivo typically require addition of exogenous agents and can often have limited resolution and sensitivity. More sensitive, quantitative metabolic assays, such as those based on mass spectrometry and carbon labeling, cannot be readily performed within living cells and require cell and tissue homogenization. Therefore, such techniques can have limited capabilities for capturing dynamic or heterogeneous aspects of metabolic responses.

High resolution fluorescence imaging based approaches that rely on exogenous fluorescent probes can be sensitive to mitochondrial membrane potential or target specific cellular organelles or proteins, and can, therefore, overcome the latter limitations. However, such techniques often require cellular manipulations and can be confounded by artifacts related to the distributions of the fluorophores, especially in more complex, three-dimensional (3D) tissues. Therefore, quantitative, high-resolution, label-free techniques for examining metabolic processes, non-invasively and in vivo in 3D tissues, are needed to assist with characterizing and elucidating the role of different metabolic pathways in disease development, and as potential therapeutic targets.

Additionally, mitochondria can undergo trafficking, fusion, and fission, creating continuously changing networks to support mitochondrial function and accommodate cellular homeostasis. Aberrant mitochondrial dynamics and the corresponding changes in mitochondrial organization are increasingly associated with a variety of human pathologies, including neurodegenerative, metabolic, cardiovascular and neoplastic diseases. Many conventional methods for investigating mitochondrial morphology are invasive relying, for example, on scanning electron microscopy, mitochondria-specific dyes, or genetically engineered expression of fluorescent proteins. Accordingly, there is a need for improved methods and systems for assessing mitochondrial organization and dynamics.

SUMMARY

In one aspect, a method and corresponding system and apparatus for assessing cellular metabolic activity is disclosed. The disclosed method includes illuminating at least one cell with optical radiation in order to cause multi-photon, e.g., two-photon, excitation of at least one endogenous metabolic cofactor in that cell and cause the excited metabolic cofactor to emit fluorescent radiation. A detector can be used to detect the fluorescent radiation emitted by the excited endogenous metabolic cofactor, and a computer processor can be used to analyze the fluorescent radiation to derive the following parameters: (1) an intensity of the fluorescent radiation, (2) a fluorescence lifetime of at least one of the excited metabolic cofactor(s), and (3) a parameter indicative of mitochondrial clustering in the cell. The derived parameters can be used to assess at least one metabolic process of the cell.

In another aspect, method and corresponding system and apparatus for assessing cellular metabolic activity includes illuminating at least one cell with optical radiation in order to cause multi-photon, e.g., two-photon, excitation of at least two endogenous metabolic cofactors in that cell and cause the excited metabolic cofactors to emit fluorescent radiation. A detector can be used to detect the fluorescent radiation emitted by the excited metabolic cofactors, and a computer processor can be used to analyze the fluorescent radiation to derive the following parameters: (1) an optical redox ratio of the at least two metabolic cofactors, (2) a fluorescence lifetime of at least one of the metabolic cofactors, and (3) a parameter indicative of mitochondrial clustering in the cell. The derived parameters can be used to assess at least one metabolic process of the cell.

In another aspect, a method for assessing cellular metabolic activity is disclosed. The disclosed method includes excitation of endogenous NAD(P)H and Flavin Adenine Dinucleotide (FAD) in that cell, and, thereby, causing excited NAD(P)H and FAD to emit fluorescent radiation. The term NAD(P)H, as used herein, refers to any of NADH (Nicotinamide Adenine Dinucleotide) and NADPH (Nicotinamide Adenine Dinucleotide Phosphate). A detector can be used to detect the fluorescent radiation emitted by the excited NAD(P)H and FAD, and a computer processor can be used to analyze the fluorescent radiation to derive the following parameters: (1) an optical redox ratio of NAD(P)H and FAD, (2) a fluorescence lifetime of NAD(P)H, and (3) a parameter indicative of mitochondrial clustering in said cell.

In another aspect, a method for assessing cellular metabolic activity is disclosed. The disclosed method includes illuminating at least one cell with laser radiation so as to cause multi-photon, e.g., two-photon, excitation of at least two endogenous chromophores in the cell, thereby causing the excited chromophores to emit fluorescent radiation. A detector can be used to detect the fluorescent radiation emitted by the excited chromophores and a computer processor can be used to analyze the fluorescent radiation to derive the following parameters: (1) an optical redox ratio of said chromophores, (2) a fluorescence lifetime of at least one of said chromophores, and (3) a measure of mitochondrial clustering in said cell. The derived parameters can be used to assess at least one metabolic pathway of the cell.

In yet another aspect, a system for assessing cellular metabolic activity that includes an optical radiation source (e.g., a laser), at least one detector, and an analysis module is disclosed. The optical radiation source can illuminate at least one cell with optical radiation suitable for providing multi-photon excitation of at least one endogenous cellular metabolic cofactor, e.g., NAD(P)H and/or FAD, and the at least one detector can detect the fluorescent radiation emitted from the multi-photon excited cofactor(s), and generate at least one signal indicative of the detected fluorescent radiation. The analysis module can include a processor that is configured to receive the at least one signal and operate on the signal to determine the following parameters: (1) the intensity of the fluorescent radiation, (2) a fluorescence lifetime of the cofactor(s), and (3) a parameter indicative of mitochondrial clustering in the cell. In some embodiments, the optical radiation is employed to excite at least two endogenous metabolic cofactors. By way of example, In some such embodiments, one metabolic cofactor can be NAD(P)H and the other cofactor can be FAD. In some such embodiments, the analysis module is configured to determine the following parameter: (1) an optical redox ratio of NAD(P)H and FAD, (2) a fluorescence lifetime of NAD(P)H, and (3) a parameter indicative of mitochondrial clustering in said cell. The analysis module can be further configured to use the above parameters to assess, e.g., determine a change, in one or more cellular metabolic processes.

In another aspect, methods and systems that employ multiphoton microscopy in-vivo to generate information regarding mitochondrial organization and dynamics are disclosed. In some embodiments, such methods can be utilized to determine depth dependence of a mitochondrial clustering parameter in in a tissue portion, e.g., the epidermal epithelium, which can in turn be employed as an indicator of a disease condition. As discussed in more detail below, in some embodiments, NAD(P)H imaging can be employed as a label-free approach to monitor the state of mitochondria and its organization in-vivo. More specifically, in many embodiments, two-photon excitation of the NAD(P)H can be used to cause the NAD(P)H to emit fluorescent radiation, which can be detected and analyzed in a manner discussed below to obtain information about the organization and dynamics of mitochondria. In some embodiments, the power spectral density of the fluorescent image can be computed and a parameter indicative of mitochondrial clustering can be extracted from the power spectral density, e.g., via fitting the power spectral density to an inverse power law decay expression. In some such embodiments, prior to the extraction of the mitochondrial clustering parameter, the image can be segmented, e.g., via removal of nuclear and interstitial spaces, and the image signal voids created by such removal can be eliminated by digitally cloning the isolated cytoplasmic intensity fluctuations into the voids.

In one aspect, a method for imaging tissue in-vivo is disclosed, which includes illuminating a portion of a tissue in-vivo with optical radiation (e.g., laser radiation) so as to cause a multi-photon excitation of at least one endogenous chromophore associated with the mitochondria, thereby causing said endogenous chromophore to emit fluorescent radiation, detecting the fluorescence radiation and processing said detected radiation to generate an original (raw) image of the tissue portion, segmenting the image by selecting a plurality of pixels corresponding to a selected cellular structure and masking other pixels in the image. By way of example, the masked pixels can correspond to cells' nuclei and/or interstitial regions between the cells. The pixel intensities of the segmented image can be normalized followed by assigning pixel intensities to the masked pixels via digital object cloning so as to generate a processed image. The power spectral density (PSD) of the processed image can be computed, e.g., via Fourier transform, and the PSD can be employed to extract information about any of biochemical state and/or organization of the cellular structure, e.g., the mitochondria.

In a related aspect, a method for imaging tissue in-vivo is disclosed, which includes focusing radiation (e.g., laser radiation) into a plurality of tissue segments at different depths in-vivo so as to cause a multi-photon excitation of at least one chromophore, e.g., an endogenous chromophore, associated with the cell's mitochondria, thereby causing said endogenous chromophore to emit fluorescent radiation. For each of the illuminated tissue segments, the following procedures can be performed: detecting the fluorescent radiation and processing the detected radiation to generate a raw image of the tissue portion, segmenting the image by selecting a plurality of pixels corresponding to a selected cellular structure and masking other pixels in the image, normalizing pixel intensities in the segmented image, filling intensities of the masked pixels via digital object cloning so as to generate a processed image, and obtaining a Fourier transform of said processed image so as to determine a power spectral density associated with said processed image. The power spectral density of each image can be employed to obtain a mitochondrial clustering parameter associated with each interrogated depth of the tissue. Alternatively, mitochondrial organization information can be extracted using autocorrelation-based algorithms in the spatial domain following the intensity normalization. An example of such auto-correlation algorithms is described in an article entitled "Autocorrelation method for fractal analysis in nonrectangular image domains," published by MacDonald et al. in Optics Letters, vol. 38, issue 21, pp. 4477-4479 (2013), which is herein incorporated by reference in its entirety.

In another related aspect, a method for imaging the epithelium is disclosed. The disclosed method comprises generating a plurality of multi-photon-induced fluorescence images from a plurality of epidermal layers at different depths and processing said images to obtain a parameter indicative of mitochondrial clustering for each of said epidermal depths.

In yet another related aspect, a system for optical assessment of cellular metabolic activity is disclosed. The disclosed system comprises an optical radiation source for generating optical radiation and one or more optical components that direct the optical radiation onto the at least one cell so as to cause multi-photon excitation of at least one metabolic cofactor in the cell. The metabolic cofactor can emit fluorescent radiation in response to the excitation. A detector can detect the emitted fluorescent radiation and generate a signal indicative of the detected fluorescent radiation and an analysis module can operate on the detector signal to provide an assessment of at least one cellular metabolic process.

In other examples, any of the aspects above, or any system, method, apparatus described herein can include one or more of the following features.

The metabolic process can be any process that can directly or indirectly induce a change (e.g., spatially and/or temporally) in the equilibrium of at least one metabolic cofactor. Some examples of such metabolic processes can comprise any of glycolysis, oxidative phosphorylation, glutaminolysis, any of extrinsic and intrinsic mitochondrial uncoupling, fatty acid oxidation, and fatty acid synthesis. Further, the at least one metabolic cofactor can comprise any of NAD(P)H and a Flavin, such as FAD.

In some embodiments, observed changes in the above parameters can be employed to assess the changes in one or more metabolic processes. In some embodiments in which at least two metabolic cofactors are employed, a decrease in the optical redox ratio of the cofactors can be detected. By way of example, the decrease in the redox ratio can correspond to a decrease in the intensity of the fluorescent radiation associated with one cofactor, e.g., FAD, relative to the fluorescent radiation intensity of another metabolic cofactor, e.g., (NAD(P)H). In some embodiments, the observation of such decrease in the optical redox ratio can be employed to assess changes in one or more metabolic processes, as discussed in more detail below. In some embodiments, the observation of an increase in the optical redox ratio can be employed to assess changes in one or more metabolic processes.

In some implementations, the optical radiation can have a wavelength in a range of about 600 nm to about 1400 nm. Further, the fluorescent radiation can have a wavelength in a range of about 400 nm to about 650 nm. Further, the multi-photon excitation can be a two-photon excitation.

Further, in some embodiments, the computer processor can be used to form a fluorescent image of said at least one cell based on said detected fluorescent radiation. By way of example, such an image can include a plurality of pixels each having an intensity indicative of the intensity of fluorescent radiation emanating from a cellular location corresponding to that pixel. The computer processor can be configured to analyze the intensity associated with a plurality of pixels in the formed image to derive the mitochondrial clustering parameter. For example, the computer processor can perform the following steps: segmenting the image by selecting a plurality of pixels corresponding to mitochondria and masking other pixels in the image, normalizing pixel intensities in the segmented image, assigning an intensity for each of the masked pixels via digital object cloning so as to generate a processed image, obtaining a Fourier transform of the processed image so as to determine a power spectral density associated with the processed image, and using the power spectral density to compute the mitochondrial clustering parameter. In some embodiments, the masked pixels can correspond to pixels not associated with the cellular mitochondria. By way of example, the masked pixels can be associated with a nucleus of the cell.

In some embodiments, using the power spectral density can comprise fitting the power spectral density to an inverse power law decay expression for computing the clustering parameter. The fitting of the power spectral density can comprise fitting the power spectral density by the following relation: $R(k)=Ak^{-\beta}$, where k denotes spatial frequency, A is an amplitude parameter, and $\beta$ denotes the mitochondrial clustering parameter.

Further, in some embodiments, the PSD can be employed to compute a mitochondrial clustering parameter. In some such embodiments, the PSD can be fitted to an inverse law decay expression for computing the clustering parameter. For example, the PSD can be fitted to the following relation: $R(k)=Ak^{-\beta}$, where k denotes spatial frequency, A is an amplitude parameter and $\beta$ denotes the mitochondrial clustering parameter.

The cell can be any cell type. Some examples of cell types comprise any of an epithelial cell, a fibroblast, a stem cell, an adipocyte, a myofibroblast, an osteocyte, a keratocyte. For example, in some embodiments, the cell can be a diseased cell. The diseased cell can be, for example, a cancer cell. In some embodiments, at least one cell can be illuminated in vivo. In some embodiments, the present methods and systems are employed to assess metabolic activity of a plurality of cells forming a tissue or an organ, e.g., epithelium such as epidermis.

In some embodiments, one or more filters can be applied to the original image or the processed image to minimize signal contributions to the image from one or more chromophores other than a chromophore of interest, which can enable visualization of the mitochondria. By way of example, such a filter can be Shanbhag's entropy filter. In some embodiments, the endogenous chromophore can be NAD(P)H and the filter can be employed to minimize contributions of any of collagen, elastin, keratin and melanin to the image. It should be understood the present teachings can be employed to process any type of fluorescence image that can provide mitochondrial contrast. In some embodiments, the image can be obtained by detecting fluorescence from endogenous chromophores, such as two-photon-excited fluorescence from NAD(P)H. In other embodiments, a mitochondrial probe, such as a fluorescence dye that stains the mitochondria, can be used, and a single or multi-photon fluorescent image of the probe can be detected and analyzed in accordance with the present teachings to obtain information about the mitochondria.

Further in some embodiments, segmenting the image to isolate regions of interest can include applying at least one bandpass filter to the image. By way of example, the bandpass filter can be generated via combination of two or more high-pass and low-pass Gaussian filters and/or Butterworth filters.

In some embodiments, the imaging methods and systems according to the present teachings can be employed to derive the depth dependence of the mitochondrial clustering parameter, or any combination of the metabolic cofactors disclosed herein (e.g., endogenous NAD(P)H and FAD), e.g., in an epithelial tissue, such as the epithelium, e.g., the epidermis. Such depth dependence of the clustering parameter can in turn be employed to assess whether a disease condition, such as cancer, is present. For example, in healthy epidermal epithelia, the basal and parabasal layers can display high and stable values of the clustering parameter. In particular, as the epithelial cell differentiation progresses from the basal to the higher epidermal layers, the clustering parameter shows declining values, reaching its minimum within the spinous layer (tubular mitochondria). Further, towards the most terminal differentiation state as the granular keratinocytes can enter an apoptotic state to create the stratum corneum, the mitochondrial clustering parameter values start to recover, signifying a return to a more fissioned phenotype.

In some embodiments, the fluorescence images can be generated by focusing an optical radiation (e.g., laser radiation) at a plurality of locations in different depths of the epithelium so as to cause multi-photon excitation of NAD (P)H in one or more cells and induce emission of fluorescent radiation from the excited NAD(P)H. The fluorescent radiation emanating from each of the epidermal depths can be detected and the detected radiation can be processed to generate a plurality of mitochondrial images each corresponding to one of the depths. For each of the images, a mitochondrial clustering parameter corresponding to one of the depths can be extracted. Further, a depth-dependence of the mitochondrial clustering parameter can be utilized to assess whether a disease condition is present in the imaged epithelium.

Other aspects and advantages of the invention can become apparent from the following drawings and description, all of which illustrate the principles of the invention, by way of example only.

BRIEF DESCRIPTION OF THE DRAWINGS

Features and advantages of the invention described herein, together with further advantages, may be better understood by referring to the following description taken in conjunction with the accompanying drawings. The drawings are not necessarily to scale, emphasis instead is generally placed upon illustrating the principles of the invention.

FIGS. 2A-2H schematically illustrate images corresponding to the data used in performing the examples described herein.

FIGS. 4A-4I illustrate examples optical readouts obtained from human foreskin keratinocytes (HFK) under metabolic pathways of glycolysis or glutaminolysis.

FIGS. 5A-1 through 5D-2 illustrate images of raw dataset for HL-1 cells that have been used to produce the images shown in FIGS. 6A-1 through 6F.

FIGS. 6A-1 through 6F schematically illustrate the optical readouts of HL-1 cardiomyocytes in response to chemical uncoupling by carbonyl cyanide m-chlorophenyl hydrazine (CCCP).

FIGS. 8A-1 through 8H-2 illustrate the ex vivo and in vivo raw dataset for brown adipose tissue (BAT) under cold activation that has been used to generate representative images shown in FIGS. 9A-1 through 9O.

FIG. 9A-9O schematically illustrate the ex vivo and in vivo optical readouts of brown adipose tissue (BAT) in response to cold activation.

FIGS. 10A-1 through 10D-3 schematically illustrate images of the raw data for a C2C12 mouse myoblast cell line under metabolic pathway of β oxidation, which are used to arrive at images shown in FIGS. 12A-1 through 12F.

FIGS. 11-1 through 11-3 illustrate fluorescence images of C2C12 cells.

FIGS. 12A-1 through 12F illustrate optical readouts of C2C12 myoblasts under β oxidation induced by supplementing Oleate or Palmitate.

FIGS. 13A-1 through 13D-2 schematically illustrate images of raw datasets for mesenchymal stem cells (MSCs) during lipogenesis.

FIGS. 14A-1 through 14F schematically illustrate images of optical readouts of mesenchymal stem cells (MSCs) during metabolic pathway of lipogenesis.

FIGS. 15A-15F schematically illustrate examples of classifications of metabolic pathways obtained using one or two optical metrics.

FIG. 16 illustrates a table that includes the individual heterogeneity index for optical metrics disclosed herein.

FIGS. 17A-17D-6 schematically illustrate examples of holistic visualization of dataset using optical metrics disclosed herein.

FIG. 20 schematically depicts a system according to some embodiments disclosed herein.

DETAILED DESCRIPTION

Figure 1A:
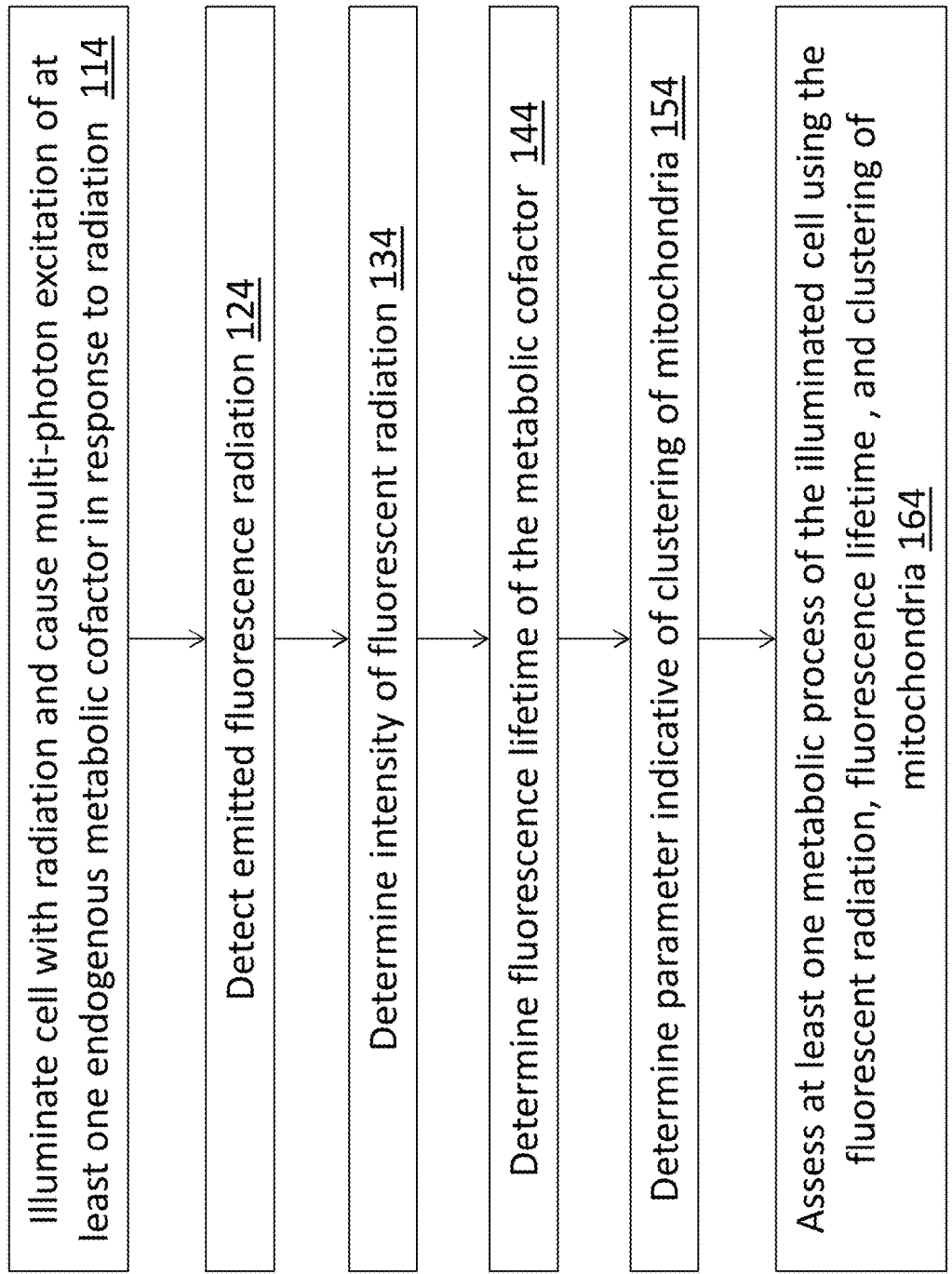
FIG. 1A is a flow diagram of procedures for assessing a cellular metabolic process according to some embodiments disclosed herein.

The embodiments discussed below are illustrative of various aspects of the invention. Although the embodiments are discussed primarily in connection with obtaining information regarding the mitochondria, the present teachings can be applied to obtain information about other cellular structures and/or organelles. The term "about" is used herein to indicate a plus or minus variation of at most 10% around a numerical value. The term "substantially" is used herein to indicate a plus or minus deviation from a complete state or condition by less than 10%.

The present disclosure relates to a quantitative method and corresponding system and apparatus for non-invasively detecting functional and structural metabolic biomarkers, for example by relying on endogenous two-photon excited fluorescence from coenzymes, such as NAD(P)H and FAD.

In some embodiments, a multi-parametric analysis of the cellular redox state is disclosed. Specifically, cellular redox state can be analyzed by relying on NADH fluorescence lifetime and mitochondrial clustering within intact living cells and 3D tissues, which are subjected to metabolic perturbations that trigger changes in distinct metabolic processes, including glycolysis and glutaminolysis, extrinsic and intrinsic mitochondrial uncoupling, fatty acid oxidation and synthesis. These optical biomarkers can be used to obtain complementary information regarding the underlying biological mechanisms. The information obtained from these biomarkers can further be used to achieve sensitive and label-free identification of metabolic processes (e.g., various metabolic pathways), and characterize the heterogeneity of the elicited responses with single cell resolution.

Two-photon excited fluorescence (TPEF) can be a powerful modality for sensitive, quantitative, label-free, and high resolution assessments of metabolic activity and cellular responses both in vitro and in vivo. NAD(P)H and FAD are two key metabolic co-enzymes that are involved in several important metabolic pathways. These metabolic co-enzymes can be used as the sources of optical contrast for many optical metabolic assessments.

Further, the TPEF intensity ratio of these two fluorophores can be used as a metric for determining cellular redox status. Specifically, the optical redox ratio, defined as the TPEF intensity of FAD/(NAD(P)H+FAD) can be highly correlated with mass spectrometry-based assessments of both FAD/(NADH+FAD) and NAD$^+$/(NADH+NAD$^+$). This optical redox ratio can be an indicator that the FAD/TPEF signal is in equilibrium with the cellular NAD$^+$ content. The fluorescence lifetime of NAD(P)H can also be employed as a metabolic indicator metric, since this lifetime can depend on whether NAD(P)H is in its free or bound state. For example, longer characteristic fluorescence lifetimes can vary over approximately 1 to 6 nanoseconds, depending on the specific identity of the complex to which NADH is bound.

These metrics (e.g., intensity ratio and fluorescence lifetime) can also be sensitive to processes and complementary aspects of cellular metabolism. For example, differentiation and apoptosis and changes in the values of these metrics can relate to alterations in the relative levels of oxidative phosphorylation, glycolysis, glutaminolysis, and fatty acid synthesis. Further, when used in combination with one another, these metrics can serve as optical metabolic indices that can be used to more accurately describe cellular metabolism (e.g., more accurately than using a single metric). For example, the intensity and lifetime redox metrics, when used in combination with one another, can be employed to describe metabolic responses of cancer spheroids to different treatment regimens.

FIG. 1A is a flow diagram 100 of procedures for assessing a metabolic process according to some embodiments disclosed herein. As shown in FIG. 1A, in some embodiments disclosed herein a cellular metabolic process can be assessed by illuminating at least one cell with optical (e.g., laser) radiation so as to cause multi-photon (e.g., two-photon) excitation of at least one endogenous metabolic cofactor in the illuminated cell, thereby causing the excited metabolic cofactor to emit fluorescent radiation 114.

In some embodiments, the illuminating laser radiation can have a wavelength, for example, in a range of about 600 nanometers (nm) to about 1400 nm, though other wavelengths can also be employed. In some embodiments, the wavelength of the emitted fluorescent radiation can be in a range of about 400 nm to about 650 nm, e.g., in a range of about 400 nm to about 600 nm.

A detector can be used to detect the fluorescent radiation emitted by the excited metabolic cofactors 124. The fluorescent radiation emitted by the excited metabolic cofactor can be detected using any suitable detector. A variety of photodetectors can be employed for detecting the emitted fluorescent radiation. By way of example, one or more photomultiplier tubes can be employed to detect the fluorescent radiation emitted by the metabolic cofactor. In some embodiments, appropriate filters can be employed to distinguish the fluorescent radiation emitted by two or more metabolic cofactors.

In some embodiments, the detected fluorescent radiation emitted by the metabolic cofactors can be used to determine the following parameters 1) the intensity of fluorescent radiation 134, 2) a fluorescence lifetime of the metabolic cofactor 144, and 3) a parameter indicative of mitochondrial clustering in the cell 154. In some embodiments, the fluorescent intensity is determined as a function of the intensities of pixels in a fluorescent image of the cell. For example, the fluorescent intensity can be determined based on the average fluorescent intensities of the NAD(P)H and FAD from the pixels within the field of view. In some embodiments, a sum or a function of the sum of the intensities of pixels in a fluorescent image of the cell can be used. These parameters can be used to access at least one metabolic process of the illuminated cell 164. For example, as described in further details below, observed changes in these parameters can be correlated to a change (e.g., an enhancement or reduction) in the activity of a metabolic process. In some embodiments, the use of these three optical parameters (herein also referred to as optical indices) together, rather than one or two of them in isolation, can result in unambiguously assessing the activity of a metabolic process.

Figure 1B:
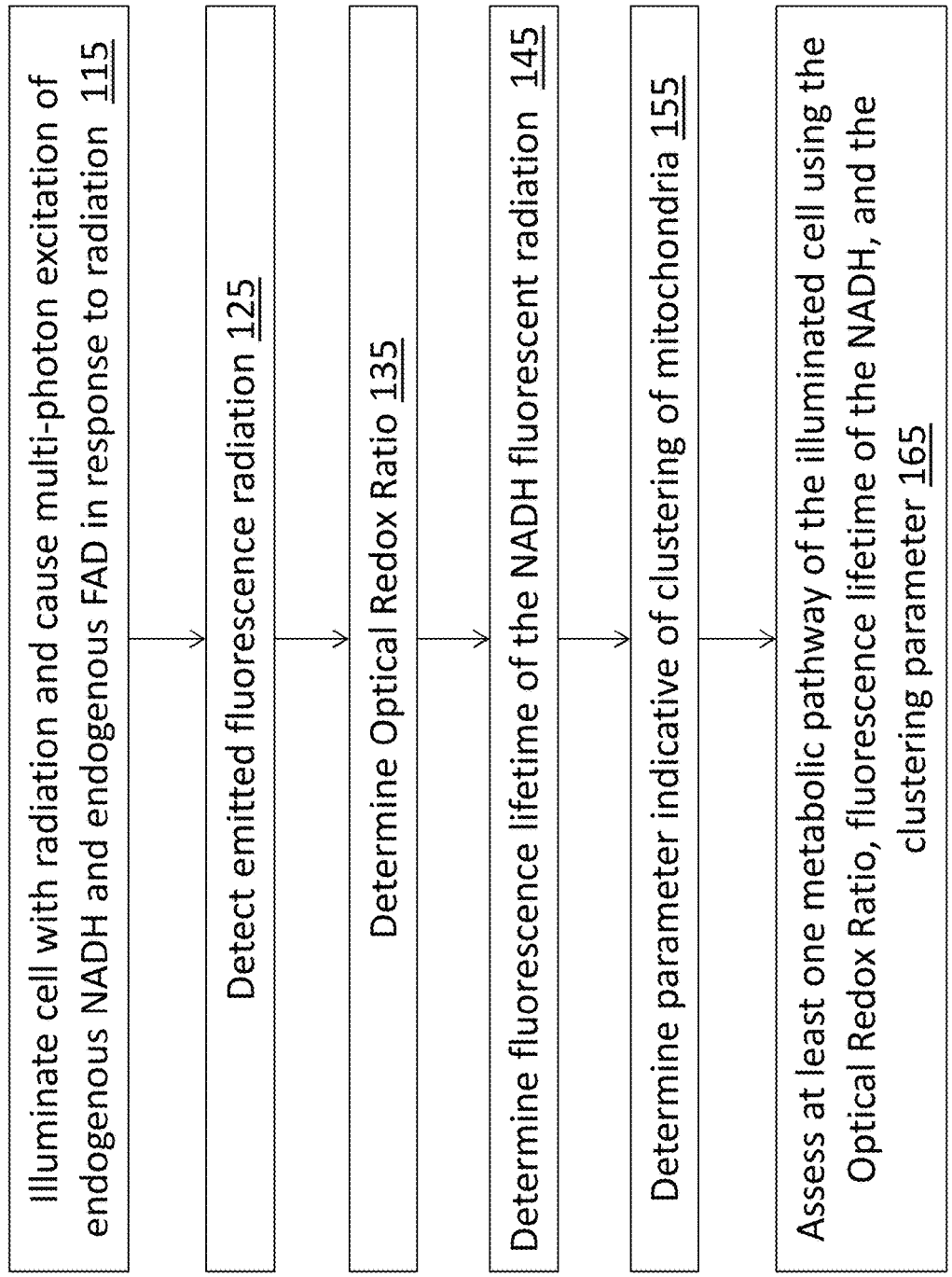
FIG. 1B is a flow diagram of procedures for assessing a cellular metabolic activity according to some embodiments disclosed herein.

FIG. 1B is a flow diagram 100' of procedures for assessing cellular metabolic activity according to some embodiments disclosed herein. As shown in FIG. 1B, in some embodiments disclosed herein cellular metabolic activity can be assessed by illuminating at least one cell with laser radiation so as to cause multi-photon (e.g., two-photon) excitation of endogenous NAD(P)H and endogenous FAD in the illuminated cell, thereby causing said excited NAD(P)H and FAD to emit fluorescent radiation 115.

This fluorescent radiation is herein referred to as "two-photon excited fluorescence." In some embodiments, a tissue can be illuminated in vivo so as to excite, via multi-photon excitation, endogenous NAD(P)H and FAD in one or more cells of the tissue. In some other embodiments, one or more cells can be illuminated ex vivo so as to cause multi-photon excitation of endogenous NAD(P)H and FAD present in those cells.

In some embodiments of the above methods, the illuminating laser radiation can have a wavelength, for example, in a range of about 600 nm to about 1400 nm nanometer (nm), though other wavelengths can also be employed. In some embodiments, the wavelength of the emitted fluorescent radiation can be in a range of about 400 nm to about 650 nm, e.g., in a range of about 400 nm to about 600 nm.

A detector can be used to detect the fluorescent radiation emitted by the excited NAD(P)H and FAD 125. The fluorescent radiation emitted by the excited NAD(P)H and FAD can be detected using any suitable detector. A variety of photodetectors can be employed for detecting the emitted fluorescent radiation. By way of example, one or more photomultiplier tubes can be employed to detect the two-photon excited fluorescence emitted by the NAD(P)H and FAD. In some embodiments, appropriate filters can be employed to distinguish the two-photon excited fluorescence emitted by NAD(P)H from that emitted by FAD.

The intensities of the detected two-photon excited fluorescence emitted by the NAD(P)H and FAD can be used to determine an optical redox ratio 135. For example, the optical redox ratio can be determined according to the following relation:

$$ORR = \frac{I_{FAD}}{I_{NAD(P)H} + I_{FAD}},$$

where ORR denotes the optical redox ratio, $I_{NADH}$ and $I_{FAD}$ denote, respectively, the two-photon excited fluorescence intensities associated with NAD(P)H and FAD. In other embodiments, the optical redox ration can be calculated as a ratio of the fluorescence intensity of NAD(P)H relative to the fluorescence intensity of FAD. In general, an optical redox ratio of two metabolic cofactors is indicative of a ratio (e.g., a direct or a normalized ratio) of the fluorescent intensities of those cofactors.

Further, the temporal variation of the two-photon excited fluorescence emitted by NAD(P)H can be used to determine the fluorescence lifetime of the NAD(P)H fluorescent radiation 145. For example, in some embodiments, the fluorescence lifetime can be fit using an exponential decay function. The simplest decay model is a single exponential function, which can be described by a single decay time. In many cases, however, the decay profiles can be modeled by sums multiple, e.g., two or three, exponential functions. By way of example, a decay function F(t) can be defined as follows where $a_i$ denotes the amplitude coefficient of each function and $\tau_i$ denotes the decay time associated with the $i^{th}$ decay function:

$$F(t) = \sum_{i=1}^{n} a_i e^{-\frac{t}{\tau_i}}, n \geq 1$$

Furthermore, the two-excited fluorescence radiation emitted by NAD(P)H can be employed, e.g., in a manner discussed in more detail below, to obtain a parameter indicative of clustering of the cell's mitochondria 155. By way of example, in some embodiments, the NAD(P)H fluorescent radiation can be used to generate a fluorescent image of the illuminated cell(s). For example, as discussed in more detail below, a spatial Fourier transform of the fluorescent image can be obtained to determine a power spectral density associated with the processed image, and the power spectral density can be employed to compute a mitochondrial clustering parameter. In some embodiments, the fluorescent radiation from FAD can be used in a similar manner to compute a mitochondrial clustering parameter.

With continued reference to the flow diagram of FIG. 1B, the above three parameters, namely, (1) the optical redox ratio, (2) the fluorescence lifetime associated with NAD(P)H, and (3) the mitochondrial clustering parameter, can be used to assess at least one metabolic process (e.g., a metabolic pathway) of the illuminated cell 165. For example, observed changes in these parameters can be correlated to a change (e.g., an enhancement or reduction) in the activity of a metabolic pathway. In some embodiments, the use of these three optical parameters (herein also referred to as optical indices) together, rather than one or two of them in isolation, can result in unambiguously assessing the activity of a metabolic pathway.

By way of example, the above three optical parameters can be employed to assess glycolysis, oxidative phosphorylation, glutaminolysis, any of extrinsic and intrinsic mitochondrial uncoupling, fatty acid oxidation and fatty acid synthesis processes. For example, a concurrent reduction in the optical redox ratio, an decrease in the fluorescence lifetime of the NAD(P)H, and an increase in mitochondrial clustering parameter can indicate an increase in the glycolysis level. Thus, in some embodiments, the above three optical parameters can be used to identify relative changes in the levels of glycolysis and oxidative phosphorylation.

In some embodiments, the above parameters can be employed to assess fatty acid synthesis process. For example, a concurrent decrease in the optical redox ratio, an increase in the fluorescence lifetime of the NADH, and an increase in mitochondrial clustering can indicate an increase in fatty acid synthesis.

In some embodiments, the combined use of the above three optical parameters can be advantageous in that it can allow unambiguously identifying changes in a metabolic process, which may not be feasible if only one or two of the above parameters were to be utilized. For example, both enhanced glycolysis and fatty acid synthesis can lead to a decrease in the optical redox ratio and an increase in mitochondrial clustering. As such, if one were to utilize only these two parameters, one could not unambiguously correlate a decrease in the optical redox ratio and an increase in mitochondrial clustering to enhanced glycolysis or fatty acid synthesis. However, NAD(P)H fluorescence lifetime can decrease for enhanced glycolysis and can increase for enhanced fatty acid synthesis. Thus, the use of the NAD(P)H fluorescence lifetime together with the optical redox ratio and the mitochondrial clustering parameter can allow the unambiguous identification of enhanced glycolysis relative to enhanced fatty acid synthesis.

Figure 1C:
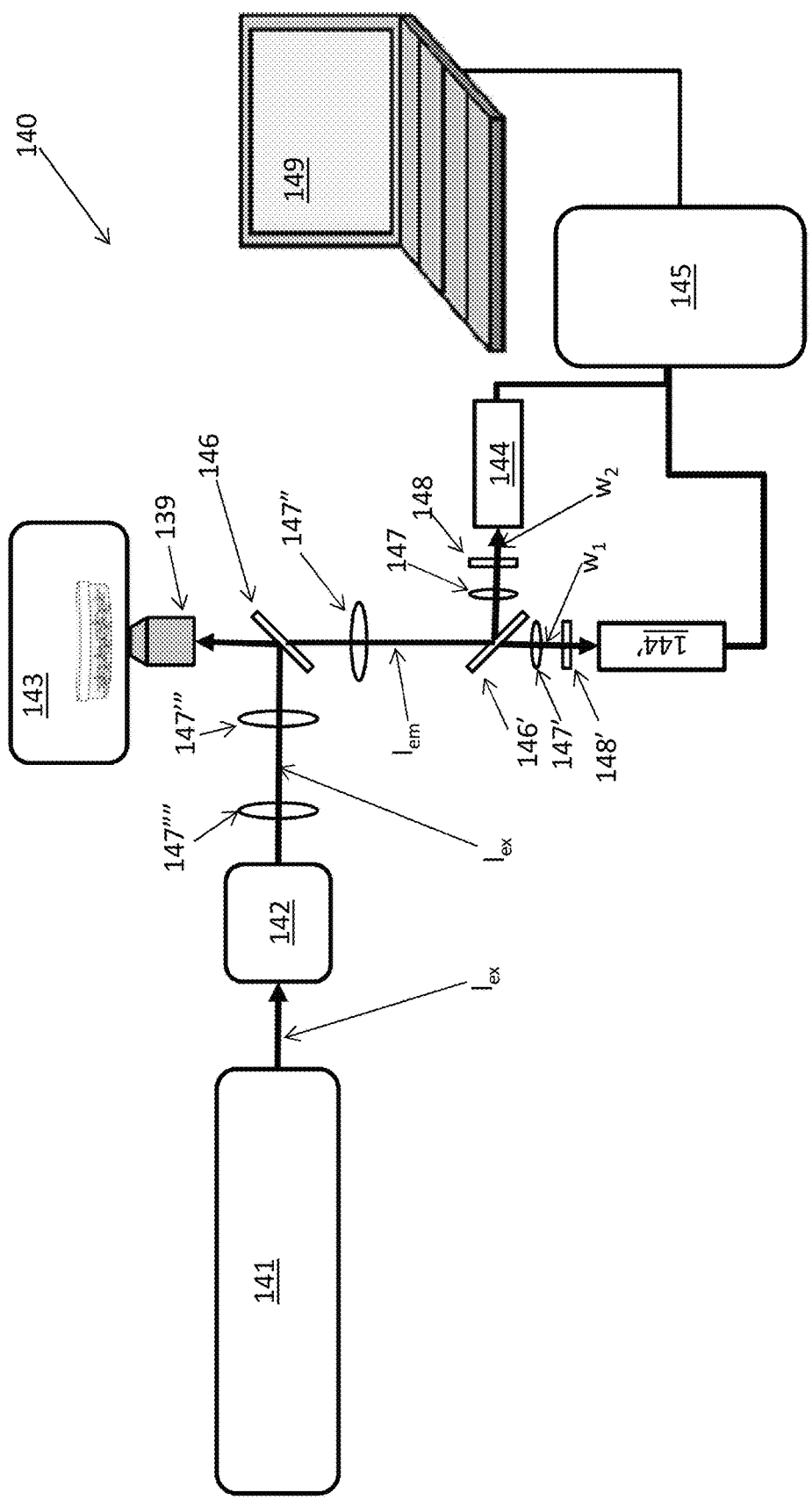
FIG. 1C schematically illustrates a system for assessing one or more metabolic processes.

FIG. 1C schematically depicts a system 140 according to an embodiment for assessing one or more metabolic pathways. The system 140 includes an excitation source 141, such as a laser generator that provides the required radiation (e.g., laser radiation, excitation beam $l_{ex}$) for illuminating a sample, e.g., tissue in vivo. In some embodiments, the source 141 can generate radiation (for example, laser beams) having a wavelength in a range of about 600 nm to about 1400 nm. The excitation beams $l_{ex}$ generated by the excitation source 141 can be forwarded to a scanner 142. The scanner 142 can be any suitable scanner. For example, the scanner 142 can be a scanner that scans the excitation/laser beams emitted by the excitation source 141 along horizontal (x) and vertical (y) directions to ensure that the excitation beams $l_{ex}$ are incident at desired/selected locations on the sample or specimen. The system can further include an objective lens 139 that is configured to focus the excitation beams $l_{ex}$ from the source 141 onto an object plane (not shown). The object plane can lie on, or in, a specimen or target material 143. The system can also include other elements generally used in a two-photon microscopy system, such as lenses 147, 147', 147'', 147''', 147'''', dichroic mirrors 146, 146', and bandpass filters 148, 148'. These elements (e.g., lenses, dichroic mirrors, and filters) can be generally responsible for directing the excitation beam $l_{ex}$ onto the sample or specimen 143 and directing/forwarding the radiation emitted by the sample $l_{em}$ onto the detectors 144, 144'. Generally, the excitation source 141, the scanner 142, the objective filter 139, the lenses, dichroic mirrors, and filters can be any suitable element of that kind used in any suitable or available two-photon laser microscopy system.

The excitation beams $l_{ex}$ emitted from the excitation source, once incident on the sample 143, can illuminate the sample with optical radiation. The illumination of the sample 143 with the excitation beam $l_{ex}$ can, in turn, cause multi-photon excitation of endogenous NAD(P)H and FAD in at least one radiated cell in the sample 143. The excitation of the endogenous NAD(P)H and FAD causes these elements to emit fluorescent radiation. The emitted radiation $l_{em}$ can be directed through the dichroic mirror 146 and lens 147''. The emitted radiation $l_{em}$ can be separated, for example by the use of a dichroic mirror 146', and divided based on wavelength and directed to respective detectors 144, 144' using for example, one or more lenses 147, 147' and one or more filters (e.g., bandpass filters) 148, 148'. Specifically, in some embodiments, the emitted radiation beam $l_{em}$ can be divided, for example using a beam splitter or a dichroic mirror 146', into two portions. Each portion of the emitted beam can further be filtered such that one portion $w_1$ of the emitted beam $l_{em}$ corresponds the fluorescent radiation emitted by endogenous FAD and another portion $w_2$ of the emitted beam $l_{em}$ corresponds the fluorescent radiation emitted by endogenous NAD(P)H.

The separation of the portions of the emitted beam $l_{em}$ can be done using any suitable technique, for example by using a bandpass filter 148, 148'. The bandpass filter 148, 148' can be configured to filter the emitted beam $l_{em}$ such that only the portion of the emitted beam $l_{em}$ that corresponds to a specific/desired frequency (e.g., frequencies corresponding to fluorescent radiation emitted by endogenous FAD or fluorescent radiation emitted by endogenous NAD(P)H) is passed through and forwarded to the corresponding detector 144, 144'.

As shown in FIG. 1C, the emitted beam $l_{em}$ can be divided, using a dichroic mirror 146', into two portions and each portion can be filtered using a corresponding filter 148, 148'. Specifically, a first portion of the emitted beam $l_{em}$ can be filtered using a bandpass filter 148' to remove all frequencies of the radiation other than the frequencies corresponding to fluorescent radiation emitted by endogenous FAD. This portion of the frequencies $w_1$ of the emitted beam $l_{em}$ can be forwarded to a detector 144'. Similarly, a second portion of the emitted beam $l_{em}$ can be filtered using a bandpass filter 148 to remove all frequencies of the radiation other than the frequencies corresponding to fluorescent radiation emitted by endogenous NAD(P)H. This portion of the the emitted beam $l_{em}$ is forwarded to another detector 144. The detectors 144, 144' can detect the fluorescent radiation emitted by the excited NAD(P)H and FAD. A time-correlated single photon counting (TCSPC) system 145 can be used to determine the TPEF FAD and NAD(P)H decay characteristics (i.e., lifetime) and the corresponding integrated intensity of the detected FAD and NAD(P)H beams.

An analyzer 149 can analyze the fluorescent radiation, as detailed below, to determine factors for assessing at least one metabolic process of the cells (i.e., the at least one radiated cell) in the sample 143. For example, the analyzer can determine the following parameters: (1) an optical redox ratio of NAD(P)H and FAD, (2) a fluorescence lifetime of NAD(P)H, and (3) a parameter indicative of mitochondrial clustering in the cell. These parameters can be used to determine at least one metabolic process of the at least one cell in the sample 143. The analyzer can be implemented in hardware, software and/or firmware in a manner known in the art and in accordance with the present teachings. For example, the analyzer can include a processor, one or more memory modules for storing data and/or instructions (e.g., instructions for implementing the methods described herein) and one or more communications buses for connecting various components of the analyzer, among other elements.

Figure 1D:
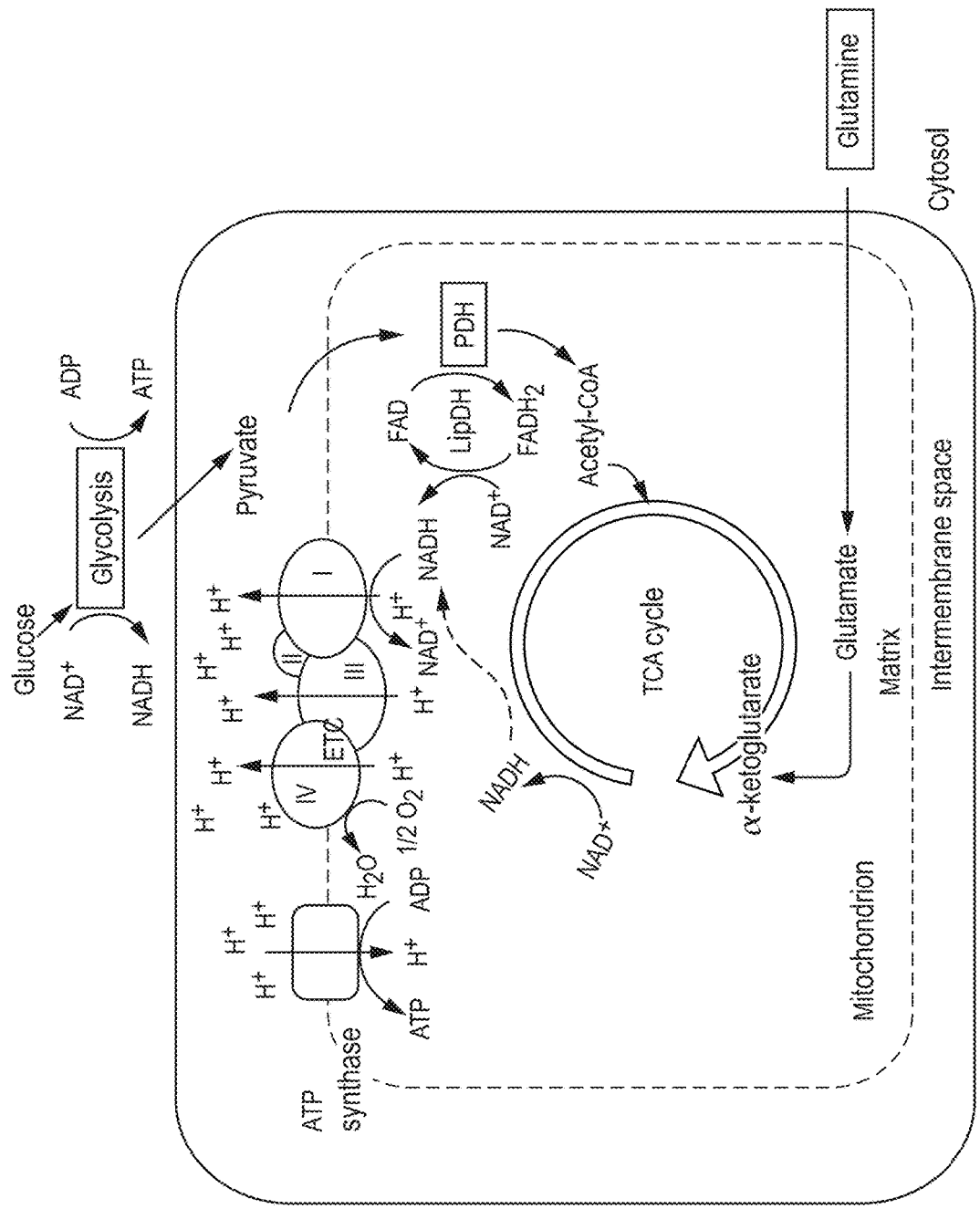
FIGS. 1D-1F schematically illustrate examples of changes in NADH and FAD concentrations due to changes in metabolic processes.
Figure 1E:
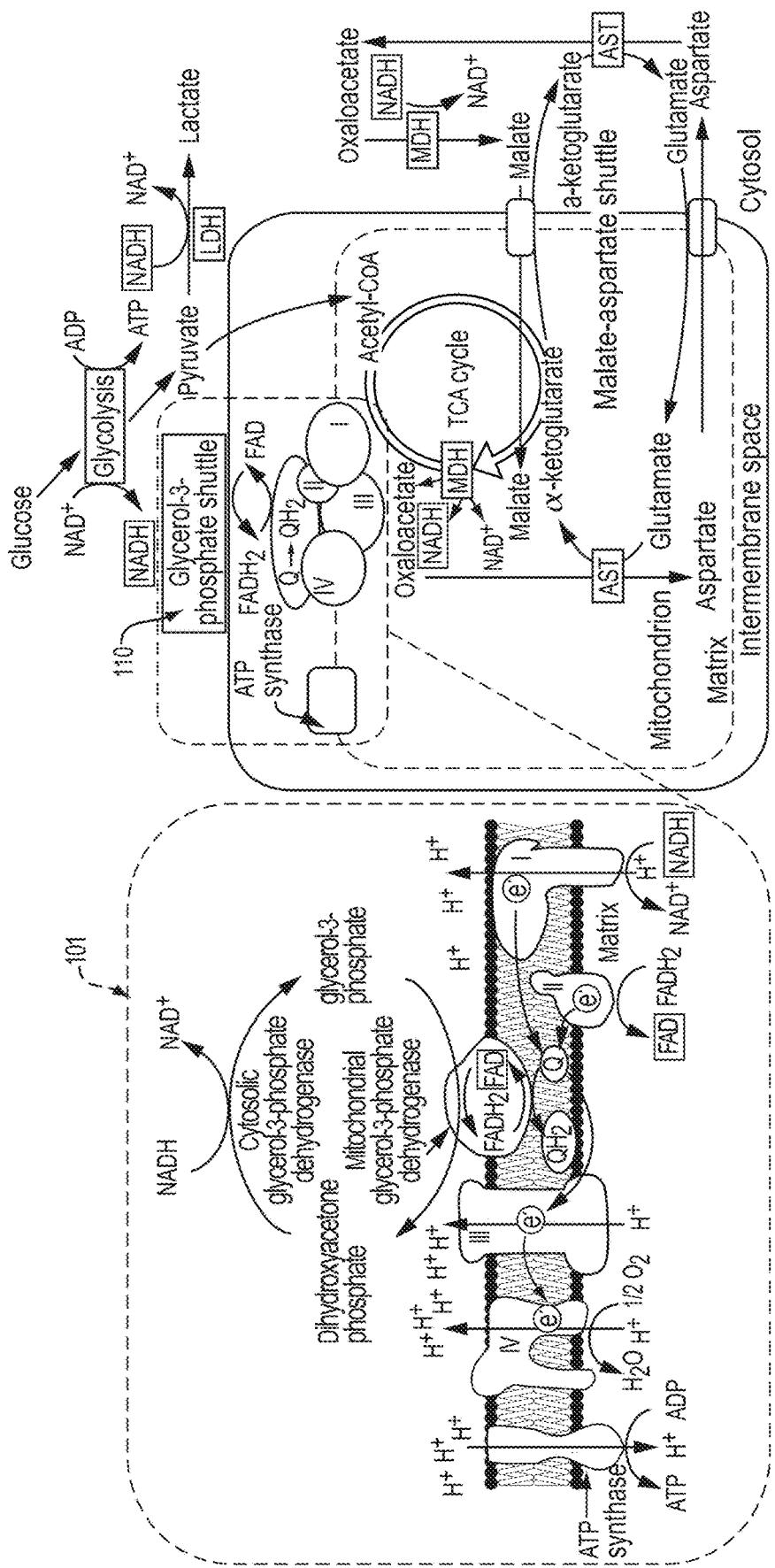
Figure 1F:
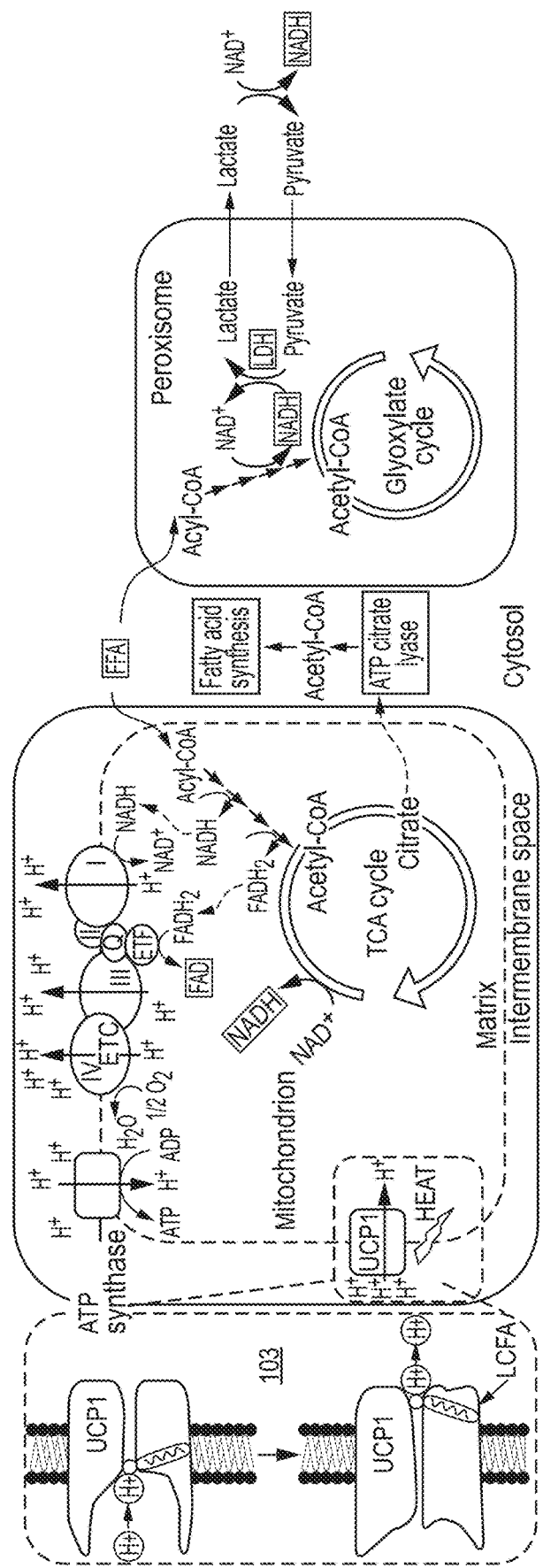

FIGS. 1D-1F schematically illustrate examples of changes in NADH and FAD concentrations due to changes in metabolic pathways. For example, the pathways depicted in FIG. 1D, are mainly affected during hypoxia and glucose starvation. In this example, PDH denotes pyruvate dehydrogenase, LipDH denotes lipoamide dehydrogenase, ETC denotes electron transport chain, and TCA denotes tricarboxylic acid. In FIG. 1E pathways involved in utilizing the cytosolic NADH reducing power for ATP production are illustrated. Specifically, the glycerol-3-phosphate shuttle 110 and electron flow complexes (zoomed in and surrounded by box 101) are shown. In FIG. 1E, MDH denotes malate dehydrogenase, AST denotes aspartate transaminase, and LDH denotes lactate dehydrogenase. In FIG. 1F, pathways focusing on fatty acid β-oxidation and fatty acid synthesis are shown. In FIG. 1F, UPC1 denotes uncoupling protein 1 (shown in zoomed in form in box 103), LCFA denotes long-chain fatty acid, FFA denotes free fatty acid, and ETF denotes electron transport flavoprotein. By way of example, the methods and systems according to the present teachings can be employed to assess the activities of the above metabolic pathways.

As noted above, one of the parameters employed herein for assessing the activity of a metabolic pathway is a parameter that is indicative of the degree of mitochondrial clustering. Mitochondrial clustering can be extracted as a quantitative metric of mitochondrial organization, e.g., based on an automated analysis of NAD(P)H TPEF images. This biomarker can be sensitive to the ability of mitochondria to dynamically fuse and fission, throughout the life of a cell, to optimize energy production and distribution or to protect the cell from insult. Specifically, mitochondrial clustering can increase when glycolytic metabolism increases during proliferation and when mitochondria assume more fragmented phenotypes. Conversely, mitochondrial clustering can decrease when the rate of glutaminolysis increases and fused mitochondrial networks become more prevalent (as shown in FIG. 1D).

Embodiments disclosed herein can employ mitochondrial clustering in vivo and/or ex vivo to assess at least one metabolic process of the cell. For example, mitochondrial clustering can be used to characterize dynamic changes in mitochondrial organization in human tissues in vivo, and in response to perturbations such as hypoxia and reperfusion. Mitochondrial clustering can also be employed to reveal highly reproducible depth-dependent variations within the human skin epithelia of healthy subjects. These depth-dependent variations can correspond to distinct levels of cellular differentiation and expression of DRP1 and hFis1, which can play a key role in the orchestration of mitochondrial fission. Cancer (e.g., melanoma and basal cell carcinoma) can abrogate these depth-dependent variations, likely as a result of the metabolic changes that it invokes.

Accordingly, a wealth of highly sensitive, quantitative, structural and functional metabolic information can be extracted from analysis of endogenous TPEF images that are intimately related to cellular function. However, a key limitation of implementing each one of these approaches independently is that they can provide narrow insight regarding the specific metabolic perturbation that leads to the change of the reported optical metabolic metric. For example, a lower redox ratio may be the result of either enhanced glycolysis or fatty acid synthesis.

In order to overcome these difficulties, some embodiments described herein employ effects of specific metabolic perturbations on two or more optical parameters (e.g., the optical redox ratio, the NAD(P)H fluorescence lifetime, and mitochondrial clustering) to obtain information regarding metabolic functions of the cells. For example, in some embodiments, the effects of glycolysis and glutaminolysis, extrinsic and intrinsic mitochondrial uncoupling, fatty acid synthesis, and/or fatty acid oxidation on two or more (and typically all) of the above optical parameters are employed to obtain information pertaining to metabolic functions of the cells. Since glycolysis and glutaminolysis, extrinsic and intrinsic mitochondrial uncoupling, fatty acid synthesis, and/or fatty acid oxidation are pathways that can be implicated in a wide range of pathologies, changes detected in the combination of two or more of these three metabolic metrics can provide unique complimentary insights and high classification accuracy on the specific type of metabolic perturbation experienced by the cells examined.

As described in more details below, the combined use of two or more of these optical metabolic metrics can serve as an important resource for detecting both functional and structural information related to metabolism in a sensitive and quantitative manner. Such information can, in turn, lead to critically important insights regarding the metabolic pathways involved in the development of numerous diseases, with metabolic involvement and the identification of new and effective therapeutic targets.

By way of example, enhanced glycolysis and glutaminolysis can elicit opposite changes in the biochemical and structural optical metabolic readouts. Changes in the balance between the relative levels of glycolysis and oxidative phosphorylation can constitute a prevalent cellular metabolic adaptation, not only in response to changing oxygen conditions, but also in response to changing biosynthetic and proliferative needs. Hypoxia and glucose starvation are two examples of metabolic perturbations that can have well-defined and opposite effects in those metabolic pathways. Hypoxia can selectively inhibit oxidative phosphorylation and enhance glycolytic flux, whereas glucose starvation can elicit the reverse effect.

FIGS. 2A-2H schematically illustrates images corresponding to the data used in performing the examples described herein. Specifically, FIG. 2A illustrate a raw NADH fluorescent image obtained by exciting cellular NADH with laser radiation at a wavelength of 755 nm, FIG. 2B illustrates a raw FAD fluorescent image obtained by exciting cellular FAD with laser radiation at a wavelength of 860, and FIG. 2C illustrates a redox ratio map acquired from NADH (FIG. 2A) and FAD images (FIG. 2C).

FIG. 2D illustrates a phasor plot showing the clustering of pixels of an NADH image, according to the time decay at each pixel. As used herein, the term "phasor plot" refers to a graphical representation of the fluorescence intensity decay curve. The horizontal (x) and vertical (y) axes represent the real (letter "g" in FIG. 2D) and imaginary (letter "s" in FIG. 2D) parts of the Fourier transform of the decay curve.

Generally, the phasor of a mono-exponential decay can be represented by a point on the universal semi-circle, with 0 and infinite lifetimes represented by the points with (1,0) and (0,0) coordinates, respectively. For example, for a bi-exponential decay, the phasor plot, shown in FIG. 2D, can be represented by a point within a semi-circle 199. The phasors depicting the decay rates of many pixels within a field typically form an ellipse, whose major axis traverses the circle at the two points that represent the free (short) and bound (long) NADH lifetimes, and its centroid (i.e., the centroid of the ellipsoid) provides an estimate of the intensity fraction of NADH found in bound form.

FIG. 2E illustrates a NADH bound fraction map acquired from the phasor analysis. FIG. 2F illustrates the binary mask of an NADH image, in which the cytoplasm region of cells are selected. FIG. 2G illustrates the clone stamped image of the NADH intensity signals within binary mask shown in FIG. 2F. FIG. 2H illustrates the Power Spectral Density (PSD) curve of the clone stamped image along with fitting curve. The scale bar used for the plots shown in FIGS. 2A-2H is 30 μm.

FIGS. 3A-1 through 3D-3 illustrate images of the raw data, for Human Foreskin Keratinocyte (HFK) cells under metabolic pathways of glycolysis or glutaminolysis, which have been used to arrive at the results presented below in FIGS. 4A through 4H-3. Specifically, FIGS. 3A-1, 3A-2, 3A-3 illustrate raw NADH fluorescence images obtained from illuminating cellular NADH present in normal media, low oxygen (O$_2$), and no glucose HFK cells with laser radiation at a wavelength of 755 nm.

Figures 1, 3A:
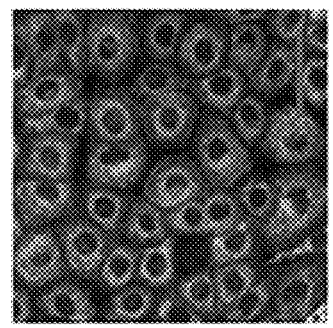
FIGS. 3A-1 through 3D-3 illustrate images of the raw data, for Human Foreskin Heratinocyte (HFK) cells under metabolic pathways of glycolysis or glutaminolysis, which have been used to arrive at the results presented below in FIGS. 4A through 4I.
Figures 2, 3A:
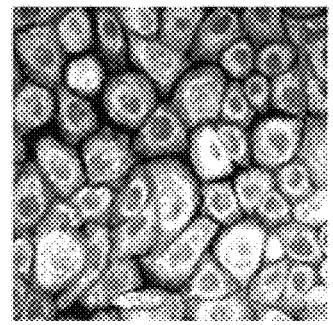
Figures 3, 3A:
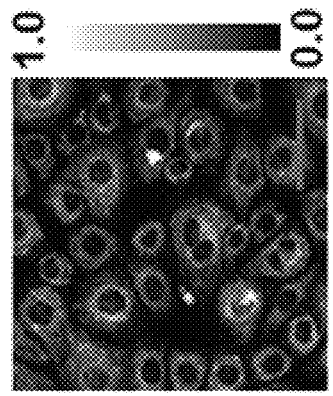
Figures 1, 3B:
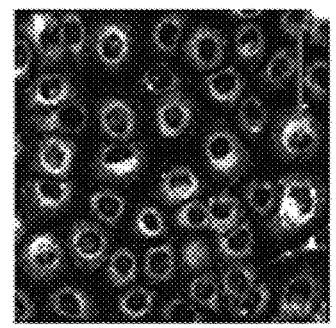
Figures 2, 3B:
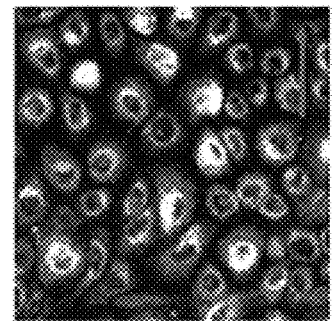
Figures 3, 3B:
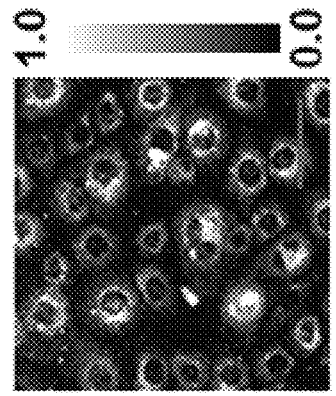
Figures 1, 2, 3, 3C:
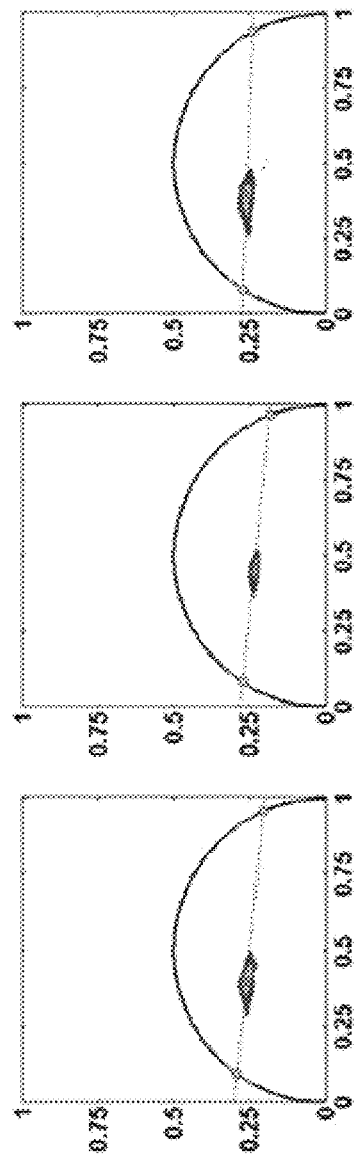
Figures 3, 3D:
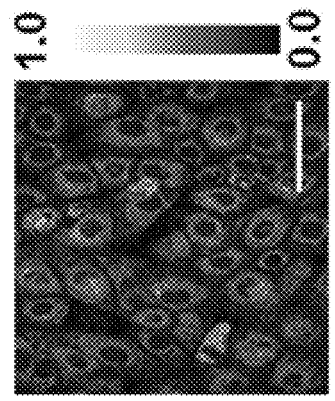
Figures 2, 3D:
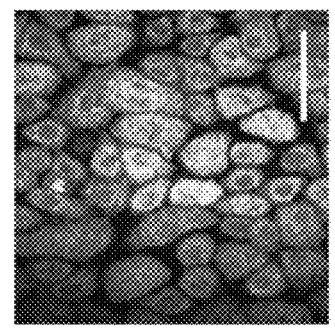
Figures 1, 3D:
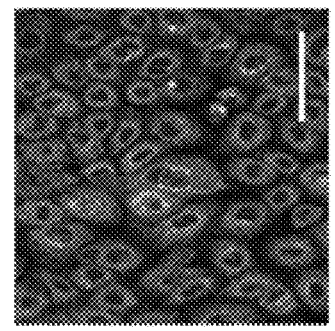

FIGS. 3B-1, 3B-2, 3B-3 illustrate raw FAD fluorescence images used to generate redox ratio map under normal media, low oxygen (O$_2$), and no glucose conditions, respectively. Specifically, FIGS. 3B-1 through 3B-3 are obtained from illuminating cellular FAD present in normal media, low oxygen (O$_2$), and no glucose HFK cells with laser radiation at a wavelength of 860 nm.

FIGS. 3C-1, 3C-2, 3C-3 illustrate phasor plots showing the clustering of pixels in the real-imaginary (g-s) plane under normal media, low oxygen (O$_2$), and no glucose conditions, respectively. FIGS. 3D-1, 3D-2, 3D-3 illustrate raw NADH images corresponding to the clone stamped mitochondria images shown later in FIG. 4H under normal media, low oxygen (O$_2$), and no glucose conditions, respectively. The scale bar used for producing FIGS. 3A-1 through 3D-3 is 50 μm.

Figure 4C:
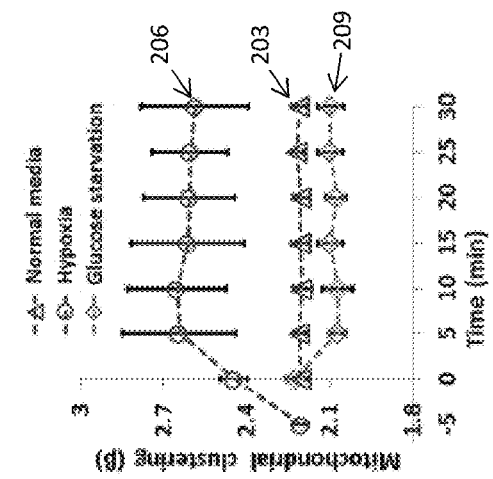
Figure 4B:
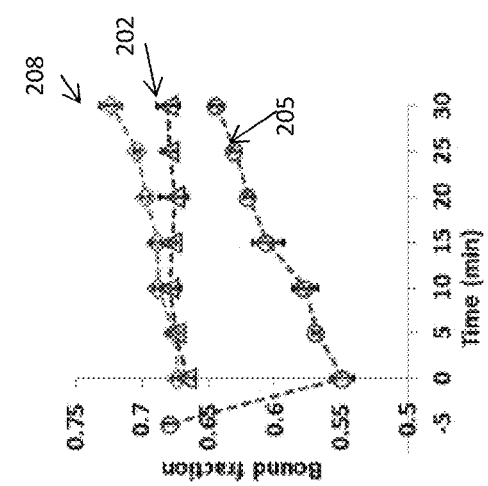
Figure 4A:
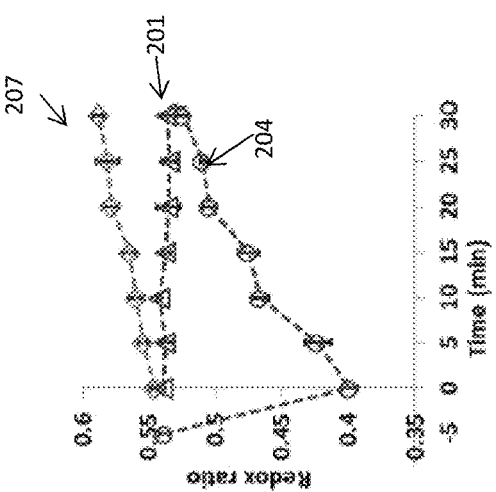

FIGS. 4A-4I illustrate examples of optical readouts obtained from human foreskin keratinocytes (HFK) under metabolic pathways of glycolysis or glutaminolysis. As noted above, the raw data shown in FIGS. 3A-1 through 3D-3 are used to generate the results shown in FIGS. 4A-4I. Specifically, FIGS. 4A-4C illustrate dynamic changes of redox ratio (FIG. 4A), bound NADH fraction (FIG. 4B), and mitochondrial organization (FIG. 4C) during the first thirty minutes after treatment. The data shown in FIGS. 4A-4C corresponds to data obtained from HFK cells under normal media conditions 201 (FIG. 4A), 202 (FIG. 4B), 203 (FIG. 4C), data obtained under low oxygen (O$_2$) (i.e., hypoxia) 204 (FIG. 4A), 205 (FIG. 4B), 206 (FIG. 4C), and data obtained under no glucose (i.e., glucose starvation) 207 (FIG. 4A), 208 (FIG. 4B), 209 (FIG. 4C).

The results shown in FIGS. 4A-4I are obtained by exposing primary human foreskin keratinocytes (HFKs) to transient hypoxia by, for example, changing the media in which the cells are normally cultured with media that is nitrogen bubbled for six hours. Images, specifically NADH TPEF images, can be captured at 755 nm excitation with a non-descanned photomultiplier tube (PMT) that is placed, for example behind a 460±20 nm bandpass filter, and attached to a time-correlated single photon counting (TCSPC) electronics module. In this manner, both the TPEF NADH decay characteristics (i.e., lifetime) and the corresponding integrated intensity can be captured. Images, namely FAD TPEF images, can be recorded at 860 nm excitation using a 525±25 nm bandpass filter. The optical redox ratio can be calculated for each pixel as the FAD/(NADH+FAD) TPEF intensity. In other embodiments, the optical redox ratio can be calculated as FAD/NADH or alternatively as NADH/FAD. Generally, the optical redox ration is indicative of the relative fluorescent intensities of at least two metabolic cofactors.

FIGS. 4D-1, 4D-2, and 4D-3 illustrate representative maps of redox ratio under normal media conditions, hypoxia, and glucose starvation, respectively. FIG. 4E illustrates the means 210, 211, 212 and standard deviations 213, 214, 215 of the redox ratio for cells under normal media conditions, cells evaluated under hypoxia, and cells evaluated under glucose starvation, respectively. FIGS. 4F-1, 4F-2, and 4F-3 illustrate representative maps of bound NADH fraction under normal media conditions, hypoxia, and glucose starvation, respectively. FIG. 4G illustrates the means 216, 217, 218 and standard deviations 219, 220, 221 of the bound NADH fraction for cells under normal media conditions, cells evaluated under hypoxia, and cells evaluated under glucose starvation, respectively. FIGS. 4H-1, 4H-2, and 4H-3 illustrate representative maps of clone stamped mitochondria under normal media conditions, hypoxia, and glucose starvation, respectively. FIG. 4I illustrates the means 222, 223, 224 and standard deviations 225, 226, 227 of mitochondrial clustering for cells under normal media conditions, cells evaluated under hypoxia, and cells evaluated under glucose starvation, respectively. The data obtained under hypoxia treatment conditions (FIGS. 4D-2, 4F-2, and 4H-2) are collected immediately after hypoxia exposure. As shown, the significance symbols (**) on FIG. 4G, and 2I reveal significant differences compared with the normal media treatment shown in FIG. 4E. Here, n=4 cultures/group, scale bar=50 µm, *, p<0.05, **, p<0.01.

While both NADH and NAD(P)H can contribute to the signal that is attributed to NADH, mass spectrometry results indicate that there can be negligible levels of NADPH in these cells, under these conditions. Also, mass spectroscopy results indicate that the optical redox ratio can be highly correlated with the corresponding ratio assessed based on the corresponding concentrations of NADH and FAD. The optical redox ratio can drop significantly and immediately upon introduction of the cells to the hypoxic media and it can increase gradually while the oxygen content in the media increases, as it diffuses from the micro-incubator environment. Redox ratio values acquired over identical timescales from control cultures can be very stable, demonstrating that the observed changes can be due to hypoxia (FIG. 4A).

Based on the raw NADH and FAD images (FIGS. 3A-1, 3B-1), representative redox ratio maps from cells exposed to normal and hypoxic media (e.g., immediately after hypoxia exposure) are shown in FIGS. 4D-1 and 4D-2. As shown in FIG. 4D-2, cells exposed to hypoxia can have a lower redox ratio compared to the cells under normal media conditions. An example of this significant decrease in the redox ratio is quantified in FIG. 4E, based on four independent experiments. The decrease in redox ratio is accompanied by a corresponding decrease in the bound NADH fraction (as shown in FIG. 4B), as quantified from the phasor-based analysis of the NADH TPEF lifetime data. This can provide a fast, graphical representation of the decay rate of the fluorescence intensity, which can be further processed to extract the contributions of NADH in bound form (i.e., associated with a long lifetime) relative to the total NADH TPEF signal detected.

Representative images coded by the bound NADH fraction and corresponding mean values from all experimental repeats are shown in FIGS. 4F and 4G (corresponding phasor plots shown in FIGS. 3C-1, 3C-2, and 3C-3). Finally, Fourier-based analysis of the NADH TPEF intensity images, which can be pre-processed to include primarily intracytoplasmic intensity variations and can lack features associated with the nuclei and cell borders (for example, as shown in FIGS. 2F and 2H), indicates that hypoxia can lead to significantly enhanced mitochondrial clustering (as shown in FIGS. 4H, 4I, and FIGS. 3D-1, 3D-b 2, 3D-3). However, unlike the gradual recovery of the redox ratio (shown in FIG. 4A), coinciding with the slow diffusion of atmospheric oxygen back into the media, the elevated mitochondrial clustering can persist for the duration of measurements (shown in FIG. 4C).

This decrease in redox ratio upon the onset of hypoxia can be because the lack of oxygen abolishes the mitochondrial oxidative capacity and shifts the cellular metabolism to an exclusively glycolytic profile (as shown in FIG. 1D). Thus, the cytoplasmic and mitochondrial pools of NADH can increase (as shown in FIG. 1D), leading to the observed decreased redox ratio. A dominant contribution from the cytoplasmic, free, NADH pool can also be consistent with the observed reduction in the NADH bound fraction resulting from the analysis of the lifetime data. The detected increase in mitochondrial clustering can be consistent with mitochondrial fragmentation, resulting from the hypoxia driven disengagement of the electron transport chain and the corresponding decrease in the mitochondrial membrane potential. The persistence of fragmentation while the biochemical equilibrium is under recovery further agrees with the complex bioenergetics of mitochondrial fusion, which necessitate sufficient ATP availability and mitochondrial membrane polarization. This observation is also consistent with studies that examine mitochondrial dynamics under hypoxic conditions using both endogenous TPEF and exogenous fluorescent mitochondrial markers.

Glucose starvation in the HFK cultures can elicit the exact opposite combination of changes in the optical metabolic readouts than those observed during the hypoxic insult. As the glycolytic flux is diminished, mitochondrial bioenergetic adaptation can be required to support cellular homeostasis. To counteract the lack of the glycolytic carbon source, pyruvate, glutamine uptake can be elevated. Glutamine can enter the mitochondria in the form of glutamate, which is converted to α-ketoglutarate and fuels the tricarboxylic acid (TCA) cycle (FIG. 1D). The abrogation of the cytoplasmic, free, NADH pools and the increased mitochondrial oxidative flux yields an increase of the mitochondrial, bound NADH fraction (FIGS. 4B, 4F-1, 4F-2, 4F-3, 4G, 3C-1, 3C-2, 3C-3) and in the overall cellular redox ratio (FIGS. 4A, 4D-1, 4D-2, 4D-3, 4E, 4G, 3A-1, 3A-2, 3A-3). The detected levels of decreased mitochondrial clustering relative to the control population (FIGS. 4C, 4H-1, 4H-2, 4H-3, 4I) can show that nutrient starvation leads to mitochondrial reorganization to a more fused state (FIGS. 3D-1, 3D-2, 3D-3). The latter can be associated with prevention of mitochondrial autophagy and increased oxidative efficiency to maintain ATP levels.

Extrinsic uncoupling by carbonyl cyanide m-chlorophenyl hydrazine (CCCP) can lead to an expected increase in the optical redox and mitochondrial clustering, and a less intuitive increase in the bound NADH fraction. Extrinsic and intrinsic mechanisms of mitochondrial uncoupling can affect the optical readouts. Mitochondrial uncoupling can be an important metabolic perturbation, as it is implicated in lifespan extension, thermogenesis, ischemic preconditioning, and other metabolic processes, through its effects on mitochondrial dynamics, cellular metabolic rate, and reactive oxygen species (ROS) production. Chemical uncoupling induced by carbonyl cyanide m-chlorophenyl hydrazine (CCCP), a proton ionophore that diminishes mitochondrial ATP production by collapsing the proton gradient over the mitochondrial membrane, is expected to augment the rates of glycolysis as well as the TCA (FIG. 1E).

Increased glycolytic flux can be necessary to sustain ATP availability and produce reducing equivalents and carbon substrates that enter the mitochondrial matrix and fuel the TCA cycle, which is accelerated to compensate for the proton leak (FIG. 1E). As the redox state of the cytosolic $NAD^+$ pool is a primary regulator of the glycolytic rate, the cytosolic $NADH/NAD^+$ ratio is maintained at low levels for glycolysis to continue to occur and supply mitochondrial substrates. This can be achieved in a number of ways. For example, lactate dehydrogenase can reduce pyruvate into lactate, using NADH to perform the reduction to restore the $NAD^+$ pool (FIG. 1E). Alternatively, NADH generated during glycolysis can enter the mitochondria by the malate-aspartate shuttle (FIG. 1E), which can function effectively in that direction only when the $NADH/NAD^+$ ratio is higher in the cytosol than in the mitochondrial matrix, otherwise its direction is reversed. Lastly, the glycerol-3-phosphate (G3P) shuttle (FIG. 1E, box 101), alongside the malate-aspartate transporter, can provide a secondary, rapidly operating biochemical pathway that can be utilized for the re-oxidation of glycolytically-formed NADH and entry of its reducing power directly in the electron transport chain through coenzyme Q.

Figure 5A:
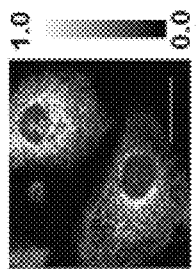
Figure 1:
Figure 2:
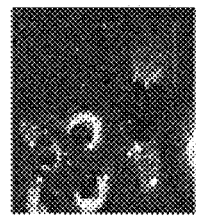
Figure 5B:
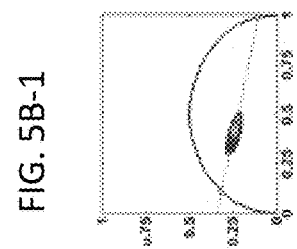
Figure 5C:
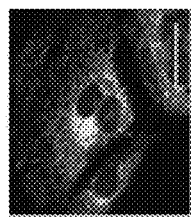
Figure 5D:
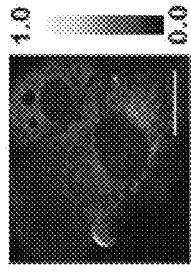
Figure 6F:
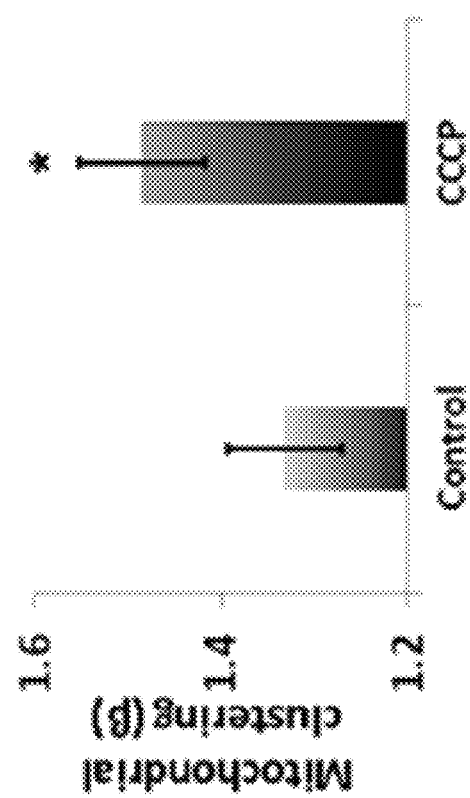

FIGS. 5A-1 through 5D-2 illustrate images of raw dataset for HL-1 cells (e.g., cardiac muscle cell line) under chemical uncoupling, corresponding to representative images shown in FIGS. 6A-1 through 6F. Specifically, FIG. 5A-1 illustrates the control raw NADH data and FIG. 5A-2 illustrates the CCCP raw NADH data. The control raw NADH data can be obtained from illuminating the cellular NADH present in a number of control, i.e., unexposed to treatment, cells with laser having a wavelength of 755 nm. The control raw CCCP data can be obtained from illuminating the cellular NADH present in CCCP treated cells with laser having a wavelength of 755 nm.

FIGS. 5B-1 and 5B-2 illustrate raw FAD images used to generate corresponding redox ratio maps for the control and CCCP data, respectively. FIGS. 5C-1 and 5C-2 illustrate the clustering of pixels in the g-s plane for the control and CCCP data, respectively. FIGS. 5D-1 and 5D-2 illustrate the raw NADH images corresponding to the clone stamped mitochondria images shown later in FIGS. 6E-1 and 6E-2 for the control and CCCP data, respectively.

Figure 6B:
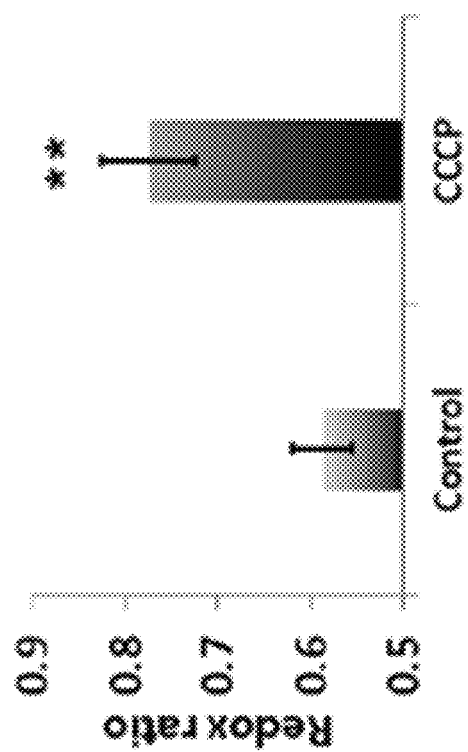
Figure 6D:
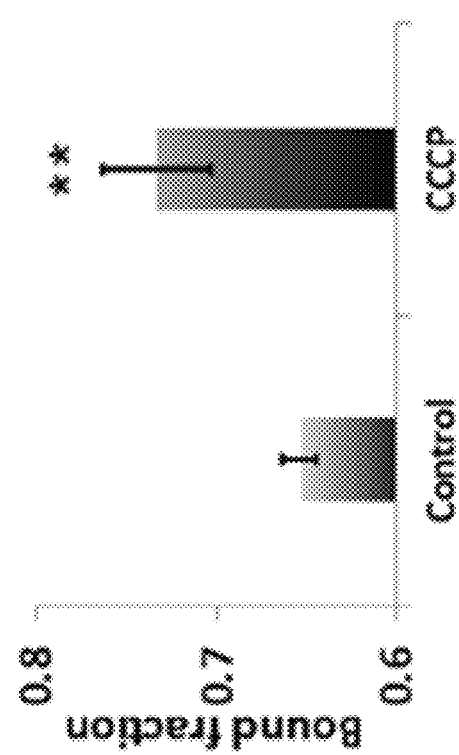

FIGS. 6A-1 through 6F schematically illustrate the optical readouts of HL31 cardiomyocytes in response to chemical uncoupling by CCCP. Specifically, FIGS. 6A-1 and 6A-2 illustrate schematic representative maps of the redox ratio for control and CCCP data, respectively. FIG. 6B illustrates means and standard deviations of the redox ratio for control and CCCP data. FIGS. 6C-1 and 6C-2 illustrate representative maps of bound NADH fraction for control and CCCP data, respectively. FIG. 6D illustrates means and standard deviations of bound NADH fraction for control and CCCP data. FIGS. 6E-1 and 6E-2 illustrate representative images of clone stamped mitochondria for control and CCCP data, respectively. FIG. 6F illustrates the means and standard deviations of mitochondrial clustering for control and CCCP data. The significance symbols, * and **, on top of CCCP bars demonstrate significant differences compared with the control group. The images are obtained by setting n=4 cultures/group and a scale bar: 30 μm, *, p<0.05, **, p<0.01.

The CCCP-induced uncontrolled respiration can lead to a more oxidized cellular state as expressed by the elevated optical redox ratio of HL-1 mouse cardiomyocytes treated with CCCP (FIGS. 6A-1, 6A-2, 6B, 5A-1, 5A-2, 5B-1, and 5B-2) versus their respective control. In this context, based on theoretical expectations, a decrease in bound NADH can be expected as the mitochondrial NADH is consumed, but experimentally longer NADH lifetimes can also be detected (FIGS. 6C-1, 6C-2, 6D, 5C-1, 5C-2).

The dissipation of the pH gradient over the mitochondrial inner membrane can be a factor leading to mitochondrial matrix acidification. This, in turn, can affect the structural dynamics of the electron transport chain proteins that the cellular NADH can interact with in its bound form, while minimally affecting the free NADH lifetime, thus increasing the overall contribution of the bound NADH to the observed lifetime. Other factors can also be involved. For example, changes in the NADH/NAD$^+$ ratio, which can affect the binding dynamics of the NADH related enzymes and thus their lifetime components, along with redistribution of the cellular NADH pools to enhance compensatory pathways, as discussed above, can be in agreement with the detected higher redox ratio, decreased available cellular NADH, increased lactate production, and increased contributions from long (>750 ps) NADH lifetimes. The latter appears to be consistent with lifetimes measured from NADH bound to malate dehydrogenase, G3P dehydrogenase and lactate dehydrogenase. Further, changes in the rotational parameters of the mitochondrial matrix enzymes to which NADH binds can also contribute to the detected increases from the longer lifetime, bound NADH.

Further, CCCP can induce mitochondrial depolarization and subsequent fragmentation, which is consistent with the detected increased mitochondrial clustering levels (FIGS. 6E-1, 6E-2, 6F, 5D-1, and 5D-2). Also, CCCP-induced depolarization can further lead to mitochondrial matrix condensation. A more condensed matrix can yield increased viscosity, which is a micro-environmental parameter known to increase NADH lifetime due to prolonged rotational diffusion time and decreased rotational mobility.

NADH fluorescence lifetime can reveal the involvement of alternative metabolic pathways in response to intrinsic uncoupling in brown adipose tissue vs. CCCP-induced extrinsic uncoupling. Intrinsic mitochondrial uncoupling can be performed by a number of proteins belonging to the mitochondrial anion carrier family, with a subgroup named "uncoupling proteins" (UCP). The first protein identified, UCP1, is the most famous of the four and primarily mediates non-shivering thermogenesis in brown adipose tissue (BAT), acting as a dynamic long-chain fatty acid (LCFA) anion/H$^+$ mitochondrial matrix symporter (as shown in FIG. 1F, Box 103).

Figure 7A:
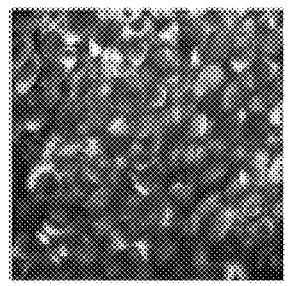
FIGS. 7A-7F schematically illustrate image segmentation of cytoplasm and lipids by taking into account both Flavin Adenine Dinucleotide (FAD) fluorescence intensity and Nicotinamide adenine dinucleotide (NADH) bound fraction.
Figure 7B:
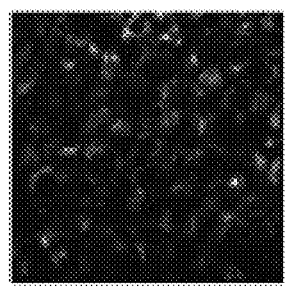
Figure 7C:
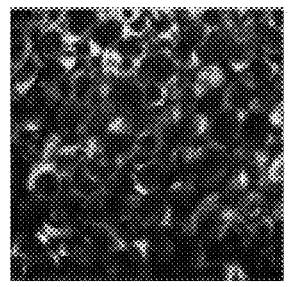
Figure 7D:
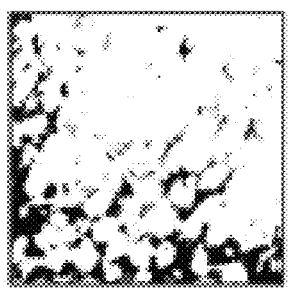
Figure 7E:
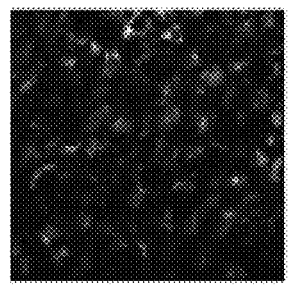
Figure 7F:
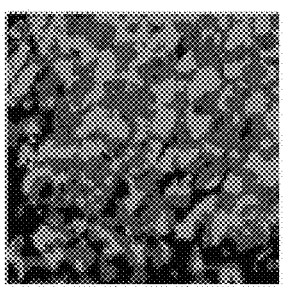
Figures 1, 2, 8A:
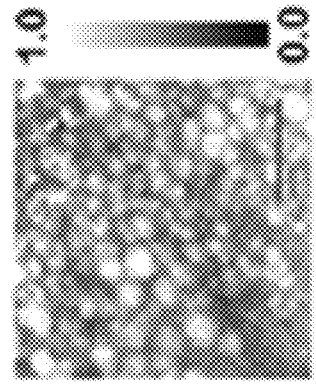
Figures 1, 2, 8B:
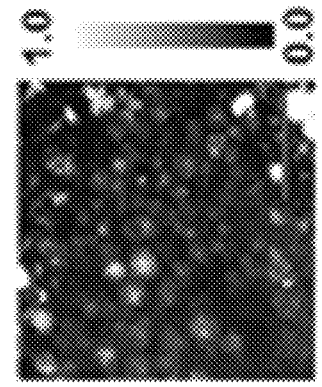
Figures 1, 2, 8E:
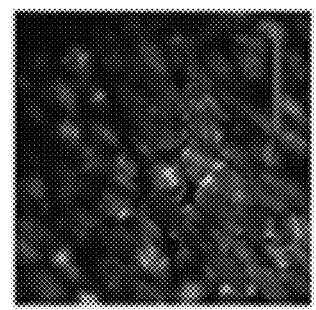
Figures 1, 2, 8F:
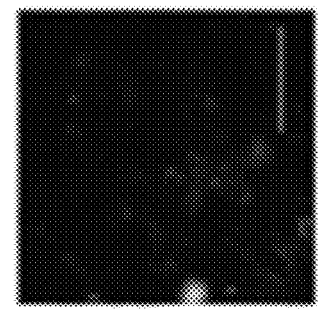
Figures 1, 8C:
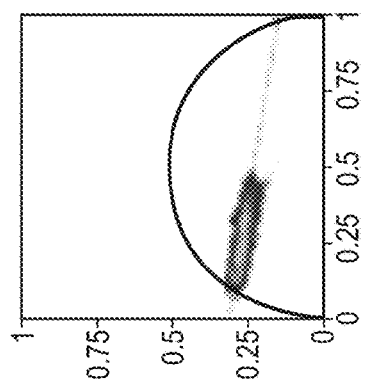
Figures 2, 8C:
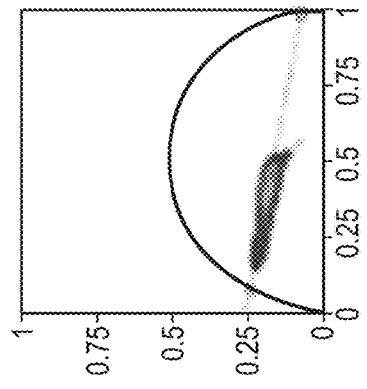
Figures 1, 8G:
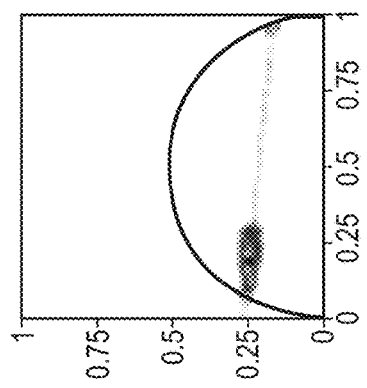
Figures 2, 8G:
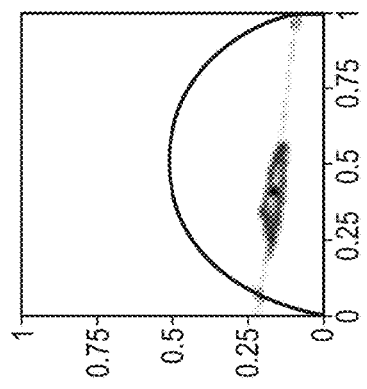
Figures 1, 8D:
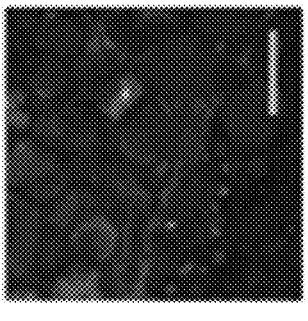
Figures 2, 8D:
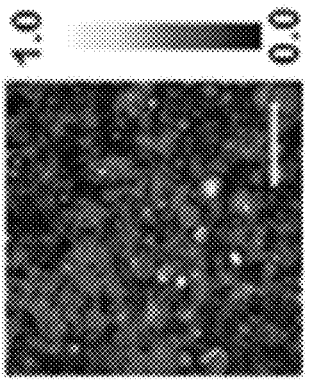
Figures 1, 8H:
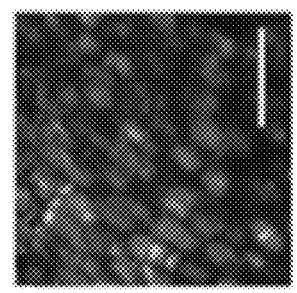
Figures 2, 8H:
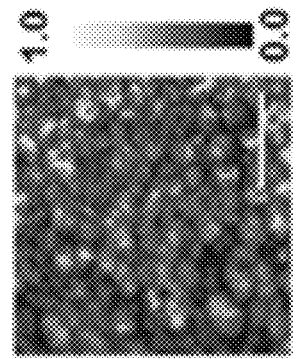

FIGS. 7A-7F schematically illustrate image segmentation of cytoplasm and lipids by taking into account both FAD fluorescence intensity and NADH bound fraction. Specifically, FIG. 7A illustrates the NADH/lipid intensity. FIG. 7B illustrates an image of the FAD intensity. FIG. 7C illustrates an image of an NADH/lipid bound fraction map. FIG. 7D illustrates an image of a binary mask for the tissue area. FIG. 7E illustrates another image of the FAD intensity. FIG. 7F illustrates a plot of the cytoplasm and lipid densities.

FIGS. 8A-1 through 8H-2 illustrate the ex vivo and in vivo raw data set for brown adipose tissue (BAT) under the treatment of cold activation, corresponding to representative images shown in FIGS. 9A-1 through 9O. Specifically, FIGS. 8A-1, 8A-2, 8E-1, 8E-2 schematically illustrate the raw data obtained from illuminating cellular NADH at room temperature (FIGS. 8A-1, 8E-1) and by cold activation (FIGS. 8A-2, 8E-2) under ex vivo (FIGS. 8A-1, 8A-2) and in vivo (FIGS. 8E-1, 8E-2) conditions. FIGS. 8B-1, 8B-2, 8F-1, 8F-2 schematically illustrate raw the FAD data used to generate redox ratio map for room temperature (FIGS. 8B-1, 8F-1) and cold activation (FIGS. 8B-2, 8F-2) under ex vivo (FIGS. 8B-1, 8B-2) and in vivo (FIGS. 8F-1, 8F-2) conditions. FIGS. 8C-1, 8C-2, 8G-1, 8G-2 schematically illustrate Phasor plots of the clustering of pixels in the g-s plane under ex vivo (FIGS. 8C-1, 8C-2) and in vivo (FIGS. 8G-1, 8G-2) conditions. FIGS. 8D-1, 8D-2, 8H-1, 8H-2 schematically illustrate raw NADH images corresponding to the clone stamped mitochondria images shown in FIGS. 9H-1, 9H-2, 9N-1, and 9N-2 under ex vivo (FIGS. 8D-1, 8D-2) and in vivo (FIGS. 8H-1, 8H-2) conditions. The scale bar used for generating FIGS. 8A-1, 8A-2, 8B-1, 8B-2, 8D-1, and 8D-2 is 50 μm. The scale bar used for generating FIGS. 8E-1, 8E-2, 8F-1, 8F-2, 8H-1, and 8H-2 is 100 μm.

FIGS. 9A-9O schematically illustrate the optical readouts of brown adipose tissue (BAT) in response to cold activation (about 4° C.), ex vivo (FIGS. 9D-1 through 9I) or in vivo (FIGS. 9J-1 through FIG. 9O). Specifically, FIG. 9A schematically illustrates the location and composition of BAT. The yellow circle on the mouse indicates the location of BAT that can be used for imaging. FIGS. 9B-1 and 9B-2 schematically illustrate examples of experimental treatments that can be used. FIG. 9B-1 presents an experimental day-night 2-cycle exposure in typical room temperature conditions (e.g −23 degrees C.), whereas FIG. 9B-2 presents an experimental day-night 2-cycle exposure in cold temperature conditions (e.g. −4 degrees C.), although other cooling temperature conditions can be used. FIG. 9C schematically illustrates an example of in vivo imaging of BAT, which is marked by a dashed circle 901. In FIG. 9C, arrow 902 points to the main artery entering and branching into the depots, which is a characteristic anatomical guide used for identifying the BAT tissue. In general, for mice as well as humans, who have similar core temperatures, an ambient temperature below about 17-18° C. would be considered a cooling temperature. Further, the heat transfer can be achieved in a variety of different ways, e.g., air, liquid (e.g., water), a cooling vest, etc.

FIGS. 9D-1 through 9J-2 schematically illustrate representative maps of the redox ratio for room (FIGS. 9D-1, 9F-1, 9H-1, and 9J-1) and cold temperature (FIGS. 9D-2, 9F-2, 9H-2, and 9J-2). FIGS. 9E and 9K schematically illustrate the means and standard deviations of redox ratio at room and cold temperatures. FIGS. 9F-1, 9F-2, 9L-1, and 9L-2 schematically illustrate representative maps of a bound NADH fraction. FIGS. 9G and 9M schematically illustrates the means and standard deviations of a bound NADH fraction at room and cold temperatures. FIGS. 9H-1, 9H-2, 9N-1, and 9N-2 schematically illustrate representative images of an example clone stamped mitochondria. FIGS. 9I and 9O schematically illustrate graphs of means and standard deviations of mitochondrial clustering. The significance symbols "*" on top of cold bars reveal significant differences compared with the control group (room temperature). For both ex vivo and in vivo experiments, n=3 mice/group. The scale bar in FIGS. 9D-1, 9D-2, 9F-1, 9F-2, 9H-1, and 9H-2 is 50 μm. The scale bar in 9J-1, 9J-2, 9L-1, 9L-2, 9N-1, and 9N-2 is 100 μm. The significance symbol * indicates ρ<0.05.

In one experiment, non-shivering thermogenesis is induced by cold exposure and the impact of subsequent norepinephrine-induced activation of brown fat depots of C57BL/6 mice, both ex vivo and in vivo, is observed (FIGS. 7A-7F, 9A, and 9C). In this experiment, consistent changes in the optical metabolic readouts in both ex vivo and in vivo cases are observed. The redox ratio (FIGS. 9D-1, 9D-2, 9E, 9J-1, 9J-2, 9K, 8A-1, 8A-2, 8B-1, 8B-2, 8E-1, 8E-2, 8F-1, and 8F-2) and mitochondrial clustering (FIGS. 9H-1, 9H-2, 9I, 9N-1, 9N-2, 9O, 8D-1, 8D-2, 8H-1, and 8H-2) are significantly increased, consistent with the observations of CCCP-induced uncoupling. This can be a reflection of a more oxidized state of the activated brown fat depots due to higher turnover rates in the electron transport chain. Furthermore, adrenergic stimulation due to cold exposure is known to induce DRP1-dependent mitochondrial fragmentation prior to the depolarization associated with free fatty acid release, UCP1 function and heat production.

Proper mitochondrial fission can be necessary for potentiating mitochondrial depolarization and OPA-1 related cristae restructuring, leading ultimately to matrix swelling. The latter can be an indication that different fissioning responses between the extrinsic and intrinsic mechanisms can exist. As originally expected and contrary to the CCCP outcomes, the NADH bound fraction in the cold-activated BAT is reduced (FIGS. 9F-1, 9F-2, 9G, 9L-1, 9L-2, 9M, 8C-1, 8C-2, 8G-1, 8G-2). The discrepancy between the extrinsic and intrinsic uncoupling lifetime readouts can be attributed to the involvement of alternative metabolic pathways in the BAT tissue function, as well as the differential mitochondrial dynamics responses affecting the matrix density.

Activated BAT tissue can primarily utilize fatty acids (for example, as shown in FIG. 1F) as a direct oxidative substrate to generate acetyl-coA and reducing equivalents (FADH$_2$ and NADH) to maintain the proton gradient. Glycolytic fluxes are mainly driven towards cytosolic ATP production through lactate conversion and can also partially serve an anaplerotic function to replenish citric acid cycle intermediates (i.e., oxaloacetate), which can in turn facilitate the capacity of the TCA to maintain elevated levels of fatty acid oxidation. As such, the cytoplasmic-mitochondrial shuttling mechanisms described earlier (i.e., the malate/aspartate and the G3P shuttle) are often not expected to play significant roles in this case.

Increased levels of free fatty acids can inhibit the mitochondrial flavin moiety of the G3P shuttle, shifting its direction to G3P production, a molecule necessary for free fatty acid incorporation into triacylglycerols (TAGs) and subsequent lipid droplet storage (this process can still be active during brown adipose tissue activation). In addition, UCP1's uncoupling function can be dynamic, based on the availability of free fatty acids released from the induced lipolysis (FIG. 1F). Accordingly, the degrees of uncoupled thermogenesis and respiration can be swiftly and sensibly regulated. Further, under adrenergic stimulation and free fatty acid release, uncoupled thermogenesis and respiration can be upregulated, consuming the mitochondrial NADH and FADH$_2$ and, thereby, increasing the redox ratio and lowering the bound fraction contributions. The decreased matrix condensation (due to the mitochondrial swelling) can also increase the rotational mobility of the enzymatic complexes and, thus, reduce their lifetimes.

Saturated fatty acid overload can induce a significant decrease in the optical redox ratio and bound NADH fraction and an increase in mitochondrial clustering as mitochondria becomes dysfunctional. In some embodiments, fatty acid metabolism is analyzed using fatty acid loading and fatty acid synthesis. Fatty acid metabolism can be highly relevant in increasingly more prevalent metabolic disorders, including obesity, liver dysfunction, cardiomyopathy and diabetes. Using established protocols, C2C12 mouse myoblasts with either oleate, as a representative unsaturated fatty acid, or palmitate, a saturated fatty acid are employed.

Both saturated and unsaturated fatty acids can be chosen since distinct outcomes with regards to cellular parameters, including ROS and ATP production and mitochondrial dynamics can be obtained. During fatty acid catabolism FADH$_2$, NADH and acetyl-CoA are produced sequentially until all of the carbons of the fatty acid chain are utilized (FIG. 1F). Acetyl-CoA can normally enter the TCA cycle to complete its oxidation and production of reducing equivalents, while NADH can enter the electron transport chain through complex I and FADH$_2$ through the electron transfer flavoprotein and Q complex directly, thus bypassing complex I. Increased β-oxidation due to fatty acid overload can introduce primarily an excess of mitochondrial NADH, and, therefore, reduce the optical redox ratio and increase the bound lifetime contributions.

Figures 1, 10A:
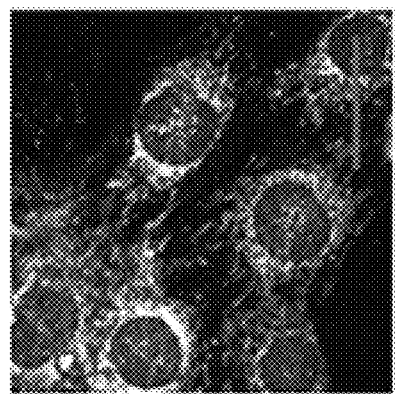
Figures 2, 10A:
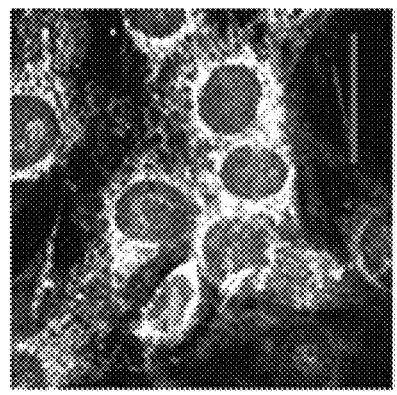
Figures 3, 10A:
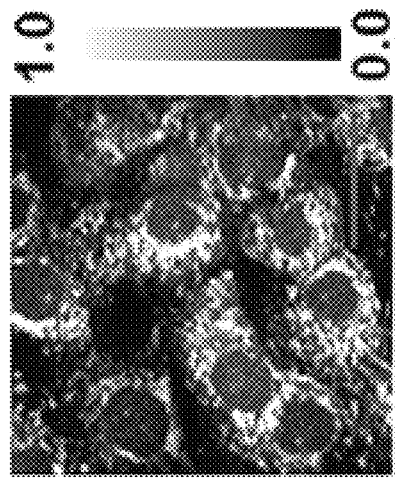

FIGS. 10A-1 through 10D-3 schematically illustrate images of the raw dataset for C2C12 cells (e.g., a mouse myoblast cell line) under metabolic pathway of β oxidation, corresponding to representative images shown later in FIGS. 12A-1 through 12F. Specifically, FIGS. 10A-1 through 10A-3 illustrate images of the raw NADH Vehicle data (FIG. 10A-1, the term "Vehicle" is intended to refer to data having no added fatty acid) and raw Oleate (unsaturated fatty acid, FIG. 10A-2) and Palmitate (saturated fatty acid, FIG. 10A-3) fatty acid data. The term "NADH data" is used herein to refer to generally data in which cellular NADH is illuminated using optical radiation. Similarly, the term "FAD data" is used herein to generally refer to data in which cellular FAD has been illuminated using optical radiation.

Figures 1, 10B:
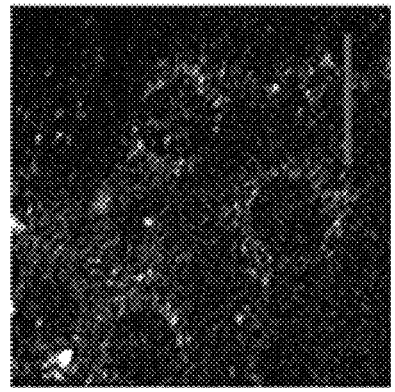
Figures 2, 10B:
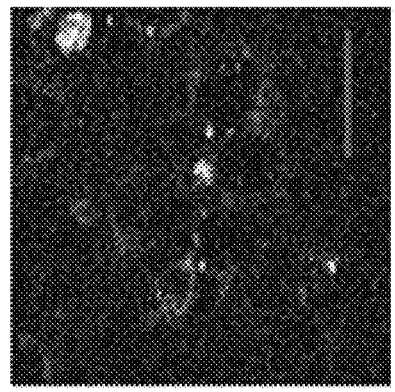
Figures 3, 10B:
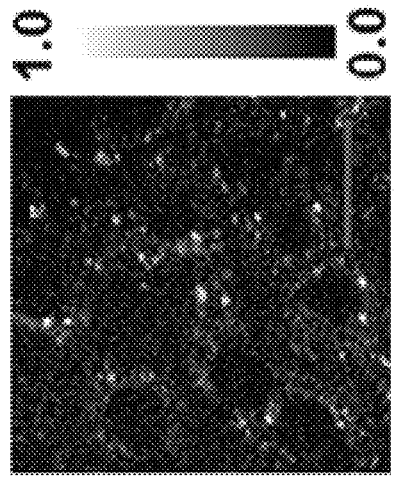
Figures 1, 10C:
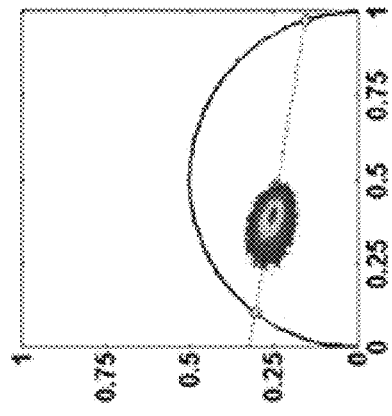
Figures 2, 10C:
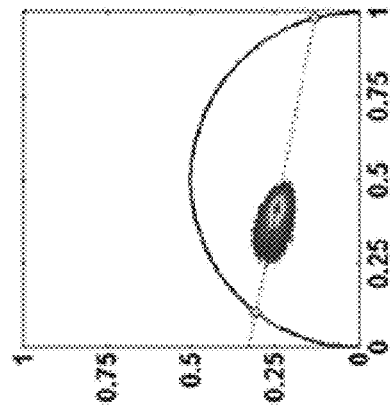
Figures 3, 10C:
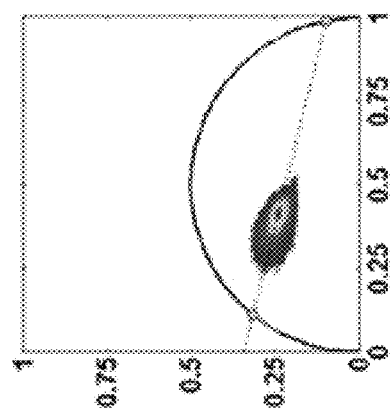
Figures 1, 10D:
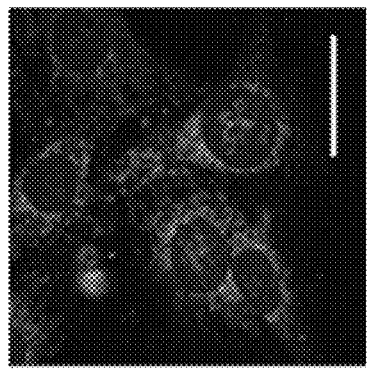
Figures 2, 10D:
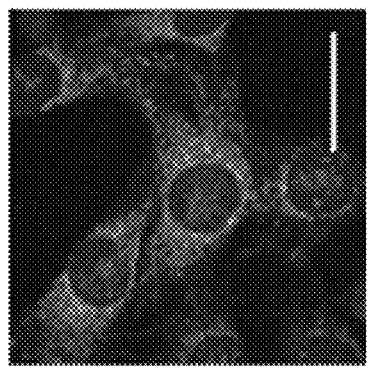
Figures 3, 10D:
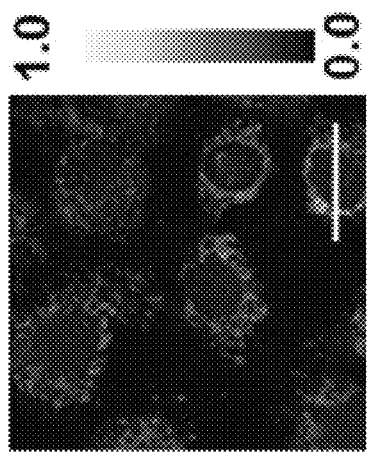

FIGS. 10B-1 through 10B-3 illustrate images of the raw FAD Vehicle data (FIG. 10B-1) and Oleate (FIG. 10B-2) and Palmitate (FIG. 10C-3) fatty acids data, which can be used to generate corresponding redox ratio maps. FIGS. 10C-1 through 10C-3 illustrate images of the phasor plots showing the clustering of pixels in the g-s plane corresponding to Vehicle data (FIG. 10C-1) and Oleate (FIG. 10C-2) and Palmitate (FIG. 10C-3) fatty acid data. FIGS. 10D-1 through 10D-3 illustrate images of the raw NADH Vehicle data (FIG. 10D-1) and Oleate (FIG. 10D-2) and Palmitate (FIG. 10D-3) fatty acid data corresponding to clone stamped mitochondria images shown later in FIGS. 12E-1 through 12E-3.

FIGS. 11-1 through 11-3 illustrate fluorescence images of C2C12 cells (the cells were stained with a fluorescent mitochondrial dye that emanates radiation in the green range of the spectrum). Although shown in black and white, these images are obtained with MitoTracker Green FM staining under different fatty acids supplements. FIGS. 11-1, 11-2, and 11-3 are obtained from Vehicle data and Oleate 200 μM, and Palmitate 200 μM fatty acids, respectively.

Figure 12B:
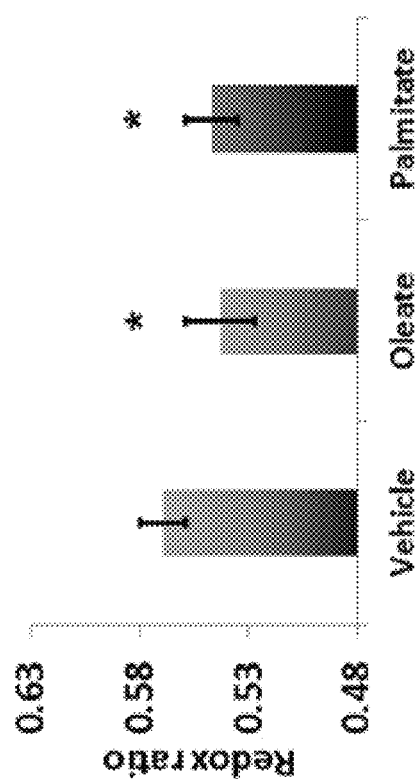
Figure 12D:
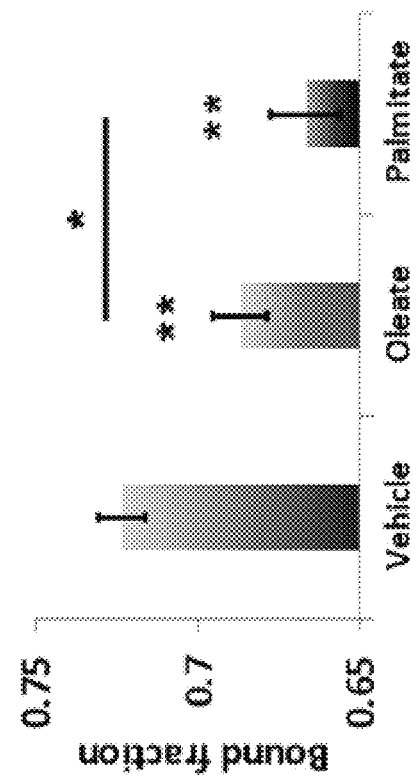
Figure 12F:
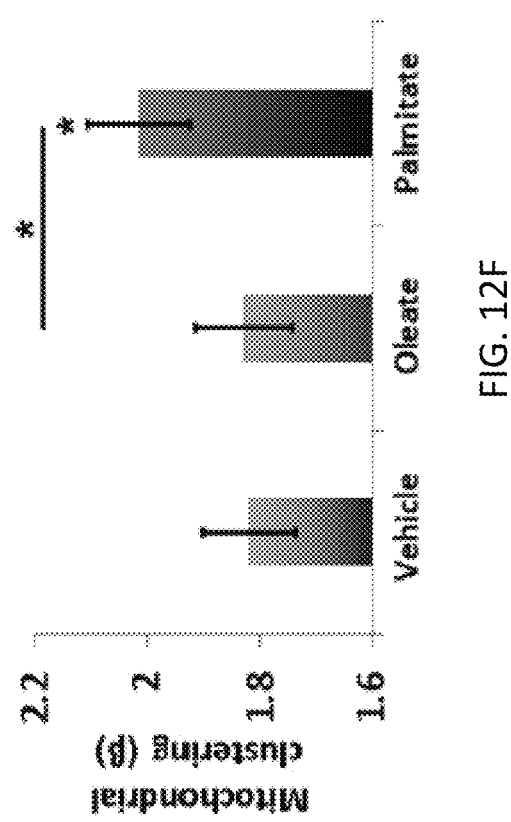

FIGS. 12A-1 through 12F illustrate optical readouts of C2C12 myoblasts under β oxidation induced by supplementing Oleate or Palmitate. Specifically, FIGS. 12A-1 through 12A-3 illustrate representative maps of redox ratio for Vehicle (FIG. 12A-1), Oleate (FIG. 12A-2), and Palmitate (FIG. 12A-3) data. FIG. 12B illustrates the means and standard deviations of the redox ratio. FIGS. 12C-1 through 12C-3 illustrate representative maps of bound NADH fraction for Vehicle (FIG. 12C-1), Oleate (FIG. 12C-2), and Palmitate (FIG. 12C-3) data. FIG. 12D illustrates the means and standard deviations of the bound NADH fraction. FIGS. 12E-1 through 12E-3 illustrate representative maps of clone stamped mitochondria for Vehicle (FIG. 12E-1), Oleate (FIG. 12E-2), and Palmitate (FIG. 12E-3) data. FIG. 12F illustrates the means and standard deviations of mitochondrial clustering. The significance symbols "*" on top of adipogenic bars reveal significant differences compared with the MSC propagation group. In this example, n=4 cultures/group and scale bar is 50 μm. Significance symbol * indicates p<0.05 and ** indicates p<0.01.

Both fatty acids (Oleate and Palmitate) can lead to a decrease in the redox ratio (FIGS. 12A-1, 12A-2, 12A-3, 12B-1, 12B-2, 12B-3, 10A-1, 10A-2, 10A-3, 10B-1, 10B-2, 10B-3). However, these fatty acids can have significantly decreased levels of NADH bound fraction upon treatment with Oleate and even lower levels upon exposure to Palmitate (FIGS. 12C-1, 12C-2, 12C-3, 12D, 10C-1, 10C-2, 10C-3). However, no changes in the mitochondrial clustering of Oleate treated cells are observed, whereas Palmitate treatment could induce increased mitochondrial clustering (FIGS. 12E-1, 12E-2, 12E-3, 12F, 10D-1, 10D-2, 10D-3).

As shown in FIG. 11-3, Palmitate can induce mitochondrial dysfunction and fragmentation, due to increased ROS production. However, as shown in FIG. 11-2, Oleate can preserve mitochondrial function and architecture. These distinct mitochondrial dynamics outcomes can be attributed to the diverse chemical characteristics of the fatty acids. Although both fatty acids can be expected to create an energetic burst, since Oleate has double bonds, it can require an NADPH-mediated oxidation step. This oxidation step can slow the catabolic rate and steadily consume NADPH, which can be recreated by consuming the proton gradient. Moreover, unsaturated fatty acids can be more easily incorporated into TAGs and can be chemically better mitochondrial uncouplers than their saturated counterparts. Therefore, Oleate can be more easily stored intracellularly and, while it can create an energetic surplus, it can also steadily and mildly consume the proton gradient and can uncouple the proton motive force from ATP production. This, in turn, can promote the forward flow of electrons through the respiratory chain and decrease the chances of Q complex competition overload by the $FADH_2$ and the NADH that compete to oxidize complex Q (FIG. 1F). Therefore, the cell can evade the formation of ROS by complex I induced by reversed electron transport function, and can preserve mitochondrial function and architecture.

In contrast, Palmitate can lack the beneficial characteristics described for Oleate and can induce rapid ROS formation, mitochondrial fragmentation, mitochondrial dysfunction, and ultimately decreased ATP production. This unexpected NADH lifetime reduction can be due to cytoplasmic NADH contributions from peroxisomal β-oxidation and reversed malate-aspartate shuttle function. Peroxisomal β-oxidation can produce NADH in a similar manner, as the mitochondrial one. Re-oxidation of the intraperoxisomal NADH is necessary for the β-oxidation to continue and that can happen in the cytosol and the mitochondria. Therefore, a shuttling mechanism can be necessary to regulate intraperoxisomal $NAD^+$/NADH, transferring NADH to the cytosol. Although a peroxisomal to cytosolic shuttling mechanism has not been precisely identified yet in eukaryotes, evidence exists for a lactate/pyruvate-based redox shuttle (FIG. 1F). The cytosolic NADH can be recycled through one of the two cytosolic to mitochondria NAD(H)-redox shuttles described previously. As noted, the malate-aspartate shuttle can be bidirectional and can depend highly on the cytosolic and mitochondrial $NADH/NAD^+$ ratios. Mitochondrial NADH can be accumulated when mitochondrial β-oxidation levels are high. As high mitochondrial $NADH/NAD^+$ ratio can inhibit β-oxidation, the shuttle can act in reverse, shuttling NADH to the cytoplasm.

The G3P shuttle can include a reversible NADH to G3P oxidation step and an irreversible G3P to $FADH_2$ reduction. During high levels of free fatty acids, the $FADH_2$ reduction can be attenuated, promoting the cytosolic NADH oxidation to G3P production and TAG biosynthesis. Through this mechanism, Palmitate, due to its decreased TAG incorporation, is anticipated to have an even lower bound NADH fraction than Oleate. In the case of Palmitate, a continuously increasing cytosolic $NADH/NAD^+$ due to palmitate's energetic burst and decreased TAG incorporation can ultimately inhibit both peroxisomal and mitochondrial metabolism. This continuous and uncontrolled cellular redox decrease can be a major participant in the lipotoxicity, accumulation of metabolic intermediates, and cell death observed after prolonged incubation times with palmitate alone.

Figures 2, 13A:
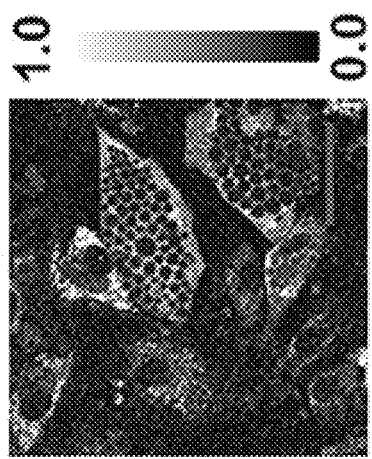
Figures 2, 13B:
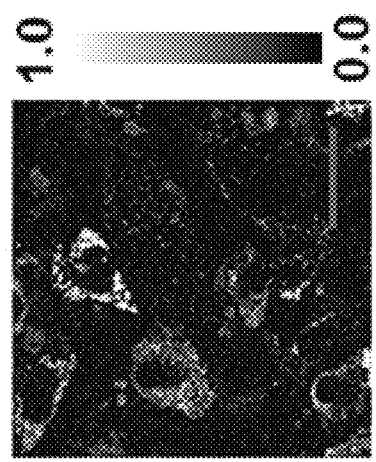
Figures 1, 13A:
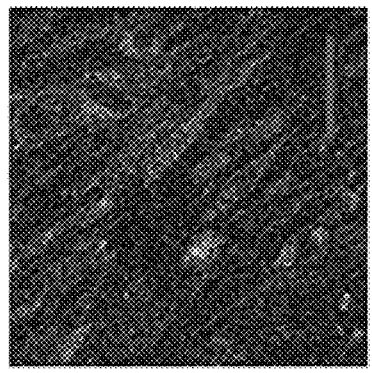
Figures 1, 13B:
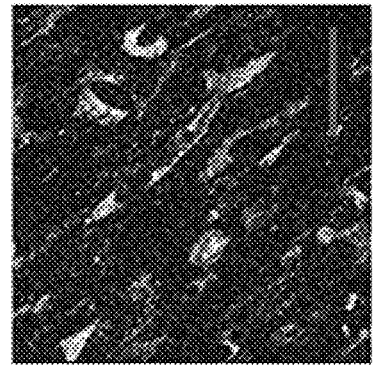
Figures 1, 13C:
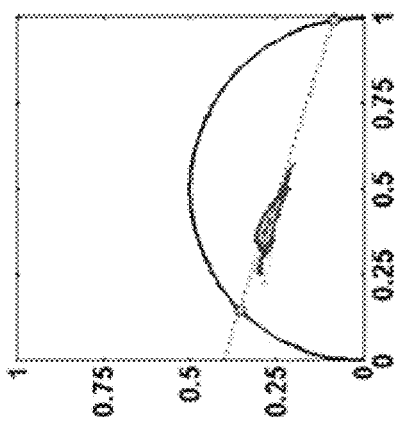
Figures 2, 13C:
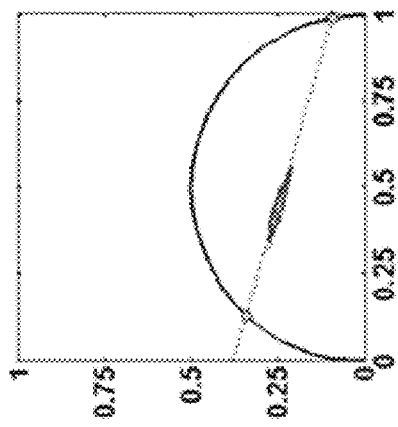
Figures 1, 13D:
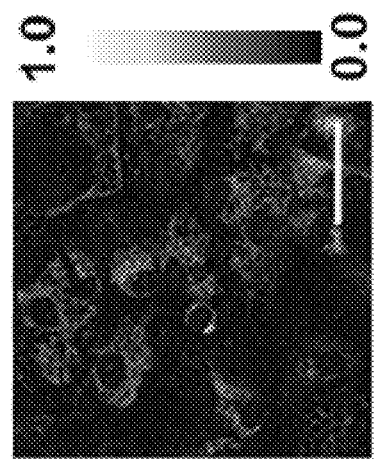
Figures 2, 13D:
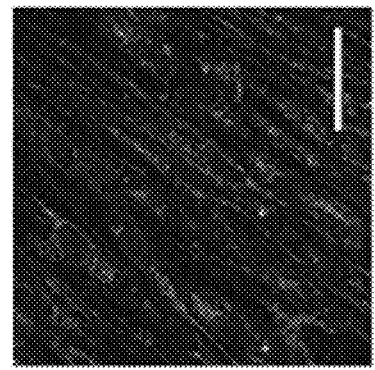

FIGS. 13A-1 through 13D-2 schematically illustrate images of raw datasets for mesenchymal stem cells (MSCs) during lipogenesis. The raw data shown in FIGS. 13A-1 through 13D-2 are used to produce the representative images shown in FIGS. 14A-1 through 14F. Specifically, FIG. 13A-1 illustrates the raw NADH data obtained from propagation of MSCs. FIG. 13A-2 illustrates the raw data obtained from adipogenic cell differentiation. FIGS. 13B-1 and 13B-2 illustrate the raw FAD images used to generate redox ratio map for MSC propagation and adipogenic data, respectively. FIGS. 13C-1 and 13C-2 include phasor plots illustrating the clustering of pixels in the g-s plane. FIGS.

13D-1 and 13D-2 illustrate the raw NADH images corresponding to the clone stamped mitochondria images shown later in FIGS. 14E-1 and 14E-2 for MSC propagation and adipogenic data, respectively. The scale bar used for generating these images is 50 µm.

Figures 2, 14A:
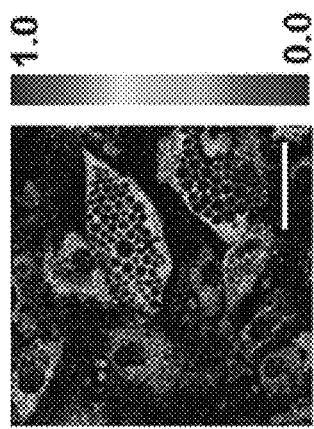
Figures 2, 14C:
Figures 2, 14E:
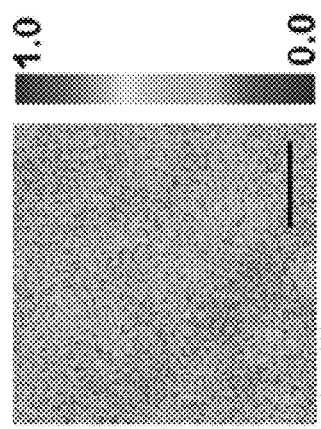
Figures 1, 14A:
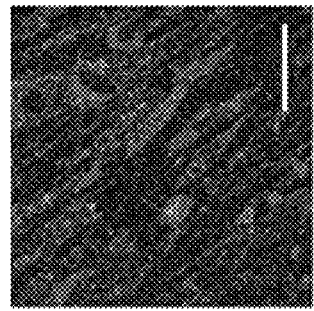
Figures 1, 14C:
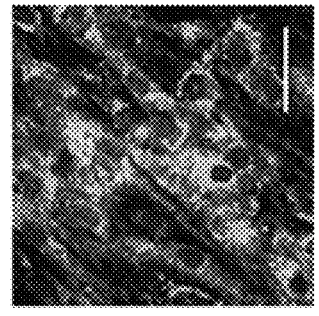
Figures 1, 14E:
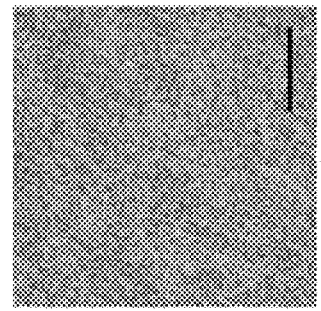

FIGS. 14A-1 through 14F schematically illustrate images of optical readouts of mesenchymal stem cells (MSCs) during metabolic pathway of lipogenesis. Specifically, FIGS. 14A-1 and 14A-2 include representative maps of redox ratio for MSC propagation and adipogenic data, respectively. FIG. 14B illustrates a plot of the means and standard deviations of redox ratio. FIGS. 14C-1 and 14C-2 include representative maps of the bound NADH fraction for MSC propagation and adipogenic data, respectively. FIG. 14D illustrates a plot of the means and standard deviation of bound NADH fraction. FIGS. 14E-1 and 14E-2 illustrate the representative images of clone stamped mitochondria for MSC propagation and adipogenic data respectively. FIG. 14F illustrates plots of the means and standard deviations of mitochondrial clustering. The significance symbols on top of adipogenic bars reveal significant differences compared with the MSC propagation group. In these images, n=4 cultures/group, scale bar is 50 µm, *, p<0.05; **, p<0.01.

Fatty acid synthesis can lead to the accumulation of bound NADH in mitochondria and an increase in mitochondrial clustering to facilitate biosynthesis. The differentiation of mesenchymal stem cells into adipocytes can be employed to determine the impact of fatty acid synthesis. Specifically, as shown in FIGS. 14A-1, 14A-2, fatty acid synthesis can be accompanied by a decrease in the redox ratio (also as shown in FIGS. 14B, 13A-1, 13A-2, 13B-1, 13B-2). This change can be attributed to mitochondrial biogenesis and the accumulation of mitochondrial NADH as glucose catabolism outpaces ATP production to support the biosynthetic drive that consumes TCA intermediates (i.e., citrate) (FIG. 1F). These processes can also lead to a corresponding increase in the bound NADH fraction (FIGS. 14C-1, 14C-2, 14D, 13C-1, 13C-2). The associated increase in mitochondrial clustering (FIGS. 14E-1, 14E-2, 14F, 13D-1, 13D-2) is consistent with mitochondrial truncation and branching to efficiently surround the lipid droplets and facilitate lipid biosynthesis compared to the more extended mitochondrial networks of the undifferentiated human mesenchymal stem cells.

Figure 15D:
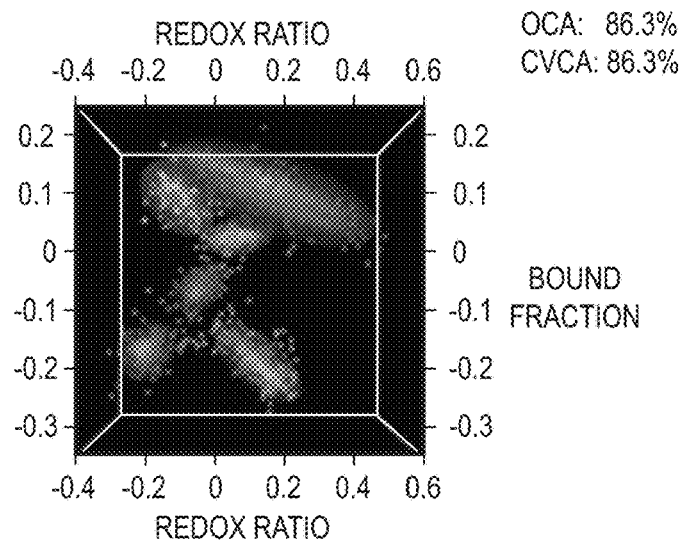
Figure 15E:
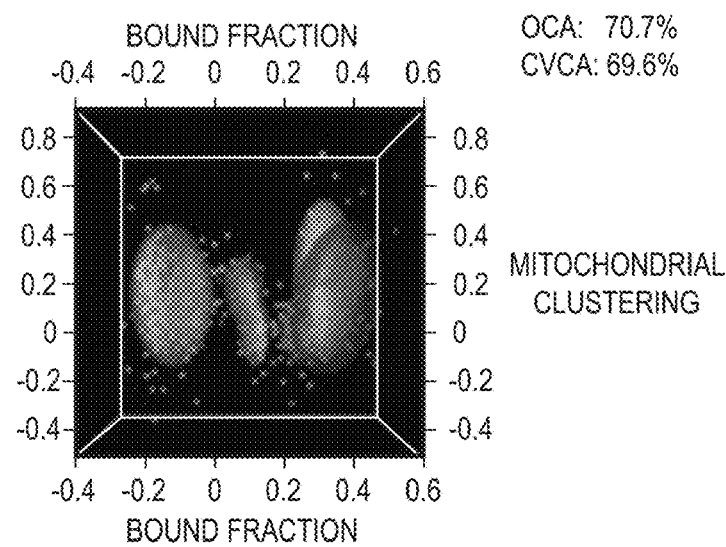
Figure 15F:
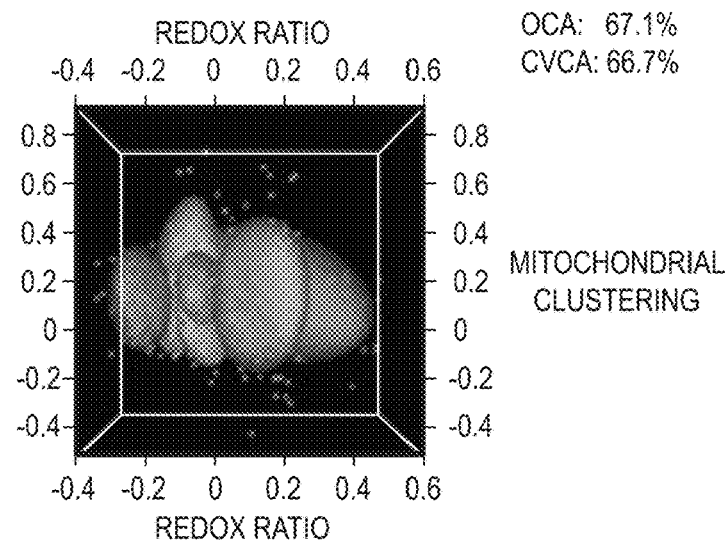

Multi-parametric functional assessment can enable identification of the nature of metabolic perturbation and quantitative characterization of the heterogeneity in cellular responses. FIGS. 15A-15F schematically illustrate examples of classifications of metabolic pathways obtained using one or two optical metrics. Specifically, FIG. 15A illustrates an example in which the redox ratio is utilized to classify metabolic pathways. FIG. 15B illustrates an example in which NADH bound fraction is utilized to classify metabolic pathways. FIG. 15C illustrates an example in which mitochondrial clustering is used to classify metabolic pathways. In FIG. 15D both redox ratio and NADH bound fraction are used to classify metabolic pathways. In FIG. 15E both NADH bound fraction and mitochondrial clustering are used to classify metabolic pathways. In FIG. 15F both redox ratio and mitochondrial clustering are used to distinguish different metabolic pathways. The classification accuracy values are labeled along with each approach. The term "OCA" on FIGS. 15A-15F denotes original classification accuracy and the term "CVCA" denotes cross-validated classification accuracy.

FIG. 16 illustrates a table that includes the individual heterogeneity index for each optical metric (i.e., redox ratio, bound fraction, and mitochondrial clustering) under various perturbation values. The significance symbol "*" indicates significant difference compared with corresponding control in each experiment. Differences can be evaluated, for example, using an analysis of variance (ANOVA) technique with a post-hoc Tukey HSD test to determine if there are multiple groups (e.g., glycolysis and glutaminolysis, and β-oxidation). In certain embodiments, a two-tailed t-test can be used. In this example * represents ρ<0.05.

Figures 3, 17D:
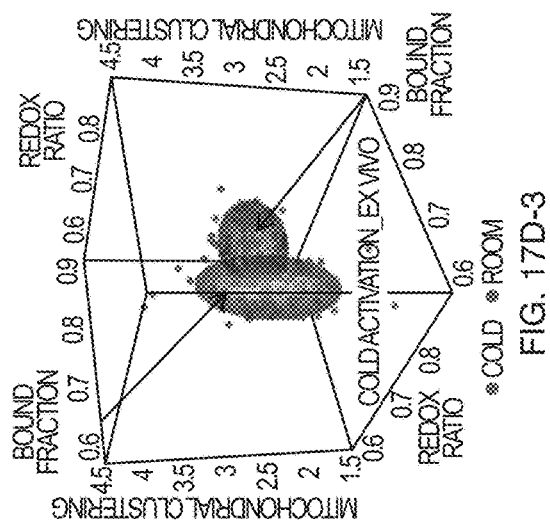
Figures 6, 17D:
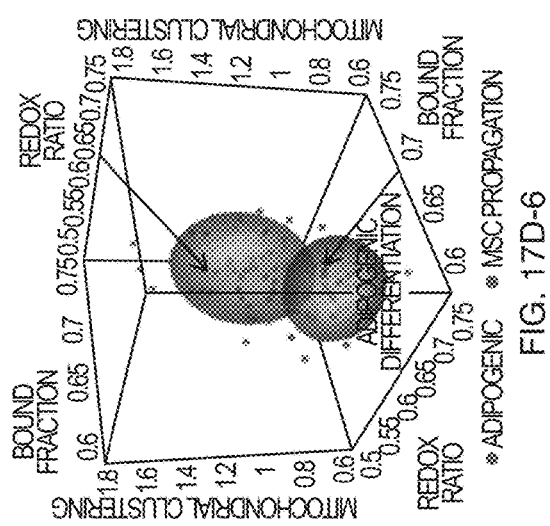
Figures 2, 17D:
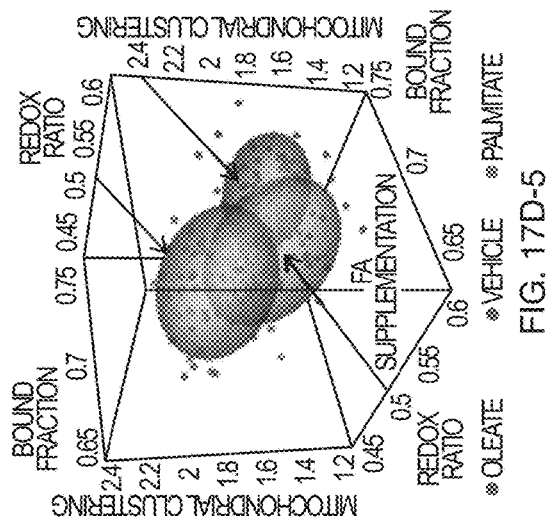
Figures 5, 17D:
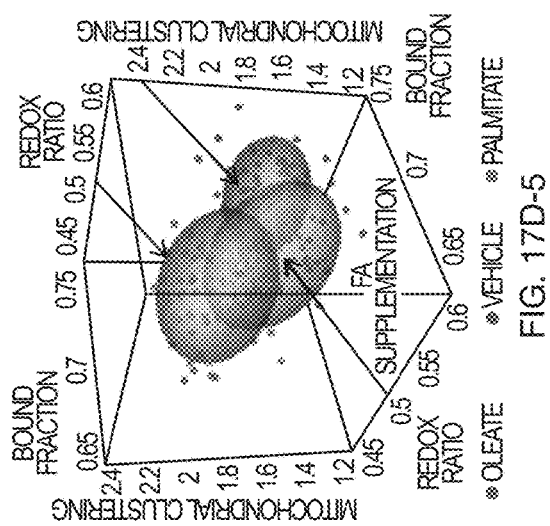
Figures 1, 17D:
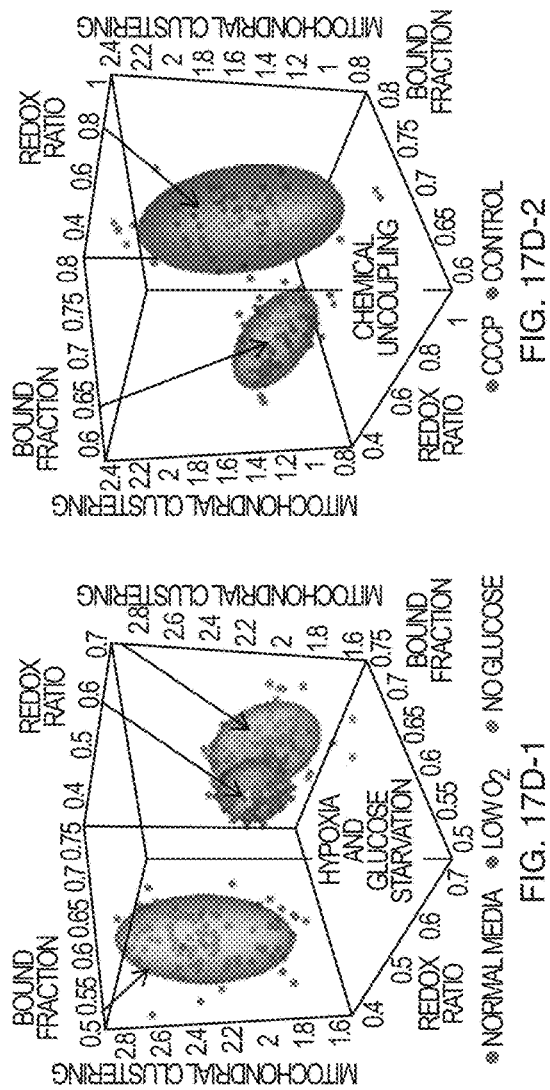
Figures 4, 17D:
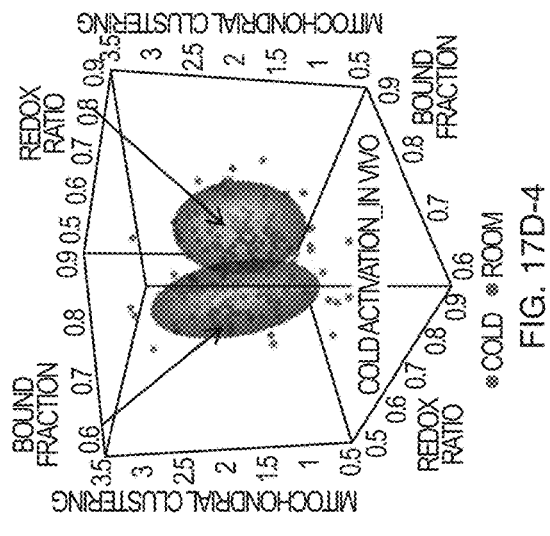

FIGS. 17A-17D-6 schematically illustrate examples of holistic visualization of dataset using the three optical metrics described herein. Specifically, FIG. 17A illustrates a table that includes a summary that combines changes of optical readouts under different metabolic perturbations. FIG. 17B includes a plot that schematically illustrates that a combination of these three optical metrics at the biological replicate level can distinguish all of the metabolic pathways. FIG. 17C includes a plot that schematically illustrates that a combination of relative changes in these three optical metrics at the cell level can yield an original classification accuracy of 90.9% and a cross-validated classification accuracy of 90.6% in classifying metabolic pathways. FIGS. 17D-1 through 17D-6 include 3D scatter plots that have been obtained based on single cell analysis for visualization of heterogeneity across individual cells under various metabolic perturbations. Specifically, FIGS. 17D-1 through 17D-6 include 3D scatter plots obtained under hypoxia and glucose starvation (FIG. 17D-1), chemical uncoupling (FIG. 17D-2), ex vivo cold activation (FIG. 17D-3), in vivo cold activation (FIG. 17D-4), FA supplementation (FIG. 17D-5, and adipogenic differentiation (FIG. 17D-6).

As shown in FIG. 17A, a combination of endogenous optical metabolic readouts can be used to determine the presence of a metabolic change and/or the underlying metabolic processes that produce such change. For example, while both enhanced glycolysis and fatty acid synthesis lead to a decrease in the optical redox ratio and an increase in mitochondrial clustering, the NADH bound fraction can decrease in the former and can increase in the latter case. Thus, characterization of all three optical metabolic readouts can lead to identifying the underlying mechanisms that drive detected metabolic changes (FIG. 17B). Further, since cellular diversity can be one of the greatest challenges in deciphering biological function and response to treatment, the extents to which these optical biomarkers can provide complementarity information can be determined based on the quantification of their classification potential at the cellular level.

Single cell functional analysis can be an important factor in understanding the complex behavior and heterogeneity of biological systems. FIG. 17C includes a graph that illustrates the results obtained from analysis of metabolic readouts of 1133 randomly selected cells. Among these 1133 cells, 651 cells belong to the groups of cells exposed to perturbations that can lead to changes in glycolysis, glutaminolysis, uncoupling, and fatty acid oxidation or synthesis, and 482 belong to control groups. The relative differences of each cell belonging to the perturbation groups (48-108 cells per perturbation) with respect to the mean cell behavior of the control group are shown in FIG. 17C. The three-metric combination produces the highest separation and quantitatively yields to the highest original (90.9%) and cross-validated accuracy (90.6%) in classifying the 651 cells into the seven experimental alterations examined.

In contrast, the utilization of one or two metrics at a time can yield varying accuracies ranging from 33.3-66.5% (using only one metric, as shown in FIGS. 15A-15C) or 66.7-86.3% (using two metrics, as shown in FIGS. 15D-15F). FIGS. 17D-1 through 17D-6 illustrate the distributions of these 1133 cells for each experimental perturbation, enabling a holistic visualization of multivariate optical measures of cellular functional heterogeneity. In the majority cases, as evident by the enlarged ellipsoids, there can be an increase in overall heterogeneity in treated groups, which can reveal cellular diversity in response to perturbations. The heterogeneity in response, as visualized by distinct changes in the overall three dimensional orientation of the ellipsoids and quantified by the heterogeneity index, is not always driven by the same optical biomarker, further signifying the functional complementarity of the markers. The ability to perform single cell analysis to probe functional heterogeneity while relying on entirely endogenous sources of contrast, within intact, live cells and tissues, dynamically over time, can offer significant advantages over traditional, metabolic assays which are generally performed on cell extracts. Accordingly, multi-parametric two-photon imaging of endogenous molecules and subcellular structures can enable non-invasive and quantitative assessments of metabolic alterations at the single-cell or tissue level.

Figure 18:
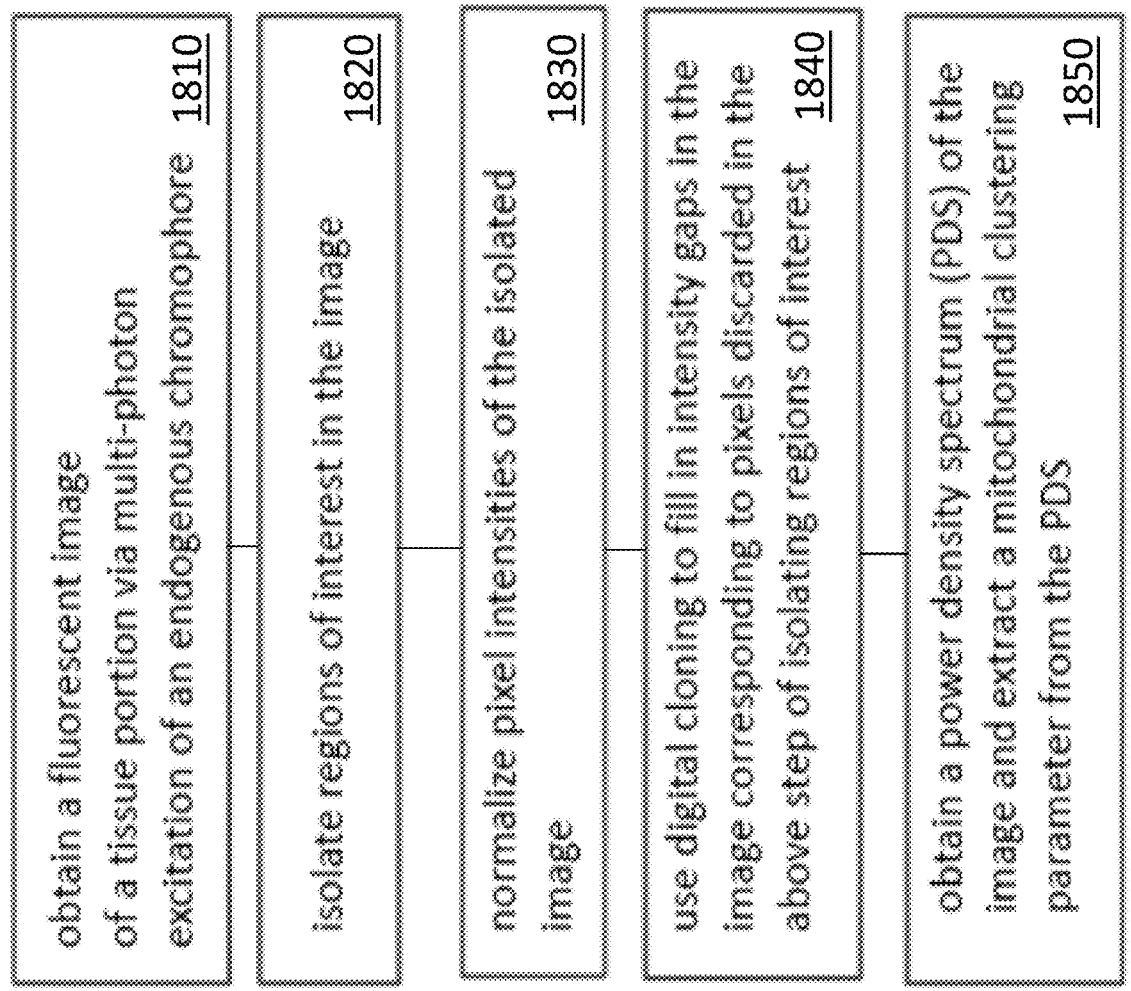
FIG. 18 is a flow diagram of procedures that can be used for focusing radiation into one or more tissue segments in accordance with some embodiments disclosed herein.
Figure 19:
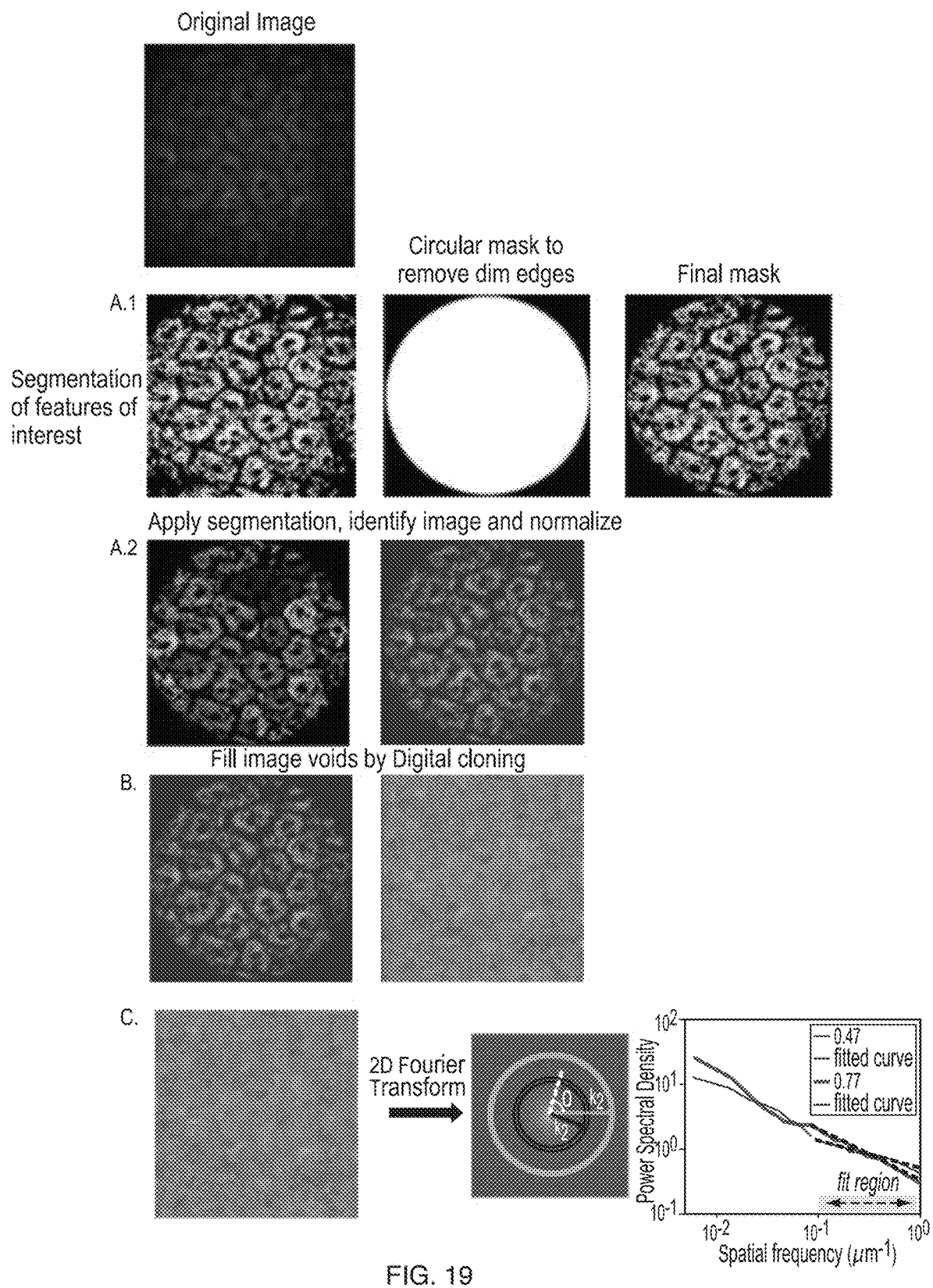
FIG. 19 is another flow diagram of procedures that can be used for focusing radiation into one or more tissue segments in accordance with some embodiments disclosed herein.

FIG. 18 is a flow diagram of procedures that can be used for focusing radiation into one or more tissue segments in accordance with some embodiments disclosed herein. FIG. 19 is another flow diagram of procedures that can be used for focusing radiation into one or more tissue segments in accordance with some embodiments disclosed herein.

With reference to the flow diagrams of FIGS. 18 and 19, a method of imaging tissue according to an embodiment of the present teachings can include focusing optical radiation (typically laser radiation) into one or more tissue segments so as to cause a multi-photon excitation of nicotinamide adenine dinucleotide (NADH) in the tissue and detecting fluorescence radiation emitted by excited NADH to form a raw (original) image of the tissue segment(s) 1810. NADH is intrinsically fluorescent and plays a key role in cellular energy metabolism. Moreover, NADH fluorescence intensity images are sensitive predominantly to the bound NADH form residing within mitochondria, owing to its increased fluorescent yield in that state. Thus, NADH imaging is employed in many embodiments of the present teachings to monitor the state of mitochondria and their organization in-vivo.

The wavelength of illuminating radiation can be selected to excite a chosen chromophore, e.g., to excite NADH. In some embodiments, the wavelength of the excitation radiation can be in a range of about 600 nm to about 1400 nm, e.g., between 700 and 800 nm.

The NADH fluorescence image can be processed to obtain a mitochondrial clustering parameter, as discussed above. With continued reference to FIGS. 18 and 19, the original image can be segmented so as to isolate intracellular regions of interest (mitochondria in this embodiment) and remove the other regions, e.g., via masking. By way of example, for removal of nuclear and interstitial regions in the original image, a bandpass filter can be applied to the image. In some embodiments, such a bandpass filter can be created by combining three separate bandpass filters. The first bandpass filter can be formed by multiplying a Gaussian high pass filter (e.g., $\sigma=0.01$ μm−1) and a Gaussian low pass filter (e.g., $\sigma=0.1$ μm−1). The second filter can also be formed by combining a high-pass Gaussian filter (e.g., $\sigma=0.021$ μm−1) with a low-pass Gaussian filter ($\sigma=0.143$ μm−1). The third filter can be created by combining 3rd order Butterworth low-pass and high-pass filters. By way of example, the frequency cut-off of the Butterworth high-pass filter can be set to 0.021 $\mu m^{-1}$ and the frequency cut-off of the Butterworth low-pass filter can be set to 0.2 $\mu m^{-1}$, though other cut-off frequencies and filter designs can also be employed. In some embodiments, the combination of Gaussian and Butterworth filters can minimize ringing artifacts in the image while providing enough selectivity to isolate the size range of cytoplasmic image features of interest.

Following the application of the filter, the filtered image can be transformed into a binary mask, for example, via application of Otsu's auto-thresholding function, composed of "bright" pixels corresponding to the regions of interest in the image and "dark" pixels corresponding to the discarded regions (e.g., nuclei and interstitial regions between boundaries of the cells). In some embodiments, additional masks may be employed to eliminate certain unwanted regions/features of the filtered image, such as dim image corner artifacts.

Subsequently, in this embodiment, the pixel intensities can be normalized. Such normalization can be achieved in a variety of different ways. For example, the total NADH intensity can be calculated by summing the pixel fluorescence intensity values and the total intensity can be used to scale the pixel intensities. In some cases, the following intensity normalization approach can be employed to minimize large scale intensity artifacts, for example due to optical aberrations during image acquisition. Specifically, for each identified connected component within the image, which can typically include one or a few cells, the sum of the pixel intensities can be calculated. The intensity of each participating pixel in each connected component can be normalized by the corresponding intensity sum, yielding substantially uniform average intensities for the participating components.

Subsequently, the intensity gaps (voids) in the normalized image (i.e., the masked dark pixels) can be filled in using an automated digital cloning (DOC) technique. For example, such a cloning technique can be employed to fill the intensity gaps within the image produced by the nuclear and interstitial feature removal, without overwriting any bright foreground pixels, to generate a resultant image (herein also referred to as a processed image). In some embodiments, the digital cloning technique can be applied multiple times and the results can be averaged to obtain a resultant average image. An example of a suitable digital cloning technique is described in an article entitled "Improved Fourier-based characterization of intracellular fractal features," authored by Xylas et al. in Opt. Express 20, 23442-23455 (2012), which is herein incorporated by reference in its entirety.

A power spectral density (PSD) of the processed image can then be computed, e.g., via obtaining Fourier transform of the image. The power spectral density can be employed to extract a mitochondrial clustering parameter. For example, in some embodiments, a region of the PSD corresponding to spatial frequencies less than a selected threshold, e.g., 0.1 μm−1, can be fitted to the above Equation (1) to extract the mitochondrial clustering parameter, $\beta$, where increased values of $\beta$ indicates more clustered (fragmented) mitochondrial formations.

In some embodiments, the excitation radiation can excite not only a chromophore of interest, e.g., NADH, but also other chromophores that may be potentially present, e.g., collagen, elastin, keratin and melanin. In some such embodiments, one or more filters, e.g., Shanbhag's entropy filter, can be applied to the original image to minimize, and preferably eliminate, the contributions of these other chromophores to the image signal.

In some embodiments, the above imaging method can be used to obtain the mitochondrial clustering parameters at a plurality of depths of a tissue portion, e.g., the epithelium, e.g., the epidermis. In some embodiments, the depth dependence of the mitochondrial clustering parameter can then be employed as a predictive tool to differentiate pre-cancerous or cancerous tissue from healthy tissue. For example, it has been discovered that in healthy epidermal epithelia the basal and parabasal layers can display high and stable values of the clustering parameter. In particular, it has been discovered that as the epithelial cell differentiation progresses from the basal to the higher epidermal layers, the clustering parameter shows declining values, reaching its minimum within the spinous layer (tubular mitochondria). Further, towards the most terminal differentiation state as the granular keratinocytes enter an apoptotic state to create the stratum corneum, the mitochondrial clustering parameter values start to recover, signifying a return to a more fissioned phenotype. In contrast, it has been discovered that in diseased epithelium, e.g., epidermis, the mitochondrial organization can lack depth-dependence.

FIG. 20 schematically depicts a system according to some embodiments disclosed herein, which includes a multi-photon microscope 10, such as those commercially available (e.g., a multi-photon microscope marketed by JenLab Gmb under trade designation MPTflex), which can be used to obtain fluorescent images of tissue, e.g., via multiphoton excitation of endogenous chromophores, such as NADH. An analyzer 12 can receive the images and process those images in a manner discussed herein to obtain information about organization and biochemical states of one or more selected cellular structures, e.g., the mitochondria. The analyzer can be implemented in hardware, software, firmware or a combination thereof using methods known in the art and supplemented in accordance with the present teachings.

The data used to generate the results presented in FIGS. 1D-19 were obtained using the experimental procedures discussed below.

Cell Culture and Treatment: Primary human foreskin keratinocytes (HFKs) are cultured and exposed to either control, hypoxia or glucose starvation conditions using protocols described in detail previously. HFKs are cultured on 50 mm glass bottom dishes (MatTek) until reaching confluence. Two types of media are prepared for different treatments: (i) media prepared in-house with the same glucose and glutamine concentrations as KSFM (Low Glu), or (ii) media prepared in-house with the same glutamine concentration as KSFM, but with no glucose (No Glu). Low Glu media are prepared by adding 1 g/L of glucose (Sigma-Alrich), and 584 mg/L of L-glutamine (Sigma-Alrich) in no glucose, no glutamine, and no phenol red DMEM. No Glu media are prepared by adding 584 mg/L of L-glutamine in no glucose, no glutamine, and no phenol red DMEM. Cells are exposed to Low Glu media for 1 hour before imaging. For the dynamic imaging (FIGS. 4A-4C), images are taken after exposure to Low Glu media (Normal media group), Low Glu media that had been nitrogen bubbled for 6 hour (Hypoxia group), or No Glu media (Glucose starvation group). Dynamic data are acquired from 3 dishes for each group. For the static imaging (FIGS. 4D-1 through 4I), images are taken right after exposure of HFKs to Low Glu media (Normal media group), right after exposure to Low Glu media that had been nitrogen bubbled for 6 hour (Hypoxia group), or after 30 min of exposure to No Glu media (Glucose starvation group). Static data are acquired from 4 dishes for each group, with a total of 16 fields per group (4 fields per dish).

Mouse HL-1 cardiomyocytes are maintained in Claycomb media (Sigma-Alrich). Images are taken right after exposure to low-dose CCCP (50 µM) or vehicle. We prepared 4 dishes for each group, and acquired a total of 16 fields per group (4 fields per dish).

Mouse C2C12 myoblasts are maintained in DMEM supplemented with 10% fetal bovine serum. Cells are differentiated by replacing the medium with DMEM containing 2% horse serum. After 3 days of differentiation, C2C12 cells expressing the muscle marker desmin are starved for 4 hour, and then transferred to serum-free DMEM containing 2% bovine serum albumin with or without fatty acids (Sigma-Alrich). We treated cells with the unsaturated fatty acid oleate (200 µM) or the saturated fatty acid palmitate (200 µM). Vehicle-treated cells are used as controls. Data are acquired from 3 dishes for each group, with a total of 12 fields per group (4 fields per dish).

Human mesenchymal stem cells (MSCs) are cultured using a previously established method. MSCs are isolated from bone marrow aspirate and cultured in MSC proliferation medium consisting of minimum essential medium (MEM) a combined with 10% fetal bovine serum (FBS), 1% antibiotic/antimycotic, 1% non-essential amino acids (NEAA) and 1 ng/mL basic fibroblastic growth factor at 37° C. with 5% CO2 in a humidified environment, until reaching confluence. Cell culture reagents are purchased from Life Technologies (Grand Island, N.Y.) unless otherwise noted. To induce adipogenic differentiation, Dulbecco's Modified Eagle Medium with F12 nutrient mixture (DMEM/F12) was supplemented with 3% FBS, 1% antibiotic/antimycotic, human recombinant insulin (1 µM), dexamethasone (1 µM), pantothenate (17 µM), biotin (33 µM), 2,3-thiazolidinediones (5 µM), and 3-isobutyl-1-methylxanthine (500 µM). Induction factors are purchased from Sigma-Alrich. Data are acquired at 3 weeks post adipogenic differentiation induction. We prepared 4 dishes for each group, and acquired a total of 8 fields per group (2 fields per dish).

Brown Adipose Tissue (BAT) Preparation: All procedures involving animal tissues are approved by the Tufts University Institutional Animal Care and Use Committee (IACUC). Twelve week old C57BL/6J male mice are housed in individual cages and acclimated at 18 ° C. for 2 days, followed by cold exposure at 4° C. for another 2 days with a 12-hour light-dark cycle and free access to a standard chow. A control group of mice was kept at 22-25 ° C. over the same period.

For in vivo imaging, BAT depots of mice are surgically exposed, under isofluorane anesthesia. There are three mice for each group, and five fields are imaged from each depot using a 25× objective. Mouse body temperature was maintained with a custom heated stage. Motion artifacts are minimized by gluing the tissue to a cover-glass with cyanoacrylate-latex. After imaging, the mice are euthanized by isofluorane anesthesia followed by cervical dislocation. Upon sacrifice interscapular BAT tissues are extracted, immediately snap frozen in dry ice, and kept at −80° C. until imaging (n=3 mice per group). Two or three tissue samples are taken from each mouse, and 6 fields per mouse are acquired from the control and the cold exposure group, respectively.

Method Details

TPEF Data Acquisition: For TPEF imaging, cell cultures are placed in home-made micro-incubator system, which maintained 37° C. and 5% CO2 within a humidified environment throughout the imaging session. BAT tissue samples are placed on glass coverslips with PBS to prevent drying while imaging at room temperature, and the imaging was limited within 2 hours of tissue thawing. Images are obtained using a custom-built microscope with a 40× water dipping objective (NA 1.1) or a 25× water dipping objective (NA 0.95, for in vivo imaging only) equipped with a tunable (710-920 nm) Ti: sapphire laser (Mai Tai; Spectra Physics; Mountain View, Calif.). Emission events are registered by a photomultiplier tube (PMT) detector attached to a commercial time-correlated single photon counting (TCSPC) electronics module. To isolate NADH fluorescence, a 460(±20) nm emission filter (Chroma, ET460/40M-2P), corresponding to the NADH emission peak, was placed before the detector. NADH fluorescence images are acquired from this 460 nm detector using 755 nm excitation. FAD fluorescence was isolated using 525(±25) nm emission filter (Chroma, ET525/50M-2P) and 860 nm excitation. For cell cultures, images (512×512 pixels; 184×184 µm) are acquired with an integration time of 60 s, using a laser power of –20 mW at 755 nm and –15 mW at 860 nm. For ex vivo BAT tissue samples, images with the same resolution as for cell cultures are acquired with an integration time of 120 s, using a laser power of –40 mW at 755 nm and –30 mW at 860 nm. For in vivo BAT imaging, images (512×512 pixels; 294×294 µm) are acquired with an integration time of 120 s, using a laser power of ~99 mW at 755 nm and ~92 mW at 860 nm. The laser power and PMT gain are recorded for each image and used to normalize fluorescence intensity.

Quantification And Statistical Analysis

Optical Redox Ratio Calculation: To process the optical redox ratio, firstly the fluorescence intensity of either NADH or FAD at each pixel was taken as the total photon counts detected during the integration time without spatial binning. For cell cultures, the cytoplasm of cells was selected based on the intensity threshold (FIG. 2F), while the segmentation of cell cytoplasm and lipid areas for BAT tissues was extracted by a combination of fluorescence intensity and lifetime information (FIGS. 7I-7F). Pixel-wise redox ratio maps are created by normalized fluorescence intensities as: FAD/(FAD+NADH). These redox ratio maps are color-coded in MATLAB and multiplied by merged gray scale intensity images of NADH and FAD for visualization purposes, as demonstrated in FIGS. 4A-14F. The mean redox ratio was acquired by averaging the redox ratio values within only the cell cytoplasm areas.

Phasor Fluorescence Lifetime Analysis: Using a commercial TCSPC electronics module, we acquired the NADH fluorescence decay $I_{m,n}$ at each pixel of an image, where (m, n) is the pixel location. Then real and imaginary parts of the Fourier transform of the decay curve at each pixel are used to determine the x and y axis coordinates of a phasor (FIG. 2D). A phasor is generally defined as a vector, whose direction relative to the x axis represents the phase of a wave and its length the amplitude. Fluorescence lifetime spectra characterized by a mono-exponential decay will map onto a point that falls on the universal semi-circle (FIG. 2D). More complicated decay curves are represented by points within the semi-circle. The phasors of spectra described well by a bi-exponential decay fall on a line within the semi-circle, with the two points where the line intersects the semi-circle representing the short and long lifetime components. The relative distance of the point on that line provides an estimate of the fractional contributions of the free (short lifetime) and bound (long lifetime) NADH components (FIG. 2D). The bound NADH fraction is estimated based on the location of the centroid of ellipses that represent the distributions of the detected fluorescence decay data. This metric is used throughout this study to resolve NADH lifetime information. The fractional contribution can be quantified per pixel, yielding the color-coded (by MATLAB) bound NADH fraction image maps (FIG. 2E). The mean bound NADH fraction of each image is acquired by averaging the values within only the cell cytoplasm areas.

PSD Based Mitochondrial Clustering Characterization: To assess mitochondrial clustering, we used a Fourier technique to obtain power spectral density (PSD) curves from each image. Briefly, the image intensity patterns within the cell cytoplasm regions selected by binary mask (FIG. 2F) are cloned and randomly positioned in the image background to create a new image without distinct cell borders and only cell mitochondrial patterns spanning the entire image (FIG. 2G). Upon Fourier transform a PSD-frequency curve was created for each image. We identified an inverse power law behavior of PSD curve at high spatial frequencies (>0.1 µm-1, corresponding to the size of mitochondria), suggesting a fractal organization of mitochondria and appearing as a linear portion in log-log space. We then fitted this linear portion between 0.1 µm-1 and the frequency at 98% of the entire PSD region (marked by asterisk, FIG. 1H) and acquired the exponential power, β, which is an indicator of the mitochondrial clustering used herein.

Cell-based Analysis: In order to assess the ability of distinguishing different metabolic pathways by a combination of redox ratio, bound NADH fraction and mitochondrial clustering at cellular level, as well as the heterogeneity of these three optical metrics under different perturbations, we did the cell based analysis complementary to the well (or animal) based one. Briefly, we randomly selected 6-8 cells from each image of field, and acquired the mean redox ratio, mean bound NADH fraction and mitochondrial clustering within the cytoplasm area of each cell. Specifically, the mitochondrial clustering was calculated by clone stamping the cytoplasm area of the selected cell to create a new image followed by Fourier transform. These cell based data are then grouped according to different perturbations for discriminant analysis (FIGS. 17A-17D6, 15A-15F) or for visualization of heterogeneity (FIGS. 7D-1 through 7D-6). Due to the functional and metabolic output similarities, the ex vivo and in vivo BAT cold activation data are merged into a single group.

Calculation of Heterogeneity Index: The heterogeneity index of each optical biomarker was calculated. Briefly, based on the single cell data, frequency histograms are plotted for the optical redox ratio, NADH bound fraction and mitochondrial clustering. We fit the histograms to one-, two-, or three-component Gaussian curves, with the lowest Akaike Information Criterion indicating optimal fitting. The heterogeneity index is defined as $$H = -\Sigma d_i p_i \ln p_i$$

where i represents each Gaussian component, d represents the distance between the median of the Gaussian component and the median of all data within a biological replicate of a certain group, and p represents the proportion of this component.

The heterogeneity indices of optical biomarkers in these experiments are shown in FIG. 16, with the significance symbol revealing significant difference compared with corresponding control.

Statistical Analysis: For samples with multiple groups (HFKs and C2C12 cells), an ANOVA with post-hoc Tukey HSD test was used to assess significant differences in redox ratio, NADH bound fraction or mitochondrial organization using JMP 12 (SAS). Otherwise a two-tailed t-test was used. Results are considered significant at p<0.05. For evaluating the 1, 2 or 3-metric separation models canonical linear discriminant analysis was performed. Discrimination accuracies are calculated with the linear discriminant functions determined and applied using the entire data set as well as a leave-one-out cross validation scheme acquired by running discriminant function analysis using SPSS.

Those having ordinary skill in the art will appreciate that various changes can be made to the embodiments without departing from the scope of the invention.

What is claimed is:

1. A method for assessing cellular metabolic activity, comprising:
    illuminating at least one cell with optical radiation so as to cause multi-photon excitation of at least two endogenous metabolic cofactors in said at least one cell, thereby causing said at least two excited metabolic cofactors to emit fluorescent radiation;
    using a detector to detect said fluorescent radiation emitted by said at least two excited metabolic cofactors;
    using a computer processor to analyze said fluorescent radiation to derive the following parameters: (1) an optical redox ratio of said at least two metabolic cofactors, (2) a fluorescence lifetime of at least one of said at least two metabolic cofactors, and (3) a parameter indicative of mitochondrial clustering in said at least one cell; and
    determining an increase in glycolysis level relative to oxidative phosphorylation in said at least one cell by concurrently detecting: (1) a reduction in said optical redox ratio, (2) a decrease in said fluorescence lifetime, and (3) an increase in said mitochondrial clustering parameter as compared to said optical redox ratio, said fluorescence lifetime and said mitochondrial clustering parameter when said glycolysis level and said oxidative phosphorylation in said at least one cell are balanced relative to one another.

2. The method of claim 1, wherein said at least two metabolic cofactors comprise an NAD(P)H and a flavin.

3. The method of claim 2, wherein said flavin comprises FAD.

4. The method of claim 1, wherein said optical radiation has a wavelength in a range of about 600 nm to about 1400 nm.

5. The method of claim 4, wherein said fluorescent radiation has a wavelength in a range of about 400 nm to about 650 nm.

6. The method of claim 1, further comprising using the computer processor to form a fluorescent image of said at least one cell based on said detected fluorescent radiation.

7. The method of claim 6, further comprising analyzing intensity associated with a plurality of pixels in said image to derive said mitochondrial clustering parameter.

8. The method of claim 6, further comprising using the computer processor to perform the following steps:
    segmenting said image by selecting a plurality of pixels corresponding to mitochondria and masking other pixels in the image;
    normalizing pixel intensities in the segmented image;
    assigning an intensity for each of the masked pixels via digital object cloning so as to generate a processed image;
    obtaining a Fourier transform of said processed image so as to determine a power spectral density associated with said processed image; and
    using said power spectral density to compute said mitochondrial clustering parameter.

9. The method of claim 8, wherein using the power spectral density comprises fitting said power spectral density to an inverse power law decay expression for computing said clustering parameter.

10. The method of claim 9, further including fitting said power spectral density to following relation: $R(k)=Ak^{-\beta}$, wherein, k denotes spatial frequency, A is an amplitude parameter, and $\beta$ denotes the mitochondrial clustering parameter.

11. A method for assessing cellular metabolic activity, comprising:
    illuminating at least one cell with optical radiation so as to cause multi-photon excitation of at least two endogenous metabolic cofactors in said at least one cell, thereby causing said at least two excited metabolic cofactors to emit fluorescent radiation;
    using a detector to detect said fluorescent radiation emitted by said at least two excited metabolic cofactors;
    using a computer processor to analyze said fluorescent radiation to derive the following parameters: (1) an optical redox ratio of said at least two metabolic cofactors, (2) a fluorescence lifetime of at least one of said at least two metabolic cofactors, and (3) a parameter indicative of mitochondrial clustering in said at least one cell; and
    determining an increase in glutaminolysis in said at least one cell by concurrently detecting: (1) an increase in said optical redox ratio, (2) an increase in said fluorescence lifetime, and (3) a decrease in said mitochondrial clustering parameter as compared to said optical redox ratio, said fluorescence lifetime and said mitochondrial clustering parameter when said glutaminolysis is measured when no metabolic perturbations in said at least one cell are present.

12. The method of claim 11, wherein said at lest two metabolic cofactors comprise NAD(P)H and a flavin.

13. The method of claim 12, wherein said flavin comprises FAD.

14. The method of claim 11, wherein said optical radiation has a wavelength in a range of about 600 nm to about 1400 nm.

15. The method of claim 14, wherein said fluorescent radiation has a wavelength in a range of about 400 nm to about 650 nm.

16. The method of claim 11, further comprising using the computer processor to form a fluorescent image of said at least one cell based on said detected fluorescent radiation.

17. The method of claim 16, further comprising analyzing intensity associated with a plurality of pixels in said image to derive said mitochondrial clustering parameter.

18. The method of claim 16, further comprising using the computer processor to perform the following steps:
    segmenting said image by selecting a plurality of pixels corresponding to mitochondria and masking other pixels in the image;
    normalizing pixel intensities in the segmented image;
    assigning an intensity for each of the masked pixels via digital object cloning so as to generate a processed image;
    obtaining a Fourier transform of said processed image so as to determine a power spectral density associated with said processed image; and
    using said power spectral density to compute said mitochondrial clustering parameter.

19. The method of claim 18, wherein using the power spectral density comprises fitting said power spectral density to an inverse power law decay expression for computing said clustering parameter.

20. The method of claim 19, further including fitting said power spectral density to following relation: $R(k)=Ak^{-\beta}$, wherein, k denotes spatial frequency, A is an amplitude parameter, and $\beta$ denotes the mitochondrial clustering parameter.

21. A method for assessing cellular metabolic activity, comprising:
    illuminating at least one cell with optical radiation so as to cause multi-photon excitation of at least two endogenous metabolic cofactors in said at least one cell, thereby causing said at least two excited metabolic cofactors to emit fluorescent radiation;
    using a detector to detect said fluorescent radiation emitted by said at least two excited metabolic cofactors;
    using a computer processor to analyze said fluorescent radiation to derive the following parameters: (1) an optical redox ratio of said at least two metabolic cofactors, (2) a fluorescence lifetime of at least one of said at least two metabolic cofactors, and (3) a parameter indicative of mitochondrial clustering in said at least one cell; and
    determining a fatty acid synthesis in said at least one cell by concurrently detecting: (1) an decrease in said optical redox ratio, (2) an increase in said fluorescence lifetime, and (3) an increase in said mitochondrial clustering parameter as compared to said optical redox ratio, said fluorescence lifetime and said mitochondrial clustering parameter when no fatty acid synthesis takes place in the at least one cell.

22. The method of claim 21, wherein said at least two metabolic cofactors comprise an NAD(P)H and a flavin.

23. The method of claim 22, wherein said flavin comprises FAD.

24. The method of claim 21, wherein said optical radiation has a wavelength in a range of about 600 nm to about 1400 nm.

25. The method of claim 24, wherein said fluorescent radiation has a wavelength in a range of about 400 nm to about 650 nm.

26. The method of claim 21, further comprising using the computer processor to form a fluorescent image of said at least one cell based on said detected fluorescent radiation.

27. The method of claim 26, further comprising analyzing intensity associated with a plurality of pixels in said image to derive said mitochondrial clustering parameter.

28. The method of claim 26, further comprising using the computer processor to perform the following steps:
    segmenting said image by selecting a plurality of pixels corresponding to mitochondria and masking other pixels in the image;
    normalizing pixel intensities in the segmented image;
    assigning an intensity for each of the masked pixels via digital object cloning so as to generate a processed image;
    obtaining a Fourier transform of said processed image so as to determine a power spectral density associated with said processed image; and
    using said power spectral density to compute said mitochondrial clustering parameter.

29. The method of claim 28, wherein using the power spectral density comprises fitting said power spectral density to an inverse power law decay expression for computing said clustering parameter.

30. The method of claim 29, further including fitting said power spectral density to following relation: $R(k)=Ak^{-\beta}$, wherein, k denotes spatial frequency, A is an amplitude parameter, and $\beta$ denotes the mitochondrial clustering parameter.

31. A method for assessing cellular metabolic activity, comprising:
    illuminating at least one cell with optical radiation so as to cause multi-photon excitation of at least two endogenous metabolic cofactors in said at least one cell, thereby causing said at least two excited metabolic cofactors to emit fluorescent radiation;
    using a detector to detect said fluorescent radiation emitted by said at least two excited metabolic cofactors;
    using a computer processor to analyze said fluorescent radiation to derive the following parameters: (1) an optical redox ratio of said at least two metabolic cofactors, (2) a fluorescence lifetime of at least one of said at least two metabolic cofactors, and (3) a parameter indicative of mitochondrial clustering in said at least one cell; and
    determining a chemically-induced uncoupling between generation of a proton gradient across an inner mitochondrial membrane and ATP production in said at least one cell by concurrently detecting: (1) an increase in said optical redox ratio, (2) an increase in said fluorescence lifetime, and (3) an increase in said mitochondrial clustering parameter as compared to said optical redox ratio, said fluorescence lifetime and said mitochondrial clustering parameter when said chemically-induced uncoupling does not occur in said at least one cell.

32. The method of claim 31, wherein said at least two metabolic cofactors comprise NAD(P)H and a flavin.

33. The method of claim 32, wherein said flavin comprises FAD.

34. The method of claim 31, wherein said optical radiation has a wavelength in a range of about 600 nm to about 1400 nm.

35. The method of claim 34, wherein said fluorescent radiation has a wavelength in a range of about 400 nm to about 650 nm.

36. The method of claim 31, further comprising using the computer processor to form a fluorescent image of said at least one cell based on said detected fluorescent radiation.

37. The method of claim 36, further comprising analyzing intensity associated with a plurality of pixels in said image to derive said mitochondrial clustering parameter.

38. The method of claim 36, further comprising using the computer processor to perform the following steps:
    segmenting said image by selecting a plurality of pixels corresponding to mitochondria and masking other pixels in the image;
    normalizing pixel intensities in the segmented image;
    assigning an intensity for each of the masked pixels via digital object cloning so as to generate a processed image;
    obtaining a Fourier transform of said processed image so as to determine a power spectral density associated with said processed image; and
    using said power spectral density to compute said mitochondrial clustering parameter.

39. The method of claim 38, wherein using the power spectral density comprises fitting said power spectral density to an inverse power law decay expression for computing said clustering parameter.

40. The method of claim 39, further including fitting said power spectral density to following relation: $R(k)=Ak^{-\beta}$, wherein, k denotes spatial frequency, A is an amplitude parameter, and $\beta$ denotes the mitochondrial clustering parameter.

41. A method for assessing cellular metabolic activity, comprising:
   illuminating at least one cell with optical radiation so as to cause multi-photon excitation of at least two endogenous metabolic cofactors in said at least one cell, thereby causing said at least two excited metabolic cofactors to emit fluorescent radiation;
   using a detector to detect said fluorescent radiation emitted by said at least two excited metabolic cofactors;
   using a computer processor to analyze said fluorescent radiation to derive the following parameters: (1) an optical redox ratio of said at least two metabolic cofactors, (2) a fluorescence lifetime of at least one of said at least two metabolic cofactors, and (3) a parameter indicative of mitochondrial clustering in said at least one cell; and
   determining thermogenesis associated uncoupling between generation of a proton gradient across an inner mitochondrial membrane and ATP production in said at least one cell by concurrently detecting: (1) an increase in said optical redox ratio, (2) a decrease in said fluorescence lifetime, and (3) an increase in said mitochondrial clustering parameter as compared to said optical redox ratio, said fluorescence lifetime and said mitochondrial clustering parameter when said thermogenesis associated uncoupling does not occur in said at least one cell.

42. The method of claim 41, wherein said at least two metabolic cofactors comprise NAD(P)H and a flavin.

43. The method of claim 42, wherein said flavin comprises FAD.

44. The method of claim 41, wherein said optical radiation has a wavelength in a range of about 600 nm to about 1400 nm.

45. The method of claim 44, wherein said fluorescent radiation has a wavelength in a range of about 400 nm to about 650 nm.

46. The method of claim 41, further comprising using the computer processor to form a fluorescent image of said at least one cell based on said detected fluorescent radiation.

47. The method of claim 46, further comprising analyzing intensity associated with a plurality of pixels in said image to derive said mitochondrial clustering parameter.

48. The method of claim 46, further comprising using the computer processor to perform the following steps:
   segmenting said image by selecting a plurality of pixels corresponding to mitochondria and masking other pixels in the image;
   normalizing pixel intensities in the segmented image;
   assigning an intensity for each of the masked pixels via digital object cloning so as to generate a processed image;
   obtaining a Fourier transform of said processed image so as to determine a power spectral density associated with said processed image; and
   using said power spectral density to compute said mitochondrial clustering parameter.

49. The method of claim 48, wherein using the power spectral density comprises fitting said power spectral density to an inverse power law decay expression for computing said clustering parameter.

50. The method of claim 49, further including fitting said power spectral density to following relation: $R(k)=Ak^{-\beta}$, wherein, k denotes spatial frequency, A is an amplitude parameter, and $\beta$ denotes the mitochondrial clustering parameter.

51. A method for assessing cellular metabolic activity, comprising:
   illuminating at least one cell with optical radiation so as to cause multi-photon excitation of at least two endogenous metabolic cofactors in said at least one cell, thereby causing said at least two excited metabolic cofactors to emit fluorescent radiation;
   using a detector to detect said fluorescent radiation emitted by said at least two excited metabolic cofactors;
   using a computer processor to analyze said fluorescent radiation to derive the following parameters: (1) an optical redox ratio of said at least two metabolic cofactors, (2) a fluorescence lifetime of at least one of said at least two metabolic cofactors, and (3) a parameter indicative of mitochondrial clustering in said at least one cell; and
   determining an increase in fatty acid oxidation in said at least one cell by concurrently detecting: (1) a decrease in said optical redox ratio, (2) a decrease in said fluorescence lifetime, and (3) any of a decrease and no change in said mitochondrial clustering parameter as compared to said optical redox ratio, said fluorescence lifetime and said mitochondrial clustering parameter when said fatty acid oxidation is measured when no metabolic perturbations in said at least one cell are present.

52. The method of claim 51, wherein said at least two metabolic cofactors comprise NAD(P)H and a flavin.

53. The method of claim 52, wherein said flavin comprises FAD.

54. The method of claim 51, wherein said optical radiation has a wavelength in a range of about 600 nm to about 1400 nm.

55. The method of claim 54, wherein said fluorescent radiation has a wavelength in a range of about 400 nm to about 650 nm.

56. The method of claim 51, further comprising using the computer processor to form a fluorescent image of said at least one cell based on said detected fluorescent radiation.

57. The method of claim 56, further comprising analyzing intensity associated with a plurality of pixels in said image to derive said mitochondrial clustering parameter.

58. The method of claim 56, further comprising using the computer processor to perform the following steps:
   segmenting said image by selecting a plurality of pixels corresponding to mitochondria and masking other pixels in the image;
   normalizing pixel intensities in the segmented image;
   assigning an intensity for each of the masked pixels via digital object cloning so as to generate a processed image;
   obtaining a Fourier transform of said processed image so as to determine a power spectral density associated with said processed image; and
   using said power spectral density to compute said mitochondrial clustering parameter.

59. The method of claim 58, wherein using the power spectral density comprises fitting said power spectral density to an inverse power law decay expression for computing said clustering parameter.

60. The method of claim 59, further including fitting said power spectral density to following relation: $R(k)=Ak^{-\beta}$, wherein, k denotes spatial frequency, A is an amplitude parameter, and β denotes the mitochondrial clustering parameter.

\* \* \* \* \*